(12) United States Patent
Kodera et al.

(10) Patent No.: US 8,114,651 B2
(45) Date of Patent: Feb. 14, 2012

(54) METHOD FOR PRODUCING 4-HYDROXY-L-ISOLEUCINE

(75) Inventors: Tomohiro Kodera, Kawasaki (JP); Sergey Vasilievich Smirnov, Moscow (RU); Natalia Nikolaevna Samsonova, Moscow (RU); Veronika Aleksandrovna Kotliarova, Moscow (RU); Natalia Yurievna Rushkevich, Moscow (RU); Yury Ivanovich Kozlov, Moscow (RU); Vitaly Grigorievich Paraskevov, legal representative, Moscow (RU); Sakayu Shimizu, Kyoto (JP); Jun Ogawa, Kyoto (JP); Makoto Hibi, Kyoto (JP)

(73) Assignee: Ajinomoto Co., Inc., Tokyo (JP)

( * ) Notice: Subject to any disclaimer, the term of this patent is extended or adjusted under 35 U.S.C. 154(b) by 99 days.

(21) Appl. No.: 12/412,823

(22) Filed: Mar. 27, 2009

(65) Prior Publication Data

US 2009/0275092 A1 Nov. 5, 2009

Related U.S. Application Data

(63) Continuation of application No. PCT/JP2007/069520, filed on Sep. 28, 2007.

(60) Provisional application No. 60/829,577, filed on Oct. 16, 2006.

(30) Foreign Application Priority Data

| Sep. 28, 2006 | (JP) | 2006-265452 |
| Dec. 22, 2006 | (JP) | 2006-345461 |
| Feb. 7, 2007 | (RU) | 2007104645 |

(51) Int. Cl.
*C12N 9/02* (2006.01)
*C12N 15/00* (2006.01)
*C12P 21/04* (2006.01)

(52) U.S. Cl. ....... 435/189; 435/69.1; 435/71.1; 435/440

(58) Field of Classification Search .................. None
See application file for complete search history.

(56) References Cited

U.S. PATENT DOCUMENTS

| 6,960,455 | B2 | 11/2005 | Livshits et al. |
| 7,138,266 | B2 | 11/2006 | Debabov et al. |
| 7,179,623 | B2 | 2/2007 | Livshits et al. |
| 7,186,531 | B2 | 3/2007 | Akhverdian et al. |
| 7,300,786 | B2 | 11/2007 | Klyachko et al. |
| 7,381,548 | B2 | 6/2008 | Sheremet'eva et al. |
| 7,399,618 | B2 | 7/2008 | Klyachko et al. |
| 7,422,880 | B2 | 9/2008 | Rybak et al. |
| 7,470,524 | B2 | 12/2008 | Rybak et al. |
| 2005/0048631 | A1 | 3/2005 | Klyachko et al. |
| 2005/0181488 | A1 | 8/2005 | Akhverdian et al. |
| 2005/0214911 | A1 | 9/2005 | Marchenko et al. |
| 2006/0040365 | A1 | 2/2006 | Kozlov et al. |
| 2006/0088919 | A1 | 4/2006 | Rybak et al. |
| 2007/0212764 | A1 | 9/2007 | Ptitsyn et al. |
| 2008/0113416 | A1 | 5/2008 | Filippov et al. |
| 2008/0241888 | A1 | 10/2008 | Zakataeva et al. |
| 2009/0081738 | A1 | 3/2009 | Filippov et al. |

FOREIGN PATENT DOCUMENTS

| WO | WO2006/093322 | 9/2006 |
| WO | WO2008/044614 | 4/2008 |
| WO | WO2008/154750 | 12/2008 |

OTHER PUBLICATIONS

Branden et al. Introduction to Protein Structure, Garland Publishing Inc., New York, p. 247, 1991.*
Database UNIPROTKB, Nov. 8, 2005, Database accession No. Q3EZS9.
Database UNIPROTKB, Jun. 1, 2003, Database accession No. Q81GX0.
Database EMBL, Jan. 1, 2006, Databases accession No. AE016877.
De Carolis, E., et al., 2-Oxoglutarate-Dependent Dioxygenase and Related Enzymes: Biochemical Characterization, Phytochemistry 1994;36(5):1093-1107.
Haefele, C., et al., "Characterization of a Dioxygenase from *Trigonella foenum-graecum* Involved in 4-Hydroxyisoleucine Biosynthesis," Phytochemistry 1997;44(4):563-566.
Narender, T., et al., "4-Hydroxyisoleucine an unusual amino acid as antidyslipidemic and antihyperglycemic agent," Bioorg. Med. Chem. Lett. 2006;16:293-296.
Ogawa, J., et al., "Synthesis of 4-Hydroxyisoleucine by the Aldolase-Transaminase Coupling Reaction and Basic Characterization of the Aldolase from *Arthrobacter simplex* AKU 626," Biosci. Biotechnol. Biochem. 2007;71(7):1607-1615.
Smirnov, S. V., et al., "A novel strategy for enzymatic synthesis of 4-hydroxyisoleucine: identification of an enzyme possessing HMKP (4-hydroxy-3-methyl-2-keto-pentanoate) aldolase activity," FEMS Microbiol. Lett. 2007;273:70-77.
Internation Search Report and Written Opinion of the International Searching Authority for PCT Patent App. No. PCT/JP2007/069520 (Mar. 7, 2008).
Sergent, D., et al., "Synthesis of hydantoin analogues of (2S,3R,4S)-4-hydroxyisoleucine with insulinotropic properties," Bioorg. Med. Chem. Lett. 2008;18:4332-4335.
International Preliminary Report on Patentability for PCT Patent App. No. PCT/JP2007/069520 (Apr. 9, 2009).
U.S. Appl. No. 11/830,969, filed Jul. 31, 2007, Gulevich et al.
U.S. Appl. No. 11/849,403, filed Sep. 4, 2007, Rybak et al.
U.S. Appl. No. 11/952,297, filed Dec. 7, 2007, Rybak et al.
U.S. Appl. No. 12/022,299, filed Jan. 30, 2008, Rybak et al.
U.S. Appl. No. 12/031,757, filed Feb. 15, 2008, Klyachko et al.
U.S. Appl. No. 61/058,313, filed Jun. 3, 2008, Ermishev et al.
U.S. Appl. No. 12/212,743, filed Sep. 18, 2008, Rybak et al.
U.S. Appl. No. 12/212,767, filed Sep. 18, 2008, Smirnov et al.
U.S. Appl. No. 12/275,842, filed Nov. 21, 2008, Rybak et al.
U.S. Appl. No. 12/349,743, filed Jan. 7, 2009, Marchenko et al.
U.S. Appl. No. 12/364,042, filed Jan. 15, 2009, Ptitsyn et al.

* cited by examiner

*Primary Examiner* — Yong Pak
(74) *Attorney, Agent, or Firm* — Shelly Guest Cermak

(57) ABSTRACT

A highly active L-isoleucine dioxygenase from *Bacillus thuringiensis* is provided. A method for manufacturing (2S,3R,4S)-4-hydroxy-L-isoleucine or a salt thereof by reacting L-isoleucine in an aqueous solvent in the presence of L-isoleucine dioxygenase and isolating (2S,3R,4S)-4-hydroxy-L-isoleucine is also provided.

3 Claims, 13 Drawing Sheets

```
Fragment of genome sequence of the Bacillus thuringiensis ser.
        israelensis ATCC35646 strain (RBTH_06809 ORF).

IDO(Met)
                                    IDO(Lys)
                  #              ##
                    MetThrPheValLeuSerLysMetSer...ThrLys***
5'-...gtggaggttttataatgacgtttgttcttagtaaaatgagt...acaaaatga...-3'
        SD                            ↑ putative                stop
                                      processing site

#  - putative translation start of RBTH_06809
- determined N-terminal amino acid of purified IDO from 2-e-2
strain (AJICO)
```

Fig. 14

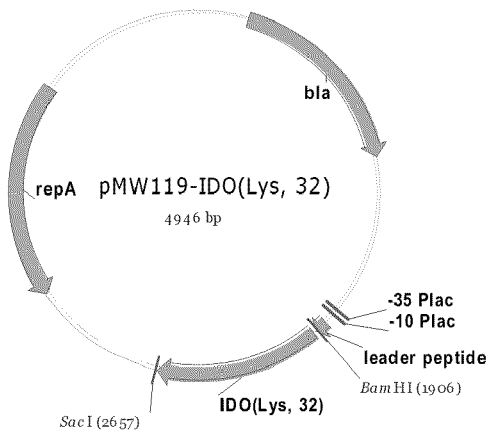

```
         BamHI
         ~~~~~~
                              MetLys MetSerGlyPhe SerIleGlu GluLysVal HisGluPheGlu·
    1    GGATCCTTAA GAAGGAGATA TACCATGAAA ATGAGTGGCT TTAGCATAGA AGAAAAGGTA CATGAATTTG
         ·GSerLysGly PheLeuGlu IleSerAsnGlu IlePheLeu GlnGluGlu GluAsnHisSer LeuLeuThr·
   71    AATCTAAAGG GTTTCTTGAA ATCTCAAATG AAATCTTTTT ACAAGAGGAA GAGAATCATA GTTTATTAAC
         ·GlnAlaGln LeuAspTyrTyr AsnLeuGlu AspAspAla TyrGlyGluCys ArgAlaArg SerTyrSer·
  141    ACAAGCACAG TTAGATTATT ATAATTTGGA AGATGATGCG TACGGTGAAT GCCGTGCTAG ATCTTATTCA
         ArgTyrIleLys TyrValAsp SerProAsp TyrIleLeuAsp AsnSerAsn AspTyrPhe GlnSerLysGlu·
  211    AGGTATATAA AGTATGTTGA TTCACCAGAT TATATTTTAG ATAATAGTAA TGATTACTTC CAATCTAAAG
         ·GTyrAsnTyr AspAspGly GlyLysValArg GlnPheAsn SerIleAsn AspSerPheLeu CysAsnPro·
  281    AATATAACTA TGATGATGGC GGGAAAGTTA GACAGTTCAA TAGCATAAAT GATAGCTTTT TGTGTAATCC
         ·LeuIleGln AsnIleValHis PheAspThr GluPheAla PheLysThrAsn IleIleAsp LysSerLys
  351    TTTAATTCAA AATATCGTGC ATTTCGATAC TGAGTTTGCA TTTAAAACAA ATATAATAGA TAAAAGTAAA
         AspLeuIleIle GlyLeuHis GlnValArg TyrLysAlaThr LysGluArg ProSerPhe SerSerProIle·
  421    GATTTAATTA TAGGCTTACA TCAAGTAAGA TATAAAGCTA CTAAAGAAAG ACCATCTTTT AGTTCACCTA
         ·ITrpLeuHis LysAspAsp GluProValVal PheLeuHis LeuMetAsn LeuSerAsnThr AlaIleGly·
  491    TTTGGTTACA TAAAGATGAT GAACCAGTAG TGTTTTTACA CCTTATGAAT TTAAGTAATA CAGCTATCGG
         ·GlyAspAsn LeuIleAlaAsn SerProArg GluIleAsn GlnPheIleSer LeuLysGlu ProLeuGlu·
  561    CGGAGATAAT TTAATAGCTA ATTCTCCTCG GGAAATTAAT CAGTTTATAA GTTTGAAGGA GCCGTTAGAA
         ThrLeuValPhe GlyGlnLys ValPheHis AlaValThrPro LeuGlyThr GluCysSer ThrGluAlaPhe·
  631    ACTTTAGTAT TTGGACAAAA GGTCTTCCAT GCCGTAACGC CACTTGGAAC AGAATGTAGT ACGGAGGCTT
                                                                SacI
                                                                ~~~~~~~
         ·PArgAspIle LeuLeuVal ThrPheSerTyr LysGluThr Lys***
  701    TTCGTGATAT TTTATTAGTA ACATTTCTT ATAAGGAGAC AAAATAAGAG CTC
```

Fig. 17

```
                        1                                                                   70
IDO(Lys, RBTH)    (1)   AAAATGAGTGGCTTTAGCATAGAAGAAAAGGTACATGAATTTGAATCTAAGGGATTCCTTGAAATCTCAA
IDO(Lys, 23 )     (1)   AAAATGAGTGGCTTTAGCATAGAAGAAAAGGTACATGAATTTGAATCTAAAGGGTTTCTTGAAATCTCAA
IDO(Lys, 32)      (1)   AAAATGAGTGGCTTTAGCATAGAAGAAAAGGTACATGAATTTGAATCTAAAGGGTTTCTTGAAATCTCAA
                        71                                                                  140
IDO(Lys, RBTH)   (71)   ATGAAATCTTTTTACAAGAGGAAGAGAATCATCGTTTATTAACACAAGCACAGTTAGATTATTATAATTT
IDO(Lys, 23 )    (71)   ATGAAATCTTTTTACAAGAGGAAGAGAATCATAGTTTATTAACACAAGCACAGTTAGATTATTATAATTT
IDO(Lys, 32)     (71)   ATGAAATCTTTTTACAAGAGGAAGAGAATCATAGTTTATTAACACAAGCACAGTTAGATTATTATAATTT
                        141                                                                 210
IDO(Lys, RBTH)  (141)   GGAAGATGATGCGTACGGTGAATGCCGTGCTAGATCTTATTCAAGGTATATAAAGTATGTTGATTCACCA
IDO(Lys, 23 )   (141)   GGAAGATGATGCGTACGGTGAATGCCGTGCTAGATCTTATTCAAGGTATATAAAGTATGTTGATTCACCA
IDO(Lys, 32)    (141)   GGAAGATGATGCGTACGGTGAATGCCGTGCTAGATCTTATTCAAGGTATATAAAGTATGTTGATTCACCA
                        211                                                                 280
IDO(Lys, RBTH)  (211)   GATTATATTTTAGATAATAGTAATGATTACTTCCAATCTAAAGAATATAACTATGATGATGGCGGTAAAG
IDO(Lys, 23 )   (211)   GATTATATTTTAGATAATAGTAATGATTACTTCCAATCTAAAGAATATAACTATGATGATGGCGGGAAAG
IDO(Lys, 32)    (211)   GATTATATTTTAGATAATAGTAATGATTACTTCCAATCTAAAGAATATAACTATGATGATGGCGGGAAAG
                        281                                                                 350
IDO(Lys, RBTH)  (281)   TTAGACAGTTCCATAGCATAAATGATAGTTTTTTATATAATCCTTTAATTCAAAATATCGTGCGTTTCGA
IDO(Lys, 23 )   (281)   TTAGACAGTTCAATAGCATAAATGATAGCTTTTATGTAATCCTTTAATTCAAAATATCGTGCGTTTCGA
IDO(Lys, 32)    (281)   TTAGACAGTTCAATAGCATAAATGATACCTTTTGTCTAATCCTTTAATTCAAAATATCGTGCATTTCGA
                        351                                                                 420
IDO(Lys, RBTH)  (351)   TACTGAATTTGCATTTAAAACAAATATAATAGATACAAGTAAAGATTTAATTATAGGTTTACATCAAGTA
IDO(Lys, 23 )   (351)   TACTGAGTTTGCATTTAAAACAAATATAATACATAAAAGTAAAGATTTAATTATAGCCTTACATCAACTA
IDO(Lys, 32)    (351)   TACTGAGTTTGCATTTAAAACAAATATAATAGATAAAAGTAAAGATTTAATTATAGGCTTACATCAAGTA
                        421                                                                 490
IDO(Lys, RBTH)  (421)   AGATATAAAGCTACTAAAGAAAGACCATCTTTTAGTTCACCTATTTGGTTACATAAAGATGATGAACCAG
IDO(Lys, 23 )   (421)   AGATATAAAGCTACTAAAGAAAGACCATCTTTTAGTTCACCTATTTGGTTACATAAAGATGATGAACCAG
IDO(Lys, 32)    (421)   AGATATAAAGCTACTAAAGAAAGACCATCTTTTAGTTCACCTATTTGGTTACATAAAGATGATGAACCAG
                        491                                                                 560
IDO(Lys, RBTH)  (491)   TAGTGTTTTTACACCTTATGAATTTAAGTAATACAGCTATTGGCGGAGATAATTTAATAGCTAATTCTCC
IDO(Lys, 23 )   (491)   TAGTATTTTTACACCTTATGAATTTAAGTAATACAGCTATCGGCGGAGATAATTTAATAGCTAATTCTCC
IDO(Lys, 32)    (491)   TAGTGTTTTTACACCTTATGAATTTAAGTAATACAGCTATCGGCGGAGATAATTTAATAGCTAATTCTCC
                        561                                                                 630
IDO(Lys, RBTH)  (561)   AAGGGAAATTAATCAGTTTATAAGTTTGAAGGAGCCTTTAGAAACTTTAGTATTTGGACAAAAGGTTTTC
IDO(Lys, 23 )   (561)   TGGGGAAATTAATCAGTTTATAAGTTTGAAGGAGCCTTTAGAAACTTTAGTATTTGGACAAAAGGTGTTC
IDO(Lys, 32)    (561)   TCGGGAAATTAATCAGTTTATAAGTTTGAAGGAGCCGTTAGAAACTTTAGTATTTGGACAAAAGGTGTTC
                        631                                                                 700
IDO(Lys, RBTH)  (631)   CATGCCGTAACGCCACTTGGAACAGAATGTAGTACTGAAGCTTTTCGTGATATTTTATTAGTAACATTTT
IDO(Lys, 23 )   (631)   CATGCCGTAACGCCACTTGGAACAGAATGTAGTACGGAGGCTTTTCGTGATATTTTATTAGTAACATTTT
IDO(Lys, 32)    (631)   CATGCCCGTAACGCCACTTGGAACAGAATGTAGTACGCAGGCTTTTCGTGATATTTTATTAGTAACATTTT
                        701        717
IDO(Lys, RBTH)  (701)   CTTATAAGGAGACAAAATGA
IDO(Lys, 23 )   (701)   CTTATAAGGAGACAAAATAA
IDO(Lys, 32)    (701)   CTTATAAGGAGACAAAATAA
```

Fig. 18

```
                    1                                                                              80
IDO(Lys, RBTH)   (1) KMSGFSIEEKVHEFESKGFLEISNEIFLQEEENHRLLTQAQLDYYNLEDDAYGECRARSYSRYIKYVDSPDYILDNSNDY
  IDO(Lys, 23)   (1) KMSGFSIEEKVHEFESKGFLEISNEIFLQEEENHSLLTQAQLDYYNLEDDAYGECRARSYSRYIKYVDSPDYILDNSNDY
  IDO(Lys, 32)   (1) KMSGFSIEEKVHEFESKGFLEISNEIFLQEEENHSLLTQAQLDYYNLEDDAYGECRARSYSRYIKYVDSPDYILDNSNDY
                     81                                                                            160
IDO(Lys, RBTH)  (81) FQSKEYNYDDGGKVRQFHSINDSFLYNPLIQNIVRFDTEFAFKTNIIDTSKDLIIGLHQVRYKATKERPSFSSPIWLHKD
  IDO(Lys, 23)  (81) FQSKEYNYDDGGKVRQFNSINDSFLCNPLIQNIVRFDTEFAFKTNIIDKSKDLIIGLHQVRYKATKERPSFSSPIWLHKD
  IDO(Lys, 32)  (81) FQSKEYNYDDGGKVRQFNSINDSFLCNPLIQNIVHFDTEFAFKTNIIDKSKDLIIGLHQVRYKATKERPSFSSPIWLHKD
                     161                                                                        239
IDO(Lys, RBTH) (161) DEPVVFLHLMNLSNTAIGGDNLIANSPREINQFISLKEPLETLVFGQKVFHAVTPLGTECSTEAFRDILLVTFSYKETK
  IDO(Lys, 23) (161) DEPVVFLHLMNLSNTAIGGDNLIANSPREINQFISLKEPLETLVFGQKVFHAVTPLGTECSTEAFRDILLVTFSYKETK
  IDO(Lys, 32) (161) DEPVVFLHLMNLSNTAIGGDNLIANSPREINQFISLKEPLETLVFGQKVFHAVTPLGTECSTEAFRDILLVTFSYKETK
```

Fig. 19

```
Bacillus cereus.gnu                   1 KMNGFSIEEKVHEFESKGFLEISNEIFLQEEENHRLLTQAQLDYYNLEDDAYGECRARSY  60
Bacillus thuringiensis.gnu            1 KMSGFSIEEKVHEFESKGFLEISNEIFLQEEENHRLLTQAQLDYYNLEDDAYGECRARSY  60
Bacillus weihenstephanensis.gnu       1 KTSSFDVEQKVHEFESNGYIQIENDIFLQDQEDQALLIKAQLDYYSLQNDAYGECRARAY  60
Ile hydroxylase.gnu                   1 KXXXFXXEXKVHEFESXGXXXIXNXIFLQXXEXXXLLTXAQLDYYXLXXDAYGECRARXY  60

Bacillus cereus.gnu                  61 SRYIKYVDSPDYILDNSNDYFQSKEYNYDDGGKVRQINSINDSFLCNPLIQNIVRFDTEF 120
Bacillus thuringiensis.gnu           61 SRYIKYVDSPDYILDNSNDYFQSKEYNYDDGGKVRQFHSINDSFLYNPLIQNIVRFDTEF 120
Bacillus weihenstephanensis.gnu      61 SRYIKYAGSSDYVLDTDNGYFQSEEYNYDDGGKIRNINSITDEFLINSLIEKIVRFDSEF 120
Ile hydroxylase.gnu                  61 SRYIKYXXSXDYXLDXXNXYFQSXEYNYDDGGKXRXIXSIXDXFLXNXLIXXIVRFDXEF 120

Bacillus cereus.gnu                 121 AFKTNIIDTSKDLIIGLHQVRYKATKERPSFSSPIWLHKDDEPVVFLHLMNLSNTAIGGD 180
Bacillus thuringiensis.gnu          121 AFKTNIIDTSKDLIIGLHQVRYKATKERPSFSSPIWLHKDDEPVVFLHLMNLSNTAIGGD 180
Bacillus weihenstephanensis.gnu     121 ASNTNILDTSKDLVIGLHQVRYKATRENPSFSSPIWLHKDDEHIVFLHLMNLSNTALGGD 180
Ile hydroxylase.gnu                 121 AXXTNIXDTSKDLXIGLHQVRYKATXEXPSFSSPIWLHKDDEPXVFLHLMNLSNTAXGGD 180

Bacillus cereus.gnu                 181 NLIANSPREINQFISLKEPLETLVFGQKVFHAVTPLGTECSTEAFRDILLVTFSYKETK  239
Bacillus thuringiensis.gnu          181 NLIANSPREINQFISLKEPLETLVFGQKVFHAVTPLGTECSTEAFRDILLVTFSYKETK  239
Bacillus weihenstephanensis.gnu     181 NLIANSPREINKLISLKDPLETLVFGQKVFHAVTPLGTECNTEALRDILLVTFSYKEHK  239
Ile hydroxylase.gnu                 181 NLIANSPREINXXISLKXPLETLVFGQKVFHAVTPLGTECXTEAXRDILLVTFSYKEXK  239
```

Fig. 20

METHOD FOR PRODUCING 4-HYDROXY-L-ISOLEUCINE

This application is a continuation under 35 U.S.C. §120 to PCT Patent Application No. PCT/JP2007/069520, filed on Sep. 28, 2007, which claims priority under 35 U.S.C. §119 to Japanese Patent Application No. 2006-265452, filed Sep. 28, 2006, U.S. Provisional Patent Application No. 60/829,577, filed on Oct. 16, 2006, Japanese Patent Application No. 2006-345461, filed Dec. 22, 2006, and Russian Patent Application No. 2007104645, filed on Feb. 7, 2007, all of which are incorporated by reference. The Sequence Listing filed electronically herewith is also hereby incorporated by reference in its entirety (File Name: US-312_Seq_List; File Size: 26 KB; Date Created: Mar. 27, 2009)

BACKGROUND OF THE INVENTION

1. Technical Field

The present invention relates to the microbiological industry, and specifically to a novel dioxygenase and methods for manufacturing 4-hydroxy-L-isoleucine or a salt thereof.

2. Background Art 4-hydroxy-L-isoleucine is an amino acid which can be extracted and purified from fenugreek seeds (*Trigonella foenum-graecum L. leguminosae*). 4-Hydroxy-L-isoleucine has an insulinotropic activity, and is of great interest because its stimulating effect is clearly dependent on plasma glucose concentrations, as demonstrated both in isolated perfused rat pancreas and human pancreatic islets (Sauvaire, Y. et al, Diabetes, 47: 206-210, (1998)). The only class of insulinotropic drugs currently used to treat type II diabetes, or non-insulin-dependent diabetes (NIDD) mellitus (NIDDM), are sulfonylureas, and these drugs do not demonstrate this glucose dependency (Drucker, D. J., Diabetes 47: 159-169, (1998). As a result, hypoglycemia remains a common undesirable side effect of sulfonylurea treatment (Jackson, J., and Bessler, R. Drugs, 22: 211-245; 295-320, (1981); Jennings, A. et al. Diabetes Care, 12: 203-208, (1989)). Methods for improving glucose tolerance are also known (Am. J. Physiol. Endocrinol., Vol. 287, E463-E471, 2004). Enhancing glucometabolism activity, and the potential application of this activity in pharmaceuticals and health foods, has been reported (Japanese Patent Application Laid-Open No. Hei 6-157302, US2007-000463A1).

4-hydroxy-L-isoleucine, which is only found in plants, might be considered for the treatment of type II diabetes due to its particular insulinotropic action, since this is a disease characterized by defective insulin secretion associated with various degrees of insulin resistance (Broca, C. et al, Am. J. Physiol. 277 (Endocrinol. Metab. 40): E617-E623, (1999)).

Methods of oxidizing iron, ascorbic acid, 2-oxyglutaric acid, and oxygen-dependent isoleucine by utilizing dioxygenase activity in fenugreek extract has been reported for manufacturing 4-hydroxy-L-isoleucine (Phytochemistry, Vol. 44, No. 4, pp. 563-566, 1997). However, this method is unsatisfactory for manufacturing 4-hydroxy-L-isoleucine because the activity of the enzyme is inhibited by isoleucine concentrations of 20 mM and above, the enzyme has not been identified, the enzyme is derived from plant extracts and it is difficult to obtain large quantities, and the enzyme is unstable.

An efficient eight-step synthesis of optically pure (2S,3R,4S)-4-hydroxyisoleucine with a 39% overall yield has been disclosed. The key steps of this synthesis involve the biotransformation of ethyl 2-methylacetoacetate to ethyl (2S,3S)-2-methyl-3-hydroxy-butanoate with *Geotrichum candidum* and an asymmetric Strecker synthesis (Wang, Q. et al, Eur. J. Org. Chem., 834-839 (2002)).

A short six-step chemoenzymatic synthesis of (2S,3R,4S)-4-hydroxyisoleucine while controlling the stereochemistry, the last step being the enzymatic resolution by hydrolysis of a N-phenylacetyl lactone derivative using commercially available penicillin acylase G immobilized on Eupergit C(E-PAC), has also been disclosed (Rolland-Fulcrand, V. et al, J. Org. Chem., 873-877 (2004)).

But currently, the cloning of any L-isoleucine dioxygenase has not been reported, nor of its use for producing (2S,3R,4S)-4-hydroxy-L-isoleucine by direct enzymatic hydroxylation of L-isoleucine.

As for production of isoleucine analogues by microorganisms, production of 2-amino-3-keto-4-methylpentanoic acid (AMKP) by *Bacillus* bacteria has been reported (Bioorganic Chemistry, Vol. 6, pp. 263-271 (1977)). However, there are no reports about isoleucine hydroxylases derived from microorganisms.

SUMMARY OF THE INVENTION

An aspect of the present invention is to provide a method for producing 4-hydroxyisoleucine (which includes both the free form and salt forms f, and may referred to as "4HIL") by using an enzyme derived from a microorganism, which can be prepared in large amounts.

Aspects of the present invention include providing a microorganism having an enzymatic activity for producing 4-hydroxyisoleucine from isoleucine, and a method for producing 4-hydroxyisoleucine from isoleucine via a hydroxylation reaction using an enzyme derived from a microorganism. The above aspects were achieved by isolating a microorganism having an enzymatic activity for producing 4-hydroxyisoleucine from isoleucine.

An aspect of present invention is to enhance production of (2S,3R,4S)-4-hydroxy-L-isoleucine (which includes both the free form and salt forms, and may be referred to as "(2S,3R,4S)-4HIL"), and to provide a method for manufacturing (2S,3R,4S)-4-hydroxy-L-isoleucine or a salt thereof by direct enzymatic hydroxylation of L-isoleucine using L-isoleucine dioxygenase or a bacterium having the L-isoleucine dioxygenase activity. As a result of extensive research conducted in consideration of the aforementioned problems, the inventors of the present invention isolated from nature a bacterium having a high level of L-isoleucine dioxygenase activity, cloned the gene encoding L-isoleucine dioxygenase, and found that the L-isoleucine dioxygenase may be used in the synthesis of the (2S,3R,4S)-4-hydroxy-L-isoleucine.

Namely, it is an aspect of the present invention to provide L-isoleucine dioxygenase and the DNA encoding L-isoleucine dioxygenase, and a method for producing (2S,3R,4S)-4-hydroxy-L-isoleucine using the L-isoleucine dioxygenase. The above aspects were achieved by finding the novel L-isoleucine dioxygenase.

It is an aspect of the present invention to provide a method for producing 4-hydroxyisoleucine or a salt thereof, comprising A) subjecting isoleucine or a salt thereof to a hydroxylation reaction in the presence of a hydroxylase derived from a microorganism to produce a reaction product, and B) isolating 4-hydroxyisoleucine or a salt thereof from the reaction product.

It is a further aspect of the present invention to provide the method as described above, wherein the microorganism belongs to the genus *Bacillus*.

It is a further aspect of the present invention to provide the method as described above, wherein the microorganism is selected from the group consisting of *Bacillus thuringiensis*, *Bacillus licheniformis*, *Bacillus sphaericus*, *Bacillus cereus*, and *Bacillus weihenstephanensis*.

It is a further aspect of the present invention to provide the method as described above, wherein said hydroxylase is present in a cell lysate prepared from microbial cells which were in a logarithmic growth phase.

It is a further aspect of the present invention to provide the method as described above, wherein L-isoleucine is subjected to hydroxylation.

It is a further aspect of the present invention to provide the method as described above, wherein the hydroxylase is a dioxygenase.

It is a further aspect of the present invention to provide the method as described above, wherein the hydroxylase has the following properties:
(a) requires oxygen, $Fe^{2+}$, ascorbic acid, and 2-oxoglutaric acid as cofactors,
(b) has an optimum reaction pH of 5 to 8,
(c) has an optimum reaction temperature of 45° C. or lower,
(d) is inactivated at 50° C. or higher, and
(e) is inhibited by EDTA, $Cu^{2+}$ and $Zn^{2+}$.

It is a further aspect of the present invention is to provide a dioxygenase which has the following properties and is able to be isolated from a *Bacillus* bacterium:
(a) requires oxygen, $Fe^{2+}$, ascorbic acid, and 2-oxoglutaric acid as cofactors,
(b) has an optimum reaction pH of 5 to 8,
(c) has an optimum reaction temperature of 45° C. or lower,
(d) is inactivated at 50° C. or higher,
(e) is inhibited by EDTA, $Cu^{2+}$ and $Zn^{2+}$.
(f) comprises subunits having a molecular weight of 29,000±2,000 as measured by sodium dodecylsulfate-polyacrylamide gel electrophoresis, and
(g) comprises the amino acid sequence of SEQ ID NO: 5 at the N-terminus.

It is a further aspect of the present invention is to provide the dioxygenase as described above, wherein the *Bacillus* bacterium is *Bacillus thuringiensis*.

It is a further object of the present invention to provide a DNA selected from the group consisting of:
A) a DNA comprising the nucleotide sequence of SEQ ID No:1;
B) a DNA that hybridizes under stringent conditions with a DNA comprising a nucleotide sequence which is complementary to the nucleotide sequence of SEQ ID No: 1, and encodes a protein having L-isoleucine dioxygenase activity;
C) a DNA that encodes a protein comprising the amino acid sequence of SEQ ID No:2;
D) a DNA that encodes a protein having the amino acid sequence of SEQ ID NO: 2, but which includes one or several substitutions, deletions, insertions, additions, or inversions of one or several amino acid residues, and has L-isoleucine dioxygenase activity; and
E) a DNA that encodes a protein comprising an amino acid sequence that is at least 98% homologous to the amino acid sequence of SEQ ID No:2, and has L-isoleucine dioxygenase activity.

It is a further aspect of the present invention to provide a recombinant DNA obtained by ligating the DNA containing the same with a vector DNA.

It is a further aspect of the present invention to provide a cell transformed with the recombinant DNA containing the same.

It is a further aspect of the present invention to provide a process for producing a protein having L-isoleucine dioxygenase activity, the process comprising: A) cultivating the cell containing the same recombinant DNA in a medium, and collecting the protein with L-isoleucine dioxygenase activity from the medium, cells or both.

It is a further aspect of the present invention to provide a protein selected from the group consisting of:
(f) a protein comprising the amino acid sequence of SEQ ID No: 2;
(g) a protein having the amino acid sequence of SEQ ID NO: 2, but which includes one or several substitutions, deletions, insertions, additions, or inversions of one or several amino acids and has L-isoleucine dioxygenase activity; and
(h) a protein that is at least 98% homologous to the amino acid sequence of SEQ ID No: 2 and has L-isoleucine dioxygenase activity.

It is a further object of the present invention to provide a protein comprising:
(A) the ability to catalyze the production of (2S,3R,4S)-4-hydroxy-L-isoleucine by hydroxylation of L-isoleucine;
(B) an activity which is dependent on $Fe^{2+}$; and
(C) a molecular weight per subunit as measured by SDS-PAGE of about 29±2.0 kDa.

It is a further aspect of the present invention to provide a method for manufacturing (2S,3R,4S)-4-hydroxy-L-isoleucine or a salt thereof, the method comprising the steps of:
(A) placing L-isoleucine in an aqueous solvent in the presence of an L-isoleucine dioxygenase selected from the group consisting of:
(a) a protein comprising an amino acid sequence selected from the group consisting of SEQ ID No: 2, 8, 13, 17, and 21,
(b) a protein comprising an amino acid sequence selected from the group consisting of SEQ ID NO: 2, 8, 13, 17, and 21, but which includes one or several substitutions, deletions, insertions, additions, or inversions of one or several amino acids and has L-isoleucine dioxygenase activity,
(c) a protein that is at least 70% homologous to an amino acid sequence selected from the group consisting of SEQ ID No: 2, 8, 13, 17, and 21, and has L-isoleucine dioxygenase activity, and
(d) combinations thereof;
(B) isolating (2S,3R,4S)-4-hydroxy-L-isoleucine from the aqueous solvent.

It is a further aspect of the present invention to provide a method for manufacturing (2S,3R,4S)-4-hydroxy-L-isoleucine or a salt thereof, comprising the steps of:
(A) placing L-isoleucine in an aqueous solvent comprising a bacterial product comprising an L-isoleucine dioxygenase selected from the group consisting of:
(a) a protein comprising an amino acid sequence selected from the group consisting of SEQ ID No: 2, 8, 13, 17, and 21,
(b) a protein comprising an amino acid sequence selected from the group consisting of SEQ ID No: 2, 8, 13, 17, and 21, but which includes one or several substitutions, deletions, insertions, additions, or inversions of one or several amino acids, and has L-isoleucine dioxygenase activity, and
(c) a protein that is at least 70% homologous to an amino acid sequence selected from the group consisting of SEQ ID No: 2, 8, 13, 17, and 21 and has L-isoleucine dioxygenase activity, and
(d) combinations thereof; and
(B) isolating (2S,3R,4S)-4-hydroxy-L-isoleucine from the aqueous solvent.

It is a further aspect of the present invention to provide the method as described above, wherein said activity of the L-isoleucine dioxygenase is enhanced by modifying the bacterium.

It is a further aspect of the present invention to provide the method as described above, wherein the activity of the L-isoleucine dioxygenase is enhanced by increasing the expression of the L-isoleucine dioxygenase.

It is a further aspect of the present invention to provide the method as described above, wherein the expression of the L-isoleucine dioxygenase is increased by a method selected from the group consisting of:

A) modifying an expression control sequence of the gene encoding the L-isoleucine dioxygenase, B) increasing the copy number of the gene encoding the L-isoleucine dioxygenase, and C) combinations thereof.

It is a further aspect of the present invention to provide the method as described above, wherein the bacterium belongs to a genus selected from the group consisting of *Escherichia, Pseudomonas, Corynebacterium, Arthrobacter, Aspergillus* and *Bacillus*.

It is a further aspect of the present invention to provide the method as described above, wherein the bacterium is selected from the group consisting of *Escherichia coli, Arthrobacter simplex, Corynebacterium glutamicum, Arthrobacter globiformis, Arthrobacter sulfureus, Arthrobactor viscosus* and *Bacillus subtilis*.

It is a further object of the present invention to provide the method as described above, wherein the bacterial product is selected from the group consisting of a bacterial culture, cells, treated cells and cell lysate.

BRIEF DESCRIPTION OF THE DRAWINGS

FIG. 14 shows the putative translation start of the *Bacillus thuringiensis* (serovar israelensis, ATCC 35646) RBTH_06809 ORF. The nucleotide sequence is shown in SEQ ID NO:34. The amino acid sequence is shown in SEQ ID NO:35.

In FIG. 15A, the nucleotide sequence is shown in SEQ ID NO:3, and amino acid sequences are shown in SEQ ID NOs: 36-37.

FIG. 17 is a physical map of the pMW119-IDO(Lys, 32) plasmid, and the DNA sequence of the cloned BamHI-SacI fragment containing the IDO structural gene. The nucleotide sequence is shown in SEQ ID NO:45. The amino acid sequence is shown in SEQ ID NO:46.

FIG. 18 shows the DNA alignment of the structural genes corresponding to IDO(Lys, 23), IDO(Lys, 32) and RBTH_6809 (5'-end truncated). Variable positions are marked by shading. The nucleotide sequence of IDO (Lys, RBTH) is shown in SEQ ID NO:47. The nucleotide sequence of IDO (Lys, 23) is shown in SEQ ID NO:49. The nucleotide sequence of IDO (Lys, 32) is shown in SEQ ID NO:7.

FIG. 19 shows the protein alignment of the IDO(Lys, 23), IDO(Lys, 32), and RBTH_068900RF. Variable positions are marked by shading. The amino acid sequence of IDO (Lys, RBTH) is shown in SEQ ID NO:48. The amino acid sequence of IDO (Lys, 23) is shown in SEQ ID NO:2. The amino acid sequence of IDO (Lys, 32) is shown in SEQ ID NO:8.

FIG. 20 shows the protein alignment of IDO from *Bacillus thuringienesis*, BC1061 from *Bacillus cereus*, and the conserved hypothetical protein from *Bacillus weihenstephanensis*. The amino acid sequence of *Bacillus cereus* is shown in SEQ ID NO:50. The amino acid sequence of *Bacillus thuringiensis* is shown in SEQ ID NO:48. The amino acid sequence of *Bacillus weihenstephanensis* is shown in SEQ ID NO:51. The amino acid sequence of Ile hydroxylase is shown in SEQ ID NO:6.

DESCRIPTION OF THE PREFERRED EMBODIMENTS

Figure 1:
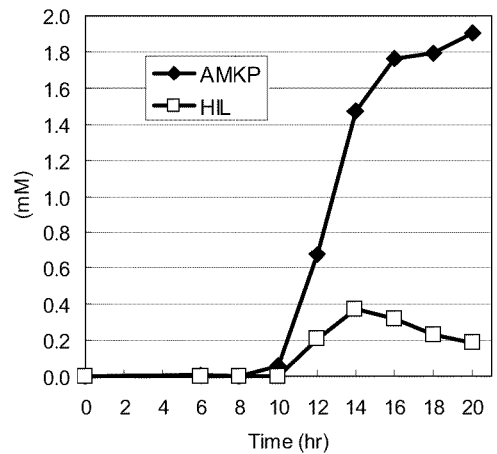
FIG. 1 is a graph which shows the accumulation over time of 4-hydroxyisoleucine and AMKP which are produced in the culture of the 2-e-2 strain.

The name "4-hydroxyisoleucine" may indicate one diasteromer, or a mixture of two or more diastereomers, such as (2S,3S,4S)-4-hydroxyisoleucine, (2S,3R,4R)-4-hydroxyisoleucine, (2S,3S,4R)-4-hydroxyisoleucine, and (2S,3R,4S)-4-hydroxyisoleucine. 4-Hydroxyisoleucine is preferably (2S, 3R,4S)- or (2R,3R,4S)-4-hydroxyisoleucine or a mixture thereof, and more preferably (2S,3R,4S)-4-hydroxyisoleucine.

In particular, the term "(2S,3R,4S)-4-hydroxy-L-isoleucine" or "(2S,3R,4S)-4HIL" may refer to single chemical compound or a mixture containing at least (2S,3R,4S)-4-hydroxyisoleucine.

The term "bacterium" or "microorganism" includes enzyme-producing bacteria or microorganisms, or a mutant or genetic recombinant of such bacteria or microorganisms in which the targeted enzymatic activity is present or has been enhanced, and the like.

<I> Enzymatic Activity which can Catalyze Production of 4HIL from Isoleucine

A hydroxylase is used as the catalyst in the described methods for producing 4-hydroxyisoleucine from isoleucine, and this hydroxylase may be present in a microbial culture, the bacterial cells, or a cell lysate. The hydroxylase may also be in purified form so long as the enzymatic activity of converting isoleucine to 4-hydroxyisoleucine is maintained. Disrupted cells containing crude enzyme, or compositions containing somewhat purified enzyme may also be used.

Examples of the hydroxylase include oxygenases, dioxygenases, and so forth, and dioxygenases are preferred. A hydroxylase that can be isolated from the 2-e-2 bacterial strain and has the following properties is more preferred:

(a) requires oxygen, $Fe^{2+}$, ascorbic acid, and 2-oxoglutaric acid as cofactors,
(b) has an optimum reaction pH of 5 to 8,
(c) has an optimum reaction temperature of 45° C. or lower,
(d) is inactivated at 50° C. or higher, and
(e) is inhibited by EDTA, $Cu^{2+}$ and $Zn^{2+}$.

The hydroxylase from the 2-e-2 strain has the following additional properties:

(f) is made up of subunits having a molecular weight of 29,000±2,000 as measured by sodium dodecylsulfate polyacrylamide gel electrophoresis,
(g) has the amino acid sequence of SEQ ID NO: 5 at the N-terminus.

When the hydroxylase requires a cofactor, it is preferable to add or supply the cofactor to the system. Examples of the cofactor for dioxygenase include, for example, $Fe^{2+}$, ascorbic acid, and 2-ketoglutaric acid. These cofactors may be added or supplied to the system as a salt when possible.

Any microorganism can be used so long as the enzymatic activity which catalyzes the conversion of isoleucine to 4-hydroxyisoleucine under the conditions necessary for hydroxylation is present.

Examples of the microorganism may include microorganisms belonging to the genus *Bacillus* or *Pseudomonas*, mutants or derivatives thereof, and so forth. Furthermore, the microorganism may be one in which the hydroxylase is introduced and expressed by genetic recombination, and which is able to produce 4-hydroxyisoleucine.

Specific examples include *Bacillus thuringiensis* (strains 2-e-2, AKU 238, NBRC 3958, ATCC 35646, etc.), *Bacillus licheniformis* (strains AKU 223, IAM 11054, etc.), *Bacillus sphaericus* (strains AKU 227, NBRC 3526, etc.), *Bacillus cereus* strain ATCC 14579, and *Bacillus weihenstephanensis* strain KBAB4. The 2-e-2 strain (AJ110584) was deposited at the independent administrative agency, National Institute of Advanced Industrial Science and Technology, International Patent Organism Depositary (Tsukuba Central 6, 1-1, Higashi 1-Chome, Tsukuba-shi, Ibaraki-ken, 305-8566, Japan) under the provisions of the Budapest Treaty on Sep. 27, 2006, and given an accession number of FERM BP-10688.

Strains with a name beginning with AKU can be obtained from the Laboratory of Fermentation Physiology and Applied Microbiology, Division of Applied Life Sciences, Graduate School of Agriculture, Kyoto University. Strains with a name beginning with IAM are maintained at the IAM culture collection, Laboratory of Bioresources, Institute of Molecular and Cellular Biosciences, the University of Tokyo, and can be obtained using their registration numbers. The registration numbers corresponding to the strains are listed in the IAM catalog (IAM Catalogue of Strains Third Edition, 2004). Strains with a name beginning with NBRC can be obtained from the independent administrative agency, National Institute of Technology and Evaluation (2-5-8, Kazusa Kamatari, Kisarazu-shi, Chiba, 292-0818). Strains with a name beginning with ATCC can be obtained from the American Type Culture Collection (ATCC) (Postal address: ATCC, P.O. Box 1549, Manassas, Va. 20108, 1, United States of America). *Bacillus weihenstephanensis* strain KBAB4 can be obtained from the Institut National de la Recherche Agronomique (Postal address: Genetique Microbienne, INRA, Domaine de Vilvert, 79352 Jouy en Josas cedex, France).

The *Bacillus thuringiensis* 2-e-2 strain has been newly isolated from the soil in Kyoto, and the scientific properties of this strain are shown below.

Taxonomic properties of *Bacillus thuringiensis* 2-e-2 strain:

1. Phenotype
Cell morphology: *Bacillus* (size: 1.0 to 1.2×2.0 to 3.0 μm)
Gram staining: +
Endospore: +
Attitude to oxygen: Aerobic
Favorable growth at 20 to 35° C.
Optimum pH: pH 7.0 to 7.5

2. Molecular Phylogenetic Analysis Based on the Nucleotide Sequence of the 16S rDNA To determine the 16S rDNA nucleotide sequence of the 2-e-2 strain (SEQ ID NO: 9), searches were conducted on the bacterial strain database (NCIMB Japan, Shizuoka) and several international nucleotide sequence databases (GenBank/DDBJ/EMBL), and BLAST, and the 30 most homologous strains were determined. Then, a molecular phylogenic tree was created using the 16S rDNA nucleotide sequences for the 30 homologous strains retrieved from the bacteria strain database according to the neighbor-joining method. For the homology search and creating a simplified molecular phylogenetic tree, DNAsisPro was used (Hitachi Software Engineering Co., Ltd., Tokyo).

As a result of the homology search of the bacterial strain database and BLAST, a partial nucleotide sequence of the 16S rDNA of the 2-e-2 strain was a 100% match with that of the 16S rDNA of the *Bacillus thuringiensis* ATCC 10792 strain. As a result of the homology search of GenBank/DDBJ/EMBL, the 16S rDNA of the 2-e-2 strain showed a high homology with that of *Bacillus thuringiensis*. Furthermore, the 2-e-2 strain is found on substantially the same phylogenetic branch as that of the 16S rDNA of *Bacillus thuringiensis*, which demonstrates that they are very closely related.

3. Results of Classification and Identification

The 2-e-2 strain appeared to be *Bacillus* bacteria based on the morphological observations, and the analysis of the partial 16S rDNA sequence also showed that the 2-e-2 strain belongs to *Bacillus thuringiensis*. Since no microorganisms have been reported that have AMKP production activity at the same level as the 2-e-2 strain, this strain was identified as a novel strain.

Known and typical culture methods can be used for culturing the microorganisms. Either a natural or synthetic medium may be used for the culture so long as the medium contains a carbon source, nitrogen source, inorganic salts, and so forth that can be assimilated by the microorganism, and the microorganism can be efficiently cultured in the medium.

The carbon source may be one that can be assimilated by the microorganism, and includes saccharides such as glucose, fructose, sucrose, maltose, starch, starch hydrolysate, and molasses, organic acids such as acetic acid, lactic acid, and gluconic acid, and alcohols such as ethanol and propanol. As the nitrogen source, ammonia, ammonium salts of various inorganic acids, and organic acids such as ammonium sulfate, ammonium chloride, ammonium acetate, and ammonium phosphate, other nitrogen-containing compounds, peptone, meat extract, yeast extract, corn steep liquor, casein hydrolysate, soybean meal, soybean meal hydrolysate, various fermenting cells, and digestion products thereof, and so forth can be used so long as the microorganism can assimilate the chosen source.

As the inorganic salts, potassium phosphate, ammonium sulfate, ammonium chloride, sodium chloride, magnesium sulfate, ferrous sulfate, manganese sulfate, and so forth can be used, so long as the chosen microorganism can utilize the chosen salt. In addition, salts of calcium, zinc, boron, copper, cobalt, molybdenum, and so forth may be added as trace elements. Furthermore, vitamins such as thiamin and biotin, amino acids such as glutamic acid and aspartic acid, nucleic acid-related substances such as adenine and guanine, and so forth may be added as required.

The culture is performed under aerobic conditions such as by shaking or deep aeration stirring. The culture temperature is preferably 10 to 37° C., and the culture time is 5 to 40 hours. The pH of the culture is maintained at 5.0 to 9.0 during the culture. The pH is adjusted by using inorganic or organic acids, alkaline solutions, urea, calcium carbonate, ammonia, or the like.

The crude enzyme may be present in disrupted cells, i.e., a microbial cell lysate. The lysate may contain extracellular hydroxylase, and examples of the lysate include bacterial cells treated with surfactant, organic solvent, or enzyme(s), bacterial cells subjected to ultrasonication, mechanical disruption, or a solvent treatment, a fraction of cellular proteins, a solidified product of processed cells, and so forth. The cell lysate is preferably prepared from cells in the logarithmic growth phase.

To prepare a cell lysate, cultured bacterial cells can be washed with an isotonic solution such as physiological saline, and then disrupted by any means, for example, by compression disruption using a French press, glass beads, ultrasonic disruptor, Manton Gaulin homogenizer, mortar, a combination thereof, or the like. For more efficient cell disruption, cell membrane surfaces may be physically or chemically treated by freezing, treated with enzymes, or the like. During the cell disruption, cells are always maintained at a low temperature, and when the cell lysis temperature is raised due to the disruption process, the temperature may be immediately lowered.

Examples of aqueous medium which may be used for the cell lysate include, but are not limited to, water and buffers such as those of borate, acetate, carbonate, Tris, phosphate, citrate, and Good buffer. Furthermore, glycerol, DTT or the like may be added as an enzyme stabilizer, and EDTA, EGTA, PMSF, pepstatin, E-64 or the like may be added as a protease inhibitor. A combination of inhibitors, an inhibitor cocktail, or the like may also be added.

When using a cell lysate in the production of 4-hydroxyisoleucine, the composition of the substrate solution may be 100 mM HEPES buffer (pH 7.0) containing 5 mM isoleucine, 5 mM 2-ketoglutaric acid, 5 mM ascorbic acid, and 5 mM Fe in a volume of 100 µl, and the reaction is performed at 30° C. for 60 minutes. Other than the HEPES buffer, other buffers such as MES buffer and GTA wide range buffer may also be used. After the required enzyme inactivation, the centrifugation supernatant fraction solution is filtered, and production of 4-hydroxyisoleucine is measured by high performance liquid chromatography or TLC.

4-Hydroxyisoleucine may be quantified by any method so long as the chosen analysis system can separate 4-hydroxyisoleucine from other components, and examples include TLC and high performance liquid chromatography. High performance liquid chromatography is preferred for quantitative analysis because of its high sensitivity and superior separating ability. Examples include the Waters AccQ-Tag™ method, which is an amino acid analysis method, and so forth. By a modified Waters AccQ-Tag™ method (see the examples described later), diastereomers of 4-hydroxyisoleucine can be separated, and naturally occurring 4-hydroxyisoleucine and 2-amino-3-methyl-4-ketopentanoic acid, which is a keto compound formed by oxidation of the hydroxyl group of 4-hydroxyisoleucine, can be separated.

4-Hydroxyisoleucine can be isolated by using any common amino acid purification method. For example, by using a combination of an ion exchange resin, a membrane, crystallization, and so forth, 4-hydroxyisoleucine can be isolated from the supernatant after solids are removed by centrifugation.

The pH for the isoleucine hydroxylation reaction is preferably 5 to 8. Factors which are essential for the enzymatic reaction are preferably present in the reaction mixture. When Fe is essential, a reaction mixture composition should be used which is unlikely to cause chelation with the $Fe^{2+}$, such as HEPES buffer, MES buffer, and GTA wide range buffer. However, the reaction mixture composition is not limited so long as the action of $Fe^{2+}$ is maintained.

The temperature for the hydroxylation reaction of isoleucine is usually 15 to 30° C., preferably 45° C. or lower. The reaction time is usually 5 minutes to 200 hours, although it varies depending on the amount of the enzyme.

The L-isoleucine form is preferably used in the hydroxylation reaction.

Examples of the solvent in which the reaction can be performed include aqueous solvents, for example, water, buffers such as carbonate, acetate, borate, citrate and Tris, organic solvents, for example, alcohols such as methanol and ethanol, esters such as ethyl acetate, ketones such as acetone, amides such as acetamide, aqueous solvents containing these organic solvents, and so forth. Furthermore, a factor for activating the hydroxylation reaction may be added as required.

The protein concentration of the cell lysate is 0.1 to 50 mg/ml, preferably 0.5 to 20 mg/ml (in terms of cell weight (wet weight)). 4-Hydroxy-L-isoleucine can be produced by adding the cell lysate, substrate, and cofactors to an aqueous medium at suitable concentrations and allowing the reaction to proceed at a temperature of 45° C. or lower, preferably 30° C., and pH 5 to 12, preferably pH 5 to 7.5, for 5 minutes to 120 hours.

<II> L-Isoleucine Dioxygenase and DNA Encoding the L-Isoleucine Dioxygenase, and their Uses The following is a detailed explanation of [I] L-isoleucine dioxygenase, and [II] a process for producing (2S,3R,4S)-4-hydroxy-L-isoleucine using L-isoleucine dioxygenase with reference to the accompanying drawings.

[I] L-Isoleucine dioxygenase

Within the *Bacillus* genus, bacterial strains were found which contained L-isoleucine dioxygenase, and which were able to form (2S,3R,4S)-4HIL. L-Isoleucine dioxygenase is also referred to as "IDO".

As described above, the unique microbe *Bacillus thuringiensis* strain 2-e-2 was found by screening environmental microorganisms. This strain is able to catalyze the reaction in which (2S,3R,4S)-4HIL is directly formed from L-isoleucine. The term "L-isoleucine" refers to both the free form and the salt form. The novel L-isoleucine dioxygenase was purified and isolated from the cultivated microbial cells, and is hereinafter abbreviated as "IDO(Lys,23)".

Furthermore, the N-terminal amino acid sequence of IDO (Lys,23) was determined by purifying the dioxygenase from *Bacillus thuringiensis* 2-e-2 strain. *Bacillus thuringiensis* 2-e-2 was named *Bacillus thuringiensis* AJ110584 and deposited at the International Patent Organism Depositary, National Institute of Advanced Industrial Science and Technology (Central 6, 1-1-1 Higashi, Tsukuba, Ibaraki 305-8566, Japan) on Sep. 27, 2006 and given an accession number of FERM BP-10688 under the provisions of Budapest Treaty.

Furthermore, DNA molecules of about 30 base pairs deduced from the amino acid sequences of the IDO(Lys,23) were synthesized. Then, the entire length of the DNA that encodes IDO(Lys,23) was isolated using chromosomal DNA from *Bacillus thuringiensis* strain 2-e-2. The L-isoleucine dioxygenase from *Bacillus thuringiensis* (serovar israelensis) strain (ATCC 35646), "IDO(Lys,32)", was used as the control. These DNA molecules were used to construct recombinant plasmids and transform *E. coli* cells. Subsequent analysis of the recombinant *E. coli* IDO activity revealed a much higher (5 times) activity of IDO(Lys,23) in comparison with IDO(Lys,32). It appears that this difference in activity is due to the unique mutations present in the IDO(Lys,23) gene from *Bacillus thuringiensis* strain 2-e-2.

The DNA encoding IDO(Lys,23) is shown in SEQ ID No: 1. Furthermore, the amino acid sequence of IDO(Lys,23) encoded by the nucleotide sequence of SEQ ID NO: 1 is shown in SEQ ID No: 2. IDO(Lys,23) of SEQ ID NO: 2 possesses the L-isoleucine dioxygenase activity, and catalyzes the reaction in which (2S,3R,4S)-4HIL shown in the following formula (I) is directly synthesized from one molecule of L-isoleucine.

(I)

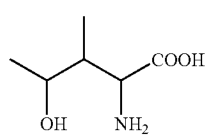

Next, a detailed explanation is provided of (1) a DNA encoding L-isoleucine dioxygenase, (2) properties of L-isoleucine dioxygenase, and (3) a process for producing L-isoleucine dioxygenase.

(1) A DNA Encoding L-Isoleucine Dioxygenase

The IDO(Lys,23) gene having the nucleotide sequence of SEQ ID No: 1 was isolated from the chromosomal DNA of *Bacillus thuringiensis* 2-e-2 as described in the Examples section. The nucleotide sequence of SEQ ID No: 1 from *Bacillus thuringiensis* 2-e-2 encoding IDO(Lys,23) demonstrates the high level of homology both at the nucleotide (FIG. 19) and amino acid levels (FIG. 18) with the non-annotated part of the genomic nucleotide sequence from *Bacillus thuringiensis* (serovar israelensis) (ATCC 35646), one copy of which was submitted 17 Jan. 2007 to the National Center for Biotechnology Information, NIH, Bethesda, Md. 20894, USA (Accession No: AAJM00000000.1, GI:74494335), and the other was obtained as a result of sequencing the genomic DNA encoding IDO(Lys,32) of the same *Bacillus thuringiensis* (serovar israelensis) strain received from Russian National Collection of Industrial Microorganisms (VKPM) stored under accession number VKPM B-197. The nucleotide sequence from *Bacillus thuringiensis* (serovar israelensis) strain VKPM B-197 encoding IDO(Lys,32) is shown as SEQ ID NO: 7.

The following is an explanation of the method for obtaining the amino acid sequence of IDO from IDO-producing bacteria.

The major protein was recovered from a gel and identified by MS-analysis as a putative RBTH_06809 protein from *Bacillus thuringiensis* (serovar israelensis) ATCC 35646 strain (FIG. 13).

Mass spectrometry analysis of the protein sample extracted from SDS-PAGE was conducted. The treatment of gels, trypsinolysis, protein extraction, and mass analysis by time-of-flight matrix-assisted laser desorption-ionization (MALDI-TOF) were conducted according to the protocols described by Govorun, V. M. et al (The proteome comparative analysis of *Helicobacter pylori* clinical isolates. Biochemistry (Rus), 68, 42-49 (2003)). The protein was identified by the set of its photolytic peptide masses using the Peptide Fingerprint option of Mascot software (Matrix Science, USA). The DNA fragment coding for IDO can be obtained by PCR using appropriate primers designed based on the sequence from *Bacillus thuringiensis* (serovar israelensis) (ATCC 35646).

The procedure employed for PCR is described in publications such as White, T. J. et al., Trends Genet. 5, 185 (1989). The methods for isolating the chromosomal DNA, as well as the methods for isolating a desired DNA molecule from a gene library using a DNA molecule as a probe, are described in publications such as Molecular Cloning, 3rd edition, Cold Spring Harbor Laboratory Press (2001).

A method for determining the nucleotide sequence of the isolated DNA that encodes IDO is described in A Practical Guide to Molecular Cloning, John Wiley & Sons, Inc. (1985). Furthermore, the nucleotide sequence may be determined by using the DNA Sequencer made by Applied Biosystems. The DNA encoding IDO(Lys,23) derived from *Bacillus thuringiensis* strain 2-e-2 is shown in SEQ ID No: 1. The nucleotide sequence from *Bacillus thuringiensis* (serovar israelensis) strain VKPM B-197 that encodes IDO(Lys,32) is shown in SEQ ID No: 7.

The DNA that encodes IDO is not only the DNA shown in SEQ ID No: 1, but also includes functional variants of this sequence. This is because there are often differences in nucleotide sequences of the same function among various species and strains within the *Bacillus* genera. Such functional variants will still encode an IDO protein which catalyzes the production of (2S,3R,4S)-4HIL from L-isoleucine.

The DNA encoding IDO may also include mutations which have been artificially introduced as long as the mutated DNA still encodes IDO that has the activity of catalyzing the production of (2S,3R,4S)-4HIL from L-isoleucine. Methods for artificially adding mutations include commonly known methods such as by introducing site-specific mutations as described in Method. in Enzymol., 154 (1987).

The DNA also includes DNA that hybridizes under stringent conditions with a nucleotide sequence complementary to the nucleotide sequence of SEQ ID No: 1, and encodes a protein having IDO activity. As used herein, the "stringent conditions" refer to conditions under which a specific hybrid is formed and a non-specific hybrid is not formed. Although it is difficult to numerically explicitly express these conditions, by way of example, conditions under which DNA molecules having higher homology e.g. preferably 70% or more, more preferably 80% or more, still more preferably 90% or more, and particularly preferably 95% or more, hybridize with each other, while DNA molecules having lower homology do not hybridize with each other. Stringent conditions can also be defined as when hybridization occurs with typical washing conditions in Southern hybridization, that is, at a salt concentration corresponding to 0.1×SSC and 0.1% SDS at 37° C., preferably 0.1×SSC and 0.1% SDS at 60° C., and more preferably 0.1×SSC and 0.1% SDS at 65° C. The length of the probe may be suitably selected, depending on the hybridization conditions, and usually varies from 100 bp to 1 kbp. Furthermore, "L-isoleucine dioxygenase activity" means the activity that results in the synthesis of (2S,3R,4S)-4HIL from L-isoleucine. However, when a nucleotide sequence hybridizes under stringent conditions with a nucleotide sequence complementary to the nucleotide sequence of SEQ ID No: 1, L-isoleucine dioxygenase activity is retained at least 10% or more, preferably 30% or more, more preferably 50% or more, and still more preferably 70% or more, of the protein having the amino acid sequence of SEQ ID No: 2, at 37° C. and pH 8.

Furthermore, the DNA may include a DNA encoding a protein which is substantially identical to the IDO encoded by the DNA of SEQ ID No: 1. Namely, this may include the following DNAs:

(a) a DNA of the nucleotide sequence of SEQ ID No: 1;

(b) a DNA that hybridizes under stringent conditions with a DNA having a nucleotide sequence complementary to the nucleotide sequence of SEQ ID No: 1, and encodes a protein having L-isoleucine dioxygenase activity;

(c) a DNA that encodes a protein of the amino acid sequence of SEQ ID No: 2;

(d) a DNA that encodes a protein having the amino acid sequence of SEQ ID NO: 2, but which includes substitutions, deletions, insertions, additions, or inversions of one or several amino acids, and has L-isoleucine dioxygenase activity; and (e) a DNA that encodes a protein having an amino acid sequence that is at least 70% homologous, preferably at least 80% homologous, more preferably at least 90% homologous, and still more preferably at least 95% homologous to the amino acid sequence of SEQ ID NO:2, and which has the L-isoleucine dioxygenase activity.

Here, "one or several" refers to the range over which the 3D structure of the protein having L-isoleucine dioxygenase activity is not significantly impaired, and more specifically, a range of 1 to 78, preferably 1 to 52, more preferably 1 to 26, and still more preferably 1 to 13.

The substitution, deletion, insertion, addition, or inversion of one or several amino acid residues should be conservative mutation(s) so that the activity is maintained. The representative conservative mutation is a conservative substitution. Examples of conservative substitutions include substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val.

Furthermore, "L-isoleucine dioxygenase activity" refers to the activity that results in the synthesis of (2S,3R,4S)-4HIL from L-isoleucine as described above. However, when the amino acid sequence contains one or more substitutions, deletions, insertions, additions, or inversions of one or several amino acid residues, the protein should retain at least 10% or more, preferably 30% or more, more preferably 50% or more, and still more preferably 70% or more L-isoleucine dioxygenase activity as compared to the protein having the exact amino acid sequence of SEQ ID No: 2, at 30° C. and pH 6.0. The L-isoleucine dioxygenase activity of the IDO can be measured by analysis of (2S,3R,4S)-4HIL formation from L-isoleucine using high-performance liquid chromatography (HPLC).

Furthermore, a homologue DNA of SEQ ID NO: 1 can also be used. Whether the homologue DNA encodes L-isoleucine dioxygenase or not can be confirmed by measuring L-isoleucine dioxygenase activity of the cell lysate, or cell lysate of the microorganism in which the homologue DNA is overexpressed.

The homologue DNA of SEQ ID NO: 1 can also be prepared from the genome of another *Bacillus* species, for example, *Bacillus cereus* or *Bacillus weihenstephanensis*.

The alignment of the amino acid sequences of *Bacillus cereus, Bacillus thuringiensis, Bacillus weihenstephanensis* is shown in FIG. 20, and the conserved sequence among the species of the genus *Bacillus* is shown in SEQ ID NO: 6.

Furthermore, DNA homologues of genes encoding IDO from other species and genus of bacteria can be obtained by cloning, based on homologies to the following-listed genes (Table. 1) from *Bacillus, Escherichia, Corynebacterium, Arthrobacter, Aspergillus, Pseudomonas, Granulibacter, Methylobacillus, Granulibacter, Acidiphilium, Agrobacterium, Gluconobacter, Caulobacter, Stigmatella, Myxococcus, Polaromonas, Caulobacter, Polaromonas, Sphingomonas, Acidovorax, Mycobacterium, Azotobacter, Vibrio, Polynucleobacter, Streptomyces*, or the like. The homologues may be amplified by PCR using, for example, the synthetic oligonucleotides shown in SEQ ID NOS: 3 and 4.

TABLE 1

List of putative DNA encoding L-isoleucine dioxygenase

| Gene | Microorganism | Description | Genbank Accession No. |
|---|---|---|---|
| RBTH_06809 | *Bacillus thuringiensis* serovar israelensis ATCC 35646 | Hypothetical protein RBTH_06809 | AAJM01000012.1 GI: 75758796 |
| BC1061 | *Bacillus cereus* ATCC 14579 | hypothetical protein | NC_004722.1 GI: 30019216 |
| — | *Bacillus weihenstephanensis* KBAB4 | conserved hypothetical protein | ZP_01182590.1| GI: 89204011 |
| PSPPH_3986 | *Pseudomonas syringae* pv. phaseolicola 1448A | hypothetical protein | NC_005773.3 GI: 71735316 |
| GbCGDNIH1 2096 | *Granulibacter bethesdensis* CGDNIH1 | hypothetical protein | NC_008343.1 GI: 114328760 |
| Mfla_2629 | *Methylobacillus flagellatus* KT | hypothetical protein | NC_007947.1 GI: 91776977 |
| GbCGDNIH1_2096 | *Granulibacter bethesdensis* CGDNIH1 | hypothetical protein | NC_008343.1 GI: 114328760 |
| — | *Acidiphilium cryptum* JF-5 | conserved hypothetical protein | ZP_01144511.1 GI: I88939060 |
| — | *Agrobacterium vitis* | hypothetical protein | ABG82019.1 GI: 110671820 |

TABLE 1-continued

List of putative DNA encoding L-isoleucine dioxygenase

| Gene | Microorganism | Description | Genbank Accession No. |
|---|---|---|---|
| GOX1674 | *Gluconobacter oxydans* 621H | hypothetical protein | YP: 192070.1 GI: 58040106 |
| — | *Caulobacter* sp. K31 | conserved hypothetical protein | ZP: 01420729.1 GI: 113934829 |
| — | *Stigmatella aurantiaca* DW4/3-1 | conserved hypothetical protein | ZP_01462001.1 GI: 115374724 |
| MXAN_6813 | *Myxococcus xanthus* DK 1622 | hypothetical protein | YP: 634930. GI: 108759113 |
| Bpro_0594 | *Polaromonas* sp. JS666 | hypothetical protein | YP: 547452.1 GI: 91786500 |
| CC3057 | *Caulobacter crescentus* CB1 | hypothetical protein | NP_421851.1 GI: 16127287 |
| — | *Polaromonas naphthalenivorans* CJ2 | similar to Uncharacterized protein conserved in bacteria | ZP_01022090.1 GI: 84714798 |
| — | *Sphingomonas* sp. SKA58 | putative phage repressor | ZP_01302473 GI: 94495894 |
| — | *Acidovorax* sp. JS42 | conserved hypothetical protein | ZP_01384166.1 GI: 110595841 |
| — | *Mycobacterium* sp. JLS | conserved hypothetical protein | ZP_01276363.1 GI: 92907583 |
| — | *Azotobacter vinelandii* AvOP | similar to Uncharacterized protein conserved in bacteria | ZP_00417642.1 GI 67156016 |
| VV21380 | *Vibrio vulnificus* CMCP6 | hypothetical protein | NP_763273.1 GI 27367746 |
| VVA0217 | *Vibrio vulnificus* YJ016 | hypothetical protein | NP_936273.1 GI 37675877 |
| — | *Polynucleobacter* sp. QLW-P1DMWA-1 | conserved hypothetical protein | ZP_01493168.1 GI 116268923 |
| AF484556_24 | *Streptomyces atroolivaceus* | conserved hypothetical protein | AAN85502.1 GI: 26541515 |

(2) Properties of IDO

Next, an explanation is provided of the properties of purified L-isoleucine dioxygenase derived from *Bacillus thuringiensis* strain 2-e-2 (IDO(Lys,23)).

The IDO(Lys,23) has the amino acid sequence of SEQ ID No: 2 as was clearly determined by the previously described gene isolation and analysis. However, other proteins may also have the IDO activity, but the amino acid sequence may contain one or several substitutions, deletions, insertions, additions, or inversions of amino acid(s) as compared to the amino acid sequences shown in SEQ ID No: 2, 8, 13, 17, or 21.

Namely, the IDO includes the following proteins:

(f) a protein having the amino acid sequences of SEQ ID No: 2, 8, 13, 17, or 21;

(g) a protein having the amino acid sequences of SEQ ID No: 2, 8, 13, 17, or 21, but which contains one or more substitutions, deletions, insertions, additions, or inversions of amino acid(s), and has L-isoleucine dioxygenase activity; and (h) a protein that is at least 70% homologous, preferably at least 80% homologous, more preferably at least 90% homologous and still more preferably at least 95% homologous to the amino acid sequence of SEQ ID NO: 2, 8, 13, 17, or 21 and has L-isoleucine dioxygenase activity.

Here, the definitions of "several" and "L-isoleucine dioxygenase activity" are the same as defined in section (1), DNA Encoding L-isoleucine dioxygenase.

The IDO catalyzes the reaction that results in synthesis of (2S,3R,4S)-4HIL by hydroxylation from L-isoleucine.

The L-isoleucine dioxygenase activity of the IDO may be measured by analysis of (2S,3R,4S)-4HIL formation from L-isoleucine using high-performance liquid chromatography (HPLC).

The IDO is able to catalyze the reaction that results in synthesis of (2S,3R,4S)-4HIL by hydroxylation from L-isoleucine. In the hydroxylation reaction catalyzed by dioxygenases, one atom of molecular oxygen is incorporated into L-isoleucine, while the other oxygen atom is incorporated in another oxygen acceptor, for example, α-ketoglutarate, resulting in the formation of (2S,3R,4S)-4HIL and succinate with the release of carbon dioxide. Dioxygenases are capable of hydroxylating an aliphatic carbon chain in a stereospecific way. One plant enzyme has been reported which is capable of catalyzing a hydroxylation reaction of L-isoleucine, and that is the L-isoleucine dioxygenase derived from fenugreek extract (Phytochemistry, Vol. 44, No. 4, pp. 563-566, 1997). However, this method is unsatisfactory for manufacturing 4-hydroxy-L-isoleucine because the activity of the enzyme is inhibited by isoleucine at concentrations of 20 mM and above, the enzyme has not been identified, the enzyme is derived from plant extracts and is not readily obtained in large quantities, and the enzyme is unstable.

Next, the following provides a description of the enzymatic properties investigated for purified IDO(Lys,23).

IDO(Lys,23) catalyzes the reaction that forms (2S,3R,4S)-4HIL represented by the following general formula (I):

(I)

from L-isoleucine in the reaction shown below:

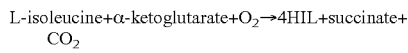
L-isoleucine+α-ketoglutarate+$O_2$→4HIL+succinate+ $CO_2$

Thus, a process of producing (2S,3R,4S)-4HIL from L-isoleucine by using IDO(Lys,23) is also described.

Furthermore, the activity of IDO(Lys,23) strictly depends on the bivalent cation $Fe^{2+}$ and is completely blocked in the presence of EDTA. IDO(Lys,23) is able to catalyze the transfer of one oxygen atom to L-isoleucine and another oxygen atom to GL-ketoglutarate. So, IDO(Lys,23) may be an α-ketoglutamate-dependent dioxygenase.

The molecular weight of each IDO (Lys,23) subunit as measured by SDS-PAGE is about 29±2.0 kDa. Therefore, IDO includes proteins defined by the following characteristics:

(A) an activity that catalyzes production of (2S,3R,4S)-4HIL from L-isoleucine and α-ketoglutarate;

(B) the activity is dependent on a bivalent cation such as $Fe^{2+}$, and (C) the molecular weight per subunit as measured by SDS-PAGE is about 29±2.0 kDa.

The IDO(Lys,32) from *Bacillus thuringiensis* (serovar israelensis) strain VKPM B-197 has the amino acid sequence of SEQ ID NO: 8.

(3) Process for Producing L-Isoleucine Dioxygenase

Next, an explanation is provided for the process of producing the IDO. There are two ways to produce IDO. These are (i) cultivating an IDO-producing microorganism to produce and accumulate IDO, and (ii) preparing a transformant to produce IDO by a recombinant DNA technology and cultivating the transformant to produce IDO.

(i) Process for Forming and Producing IDO by Microbial Cultivation

Examples of microorganisms which can produce IDO by cultivation include microorganisms belonging to the genus *Escherichia, Pseudomonas, Corynebacterium, Arthrobacter, Aspergillus,* or *Bacillus*.

Any microorganism belonging to the genus *Bacillus, Escherichia, Corynebacterium, Arthrobacter, Aspergillus, Pseudomonas, Granulibacter, Methylobacillus, Granulibacter, Acidiphilium, Agrobacterium, Gluconobacter, Caulobacter, Stigmatella, Myxococcus, Polaromonas, Caulobacter, Polaromonas, Sphingomonas, Acidovorax, Mycobacterium, Azotobacter, Vibrio, Polynucleobacter, Streptomyces* may be used provided they are microorganisms that produce the IDO which catalyzes the synthesis of (2S,3R,4S)-4HIL from L-isoleucine and α-ketoglutarate. Preferable microorganisms include *Bacillus thuringiensis* strain 2-e-2 and *Bacillus thuringiensis* (serovar israelensis; ATCC 35646) strain. Among these, *Bacillus thuringiensis* strain 2-e-2 is particularly preferable.

Although the microorganism may be cultivated by any method, such as liquid or solid cultivation, an industrially advantageous method is by conducting deep-aerated stir cultivation. Carbon sources, nitrogen sources, inorganic salts, and other trace nutrient elements commonly used in microbial cultivation may be used. The chosen nutrient sources should be appropriate for the chosen microorganism.

Culturing is conducted under aerobic conditions by shake-culturing, deep ventilation stir-culturing, or the like. The cultivation temperature may be within a range in which the microorganisms will grow and IDO is produced. Thus, although the conditions are not strictly set forth, the cultivating temperature is typically 10 to 50° C. and preferably 15 to 42° C. The cultivating time varies according to the other cultivating conditions. For example, the microorganisms may be cultivated until the largest amount of IDO is produced, and this is typically about 5 hours to 7 days, and preferably about 10 hours to 96 hours.

Following cultivation, the microbial cells are recovered by centrifugation (e.g., 10,000×g for 10 minutes). Since the majority of the IDO is present in the cells, the IDO is solubilized by disrupting or lysing the microbial cells. Disruption of the cells may be accomplished by ultrasonic means, a French press, or glass beads. When lysing the cells, an egg white lysozyme, peptidase treatment, or a suitable combination of these may be used.

When IDO is purified from the microorganism using an enzyme solubilizing solution and undisrupted or unlysed residue remains, re-centrifuging the solubilization solution and removing any residue that precipitates is advantageous to purification.

All commonly used methods for purifying ordinary enzymes may be employed to purify the IDO, examples of which include ammonium sulfate precipitation, gel filtration chromatography, ion exchange chromatography, hydrophobic interaction chromatography and hydroxyapatite chromatography. As a result, an IDO-containing fraction with higher specific activity may be obtained.

(ii) Production Process Using Recombinant DNA Technology

Next, a process for producing IDO using recombinant DNA technology is described. There are numerous known examples of producing useful proteins such as enzymes and physiologically active substances using recombinant DNA technology. The use of recombinant DNA technology enables mass production of useful proteins which are present in trace amounts in nature.

Figure 11:
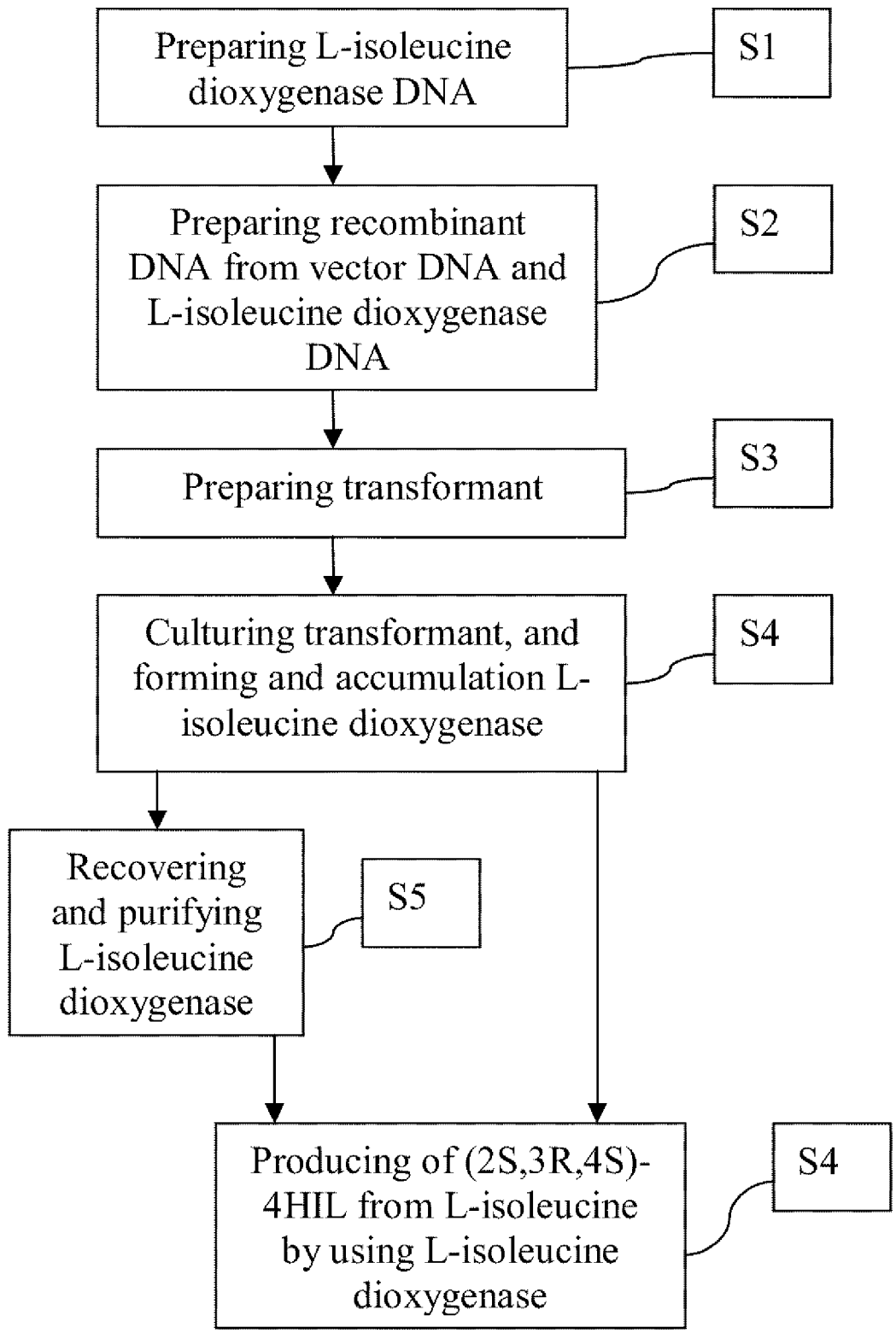
FIG. 11 is a flowchart of the process for producing IDO.
Figure 12:
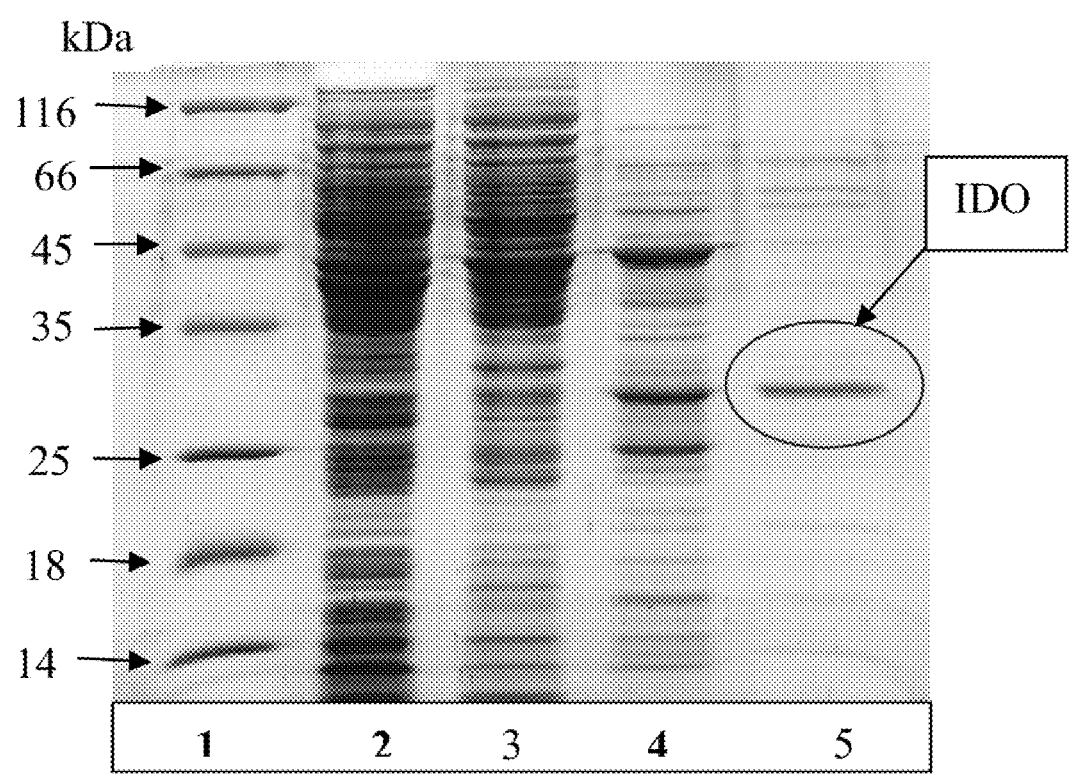
FIG. 12 is a photograph of the SDS-PAGE gel. The lanes represent the protein preparation at the various stages of IDO purification from *Bacillus*. Lanes: 1—molecular weight standards; 2—crude cell lysate; 3—ammonium sulphate precipitation; 4—SEC; 5—AEC.
Figure 13:
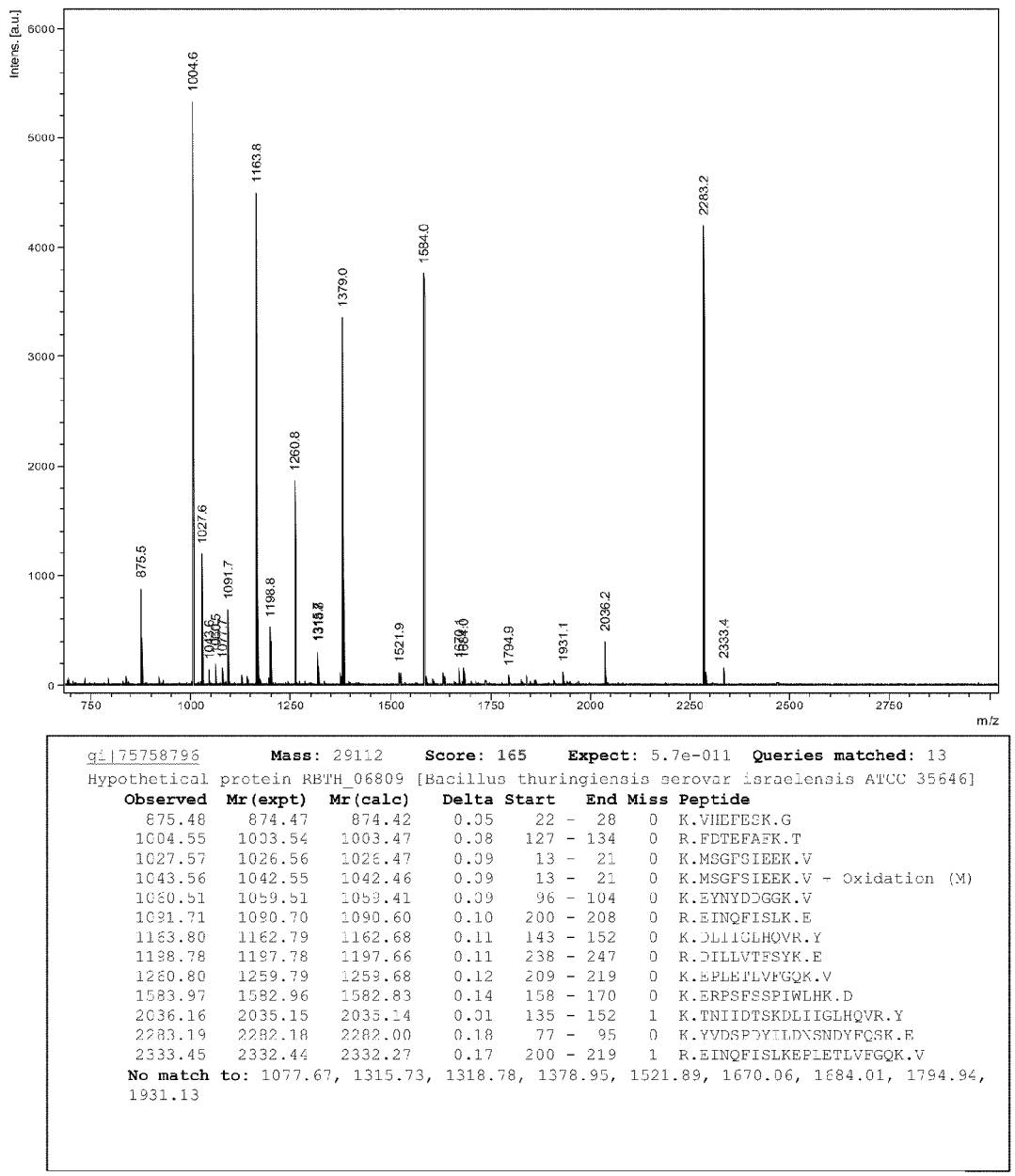
FIG. 13 shows the MS-identification of IDO from *Bacillus thuringiensis* 2-e-2. Peptide sequences in the far right column of the box are listed in, in order, SEQ ID NOs:22-33.

FIG. 11 is a flowchart of the process for producing the IDO.

First, a DNA is prepared that encodes IDO (Step S1).

Next, the prepared DNA is ligated with a vector DNA to produce a recombinant DNA (Step S2), and cells are transformed with the recombinant DNA to produce a transformant (Step S3). Then, the transformant is cultivated in a medium, and the IDO is produced and accumulates in the medium, the cells, or both (Step S4).

Subsequently, the process proceeds to Step S5 where IDO is recovered and purified.

The desired (2S,3R,4S)-4HIL may be produced in a large amount by using the purified IDO produced at Step S5, or the medium, cells, or both in which IDO has accumulated from Step S4 in the hydroxylation reaction (Step S6).

The DNA that is ligated with the vector DNA may allow expression of the IDO.

Here, examples of IDO genes ligated into the vector DNA include the previously described DNA as described in [I].

For large scale protein production using recombinant DNA technology, host cells such as bacterial cells, *Actinomyces* cells, yeast cells, mold cells, plant cells, and animal cells may be transformed. Examples of bacterial cells for which host-vector systems have been developed include *Escherichia, Pseudomonas, Corynebacterium, Arthrobacter, Aspergillus,* and *Bacillus*, and preferably *Escherichia coli* or *Corynebacterium glutamicum* is used. This is because there is a large volume of knowledge regarding technologies for mass production of protein using *Escherichia coli, Corynebacterium glutamicum,* and *Bacillus* bacteria. The following describes a process for producing L-isoleucine dioxygenase using transformed *E. coli*. The following method for *E. coli* can also be applied to *Corynebacterium glutamicum* and *Bacillus* bacteria.

Promoters typically employed in heterogeneous protein production in *E. coli* may be chosen to express the DNA encoding IDO, examples of which include known strong promoters such as T7 promoter, trp promoter, lac promoter, tac promoter, and PL promoter.

In order to produce IDO as a fused protein inclusion body, a gene that encodes another protein, preferably a hydrophilic peptide, is ligated either upstream or downstream of the IDO gene. The gene that encodes the other protein may be a gene that increases the amount of fused protein which accumulates and thereby enhances the solubility of the fused protein following the denaturation and regeneration steps. Examples of candidates include the T7 gene 10, β-galactosidase gene, dehydrofolate reductase gene, interferon-γ gene, interleukin-2 gene, and prochymosin gene.

When ligating these genes with a gene that encodes IDO, the codon reading frames should be placed in frame. The genes may either be ligated into a suitable restriction enzyme site or synthetic DNA of an appropriate sequence may be used.

In order to increase the amount produced, it is preferable to couple a transcription termination sequence downstream from the fused protein gene. Examples of such a transcription terminator sequence include the T7 terminator, fd phage terminator, T4 terminator, tetracycline resistance gene terminator, and *E. coli* trpA gene terminator.

Multi-copy vectors are preferable for introducing the gene that encodes IDO or a fused protein of IDO into *E. coli*, examples of which include plasmids having a replication starting point derived from Col E1 such as pUC plasmids, pBR322 plasmids, or their derivatives. A "derivative" refers to a plasmid in which base substitution, deletion, insertion, addition, or inversion has occurred. Such changes may be caused by a mutagen, UV irradiation, or by spontaneous or random mutation.

The vector may have a marker such as the ampicillin resistance gene so that transformants may be selected. Examples of such vectors include commercially available expression vectors which include a powerful promoter (such as pUC (Takara), pPROK (Clontech), and pKK233-2 (Clontech)).

Recombinant DNA may be obtained by ligating a DNA fragment containing a promoter, a gene encoding IDO or a fused protein of IDO and another protein, and a terminator are ligated in that order, with a vector DNA.

When *E. coli* is transformed using the recombinant DNA and then cultivated, IDO or the fused protein is expressed and produced. Strains that are typically used to express heterogeneous genes may be used as the transformed host, and *E. coli* strain JM109 (DE3) and *E. coli* strain JM109 are particularly preferable. The transformation method and method for selecting the transformant are described in, for example, Molecular Cloning, 3rd edition, Cold Spring Harbor Laboratory Press (2001).

When expressing the fused protein, the IDO may be cut out using a restricting protease such as blood coagulation factor Xa or kallikrein that recognizes sequences which are not present in IDO.

A medium which is typically used to cultivate *E. coli* may be used, examples of which include M9-casamino acid medium and LB medium. Furthermore, the cultivation and production conditions may be appropriately selected according to the type of the marker and promoter on the chosen vector, and the chosen host microorganism.

The following method may be used to recover the IDO or fused protein. If the IDO or fused protein is solubilized within microbial cells, then the disrupted or lysed microbial cells may be used as a crude enzyme solution. In addition, the IDO or its fused protein may also be further purified by precipitation, filtration, column chromatography, or other common techniques as necessary. An antibody may also be used to purify the IDO or fused protein.

When a protein inclusion body is formed, it may be solubilized with a denaturant. Although the protein inclusion body may be solubilized with microbial cell protein, in consideration of the subsequent purification procedure, it is preferable to remove the inclusion body and then solubilize it. A known method may be used to recover the inclusion body from the microbial cell. For example, the inclusion body may be recovered by disrupting the microbial cell followed by centrifugation. Examples of denaturants that solubilize protein inclusion bodies include guanidine hydrochloride (e.g., 6 M, pH 5-8) and urea (e.g., 8 M).

The protein inclusion body may be regenerated as an active protein by removing these denaturants by dialysis, for example. Dialysis solutions such as Tris-HCl buffer or phosphate buffer may be used for dialysis, and the concentration may be from 20 mM to 0.5 M, and the pH may be from pH 5 to pH 8.

The protein concentration during the regeneration step is preferably maintained at about 500 μg/ml or less. In order to prevent the regenerated IDO from self-crosslinking, the dialysis temperature is preferably 5° C. or lower. Furthermore, restoration of activity may also be accomplished by removing the denaturant by dilution and/or ultrafiltration in addition to the dialysis.

When the IDO gene is derived from bacteria belonging to the genus *Bacillus*, the IDO may be expressed and produced in host bacteria of *Escherichia, Pseudomonas, Corynebacterium, Arthrobacter, Aspergillus*, or *Bacillus*.

The copy number of the gene may be increased by inserting the gene into a multi-copy vector, followed by introducing the vector into a microorganism. Multi-copy vectors include *E. coli* plasmid vectors such as pMW118, pBR322, pUC19, pBluescript KS+, pACYC177, pACYC184, pAYC32, pMW119, pET22b, *E. coli-B. subtilis* shuttle vectors such as pHY300PLK, pGK12, pLF14, pLF22 or the like, phage vectors such as 11059, IBF101, M13 mp9, Mu phage (Japanese Patent Application Laid-Open No. 2-109985), or the like, and transposons (Berg, D. E. and Berg, C. M., Bio/Technol., 1, 417 (1983)), such as Mu, Tn10, Tn5, or the like. It is also possible to increase the copy number of a gene by integrating the gene into a chromosome by homologous recombination utilizing a plasmid, or the like. Examples of host cells and expression systems useful for such purpose in *Arthrobacter* sp. are described in Shaw P. C. et al. (J Gen Micobiol. 134 (1988) p. 903-911) and Morikawa, M. et al. (Appl Microbiol Biotechnol., 42 (1994), p. 300-303). In *Arthrobacter nicotinovorans*, such systems are described in Sandu C. et al. (Appl Environ Microbiol. 71 (2005) p 8920-8924). Also, expression systems developed for Coryneform bacteria have been reported to be functional in *Arthrobacter* species (Sandu C. et al.). However, the *Bacillus* species bacteria are not limited to those recited herein.

[II] Method for Producing (2S,3R,4S)-4-hydroxy-L-isoleucine

The method for producing (2S,3R,4S)-4-hydroxy-L-isoleucine ((2S,3R,4S)-4HIL) represented by the general formula (I) includes a one step reaction of direct enzymatic hydroxylation of L-isoleucine shown below:

L-isoleucine+α-ketoglutarate+$O_2$→4HIL+succinate+$CO_2$ wherein the reaction is performed in the presence of IDO, L-isoleucine, α-ketoglutarate, and one oxygen molecule. The L-isoleucine and α-ketoglutarate act as acceptor molecules, each accepting one oxygen atom. IDO catalyzes the reaction.

In the present invention, "enzymatic hydroxylation" means a hydroxylation reaction which is carried out by an IDO enzyme. Particularly, a bacterial IDO is preferred.

There are no particular limitations on the IDO that catalyzes the reaction, and any protein may be used as long as the protein is capable of catalyzing the reaction hydroxylation of L-isoleucine in the presence of α-ketoglutarate and oxygen.

A preferable example of IDO is described in section [1]. The IDO may be present in the reaction in any form, including contained within a bacterium (including a culture, bacterial cells, or treated cells), a purified enzyme, or a crude enzyme, so long as it is able to catalyze the reaction which produces (2S,3R,4S)-4HIL. When bacteria is used as the source of IDO, both (1) bacteria which naturally produce IDO, such as microorganisms belonging to the genus Bacillus, and (2) recombinant microorganisms which have been transformed with recombinant DNA as described in section [1] may be cultivated to produce IDO.

Amino acid sequences of IDO include those depicted in SEQ ID NO: 2, SEQ ID NO:8, and Table 1.

L-isoleucine dioxygenase also includes a protein as defined by following characteristics:

(A) an activity that catalyzes the reaction of producing (2S,3R,4S)-4HIL from L-isoleucine and α-ketoglutarate;

(B) the activity is dependent on a bivalent cation including $Fe^{2+}$, and (C) a molecular weight per subunit as measured by SDS-PAGE of about 29±2.0 kDa.

For example, when producing (2S,3R,4S)-4HIL using IDO-producing bacteria or bacterial cells that have been transformed with a recombinant DNA, the substrate may be added directly to the culture media during cultivation, or the bacterial cells or washed bacterial cells that have been separated from the culture may be used directly. Furthermore, treated bacterial cells that have been disrupted or lysed may also be used directly, or the IDO may be recovered from the treated bacterial cells and used as a crude enzyme solution, or the enzyme may be purified prior to conducting the reaction. Namely, as long as IDO activity is present, regardless of the form of the composition, it may be used or produce (2S,3R,4S)-4HIL.

In order to perform an hydroxylation reaction using IDO, a reaction solution containing L-isoleucine, α-ketoglutarate, and IDO or an IDO-containing composition is adjusted to the suitable temperature of 20 to 50° C., and either allowed to stand undisturbed, or agitated by shaking or stirring for 30 minutes to 5 days, while maintaining at pH 5 to 12.

The reaction velocity may also be increased by adding a bivalent cation such as $Fe^{2+}$ to the reaction mixture.

When adding bivalent cations to the reaction solution, although any salt may be used provided it does not hinder the reaction, $FeSO_4$, and so forth are preferable. The concentrations of these bivalent cations may be determined by simple preliminary studies conducted by a person with ordinary skill in the art. These bivalent cations may be added within the range of 0.01 mM to 50 mM, preferably 0.1 mM to 25 mM.

Oxygen enters the reaction from the air as a result of agitation of a fixed culture volume during cultivation.

The (2S,3R,4S)-4HIL of general formula (I) that is formed in the reaction mixture may be either separated or purified according to known techniques, or further processed, particularly when a recombinant microorganism expresses IDO.

Examples of separation and purification methods include contacting the (2S,3R,4S)-4HIL with an ion exchange resin to adsorb basic amino acids followed by elution and crystallization, and eluting the discolored product, filtrating with activated charcoal, and finally conducting crystallization.

Non-annotated genes encoding IDO from other microorganisms can be identified by their homology to the known IDO genes, followed by evaluation of the activity of proteins encoded by these genes.

Homology between two amino acid sequences can be determined by well-known methods, for example, the computer program BLAST 2.0, which calculates three parameters: score, identity, and similarity.

Therefore, the DNA fragment from Bacillus thuringiensis strain 2-e-2 and Bacillus thuringiensis (serovar israelensis; ATCC 35646) strain encoding the full-length IDO can be obtained by PCR (polymerase chain reaction; refer to White, T. J. et al., Trends Genet., 5, 185 (1989)) utilizing primers prepared based on the known amino acid and nucleotide sequences. The DNA fragment encoding IDO from other microorganisms can be obtained in a similar manner.

Since there may be some differences in DNA sequences among the bacterial strains, the above-described fragments encoding IDO are not limited to the nucleotide sequences shown in SEQ ID NO: 1, 7, 12, 16, 20, FIG. 18 or Table 1, but may also include nucleotide sequences similar to those shown in SEQ ID NO: 1, 7, 12, 16, 20, FIG. 18 or Table 1. Therefore, the protein variants encoded by the above-described genes may have a similarity of not less than 80%, preferably not less than 90%, and most preferably not less than 95%, with respect to the entire amino acid sequences shown in SEQ ID NOS. 2, 8, 13, 17, 21, FIG. 19 or Table 1, as long as the abilities of the proteins to catalyze the desired reactions are maintained.

Moreover, the above-described DNA fragments may be variants which can hybridize under stringent conditions with the nucleotide sequences shown in SEQ ID NOS: 1, 7, 12, 16, 20, FIG. 18 or Table 1, or with probes prepared based on these nucleotide sequences, provided that they encode functional proteins. "Stringent conditions" means the same as described in section [1] (1) A DNA Encoding IDO.

The treated bacterial cells which may be employed include dried bacterial mass, freeze-dried bacterial mass, products treated with surfactants or organic solvents, enzyme-treated products, ultrasound-treated products, mechanically ground products, solvent-treated products, protein fractions of bacterial mass, immobilized products of bacterial mass, and processed bacterial mass.

IDO may be prepared separately as described above, and then added to the reaction solution. A bacterium (host cell) that expresses the DNA encoding IDO may be prepared by transfecting the host cell with the expression vector containing the DNA encoding the IDO so that is able to be expressed in the chosen host cell. Furthermore, the host cells in which the expression of IDO has been increased, resulting in enhanced IDO activity, are preferably used.

The phrase "increasing the expression of the gene" means that the expression of the gene is higher than that of a non-modified strain, for example, a wild-type strain. Examples of such modifications include increasing the copy number of expressed gene(s) per cell, increasing the expression level of the gene(s), and so forth. The quantity of the copy number of an expressed gene is measured, for example, by restricting the chromosomal DNA followed by Southern blotting using a probe based on the gene sequence, fluorescence in situ hybridization (FISH), and the like. The level of gene expression can be measured by various known methods including Northern blotting, quantitative RT-PCR, and the like. The amount of the protein encoded by the gene can be measured by known methods including SDS-PAGE followed by immunoblotting assay (Western blotting analysis), and the like.

"Transformation of a bacterium with DNA encoding a protein" means the introduction of the DNA into the bacterium, for example, by conventional methods. Transformation of this DNA will result in an increase in expression of the gene encoding the protein, and will enhance the activity of the protein in the bacterial cells. Methods of transformation include any known methods that have previously been reported. For example, treating recipient cells with calcium chloride so as to increase permeability of the cells to DNA has been reported for *Escherichia coli* K-12 (Mandel, M. and Higa, A., J. Mol. Biol., 53, 159 (1970)), and may be used.

Methods of enhancing gene expression include increasing the gene copy number. Introducing a gene into a vector that is able to function in the chosen bacterium will increase the copy number of the gene. For such purposes, multi-copy vectors are preferably used, and include, for example, pBR322, pMW119, pUC19, pET22b, or the like.

Gene expression may also be enhanced by introducing multiple copies of the gene into a bacterial chromosome by, for example, homologous recombination, Mu integration, or the like. For example, one act of Mu integration allows for introduction of up to 3 copies of the gene into a bacterial chromosome.

Increasing the copy number of the gene can also be achieved by introducing multiple copies of the gene into the chromosomal DNA of the bacterium. In order to introduce multiple copies of the gene into a bacterial chromosome, homologous recombination is carried out using a target sequence which is present in multiple copies on the chromosomal DNA. Such sequences include, but are not limited to repetitive DNA, or inverted repeats, present at the end of a transposable element. Also, as disclosed in U.S. Pat. No. 5,595,889, it is possible to incorporate the gene into a transposon, and transfer it so that multiple copies of the gene are introduced into the chromosomal DNA.

Enhancing gene expression may also be achieved by placing the DNA under the control of a potent promoter. For example, the Ptac promoter, the lac promoter, the trp promoter, the trc promoter, the $P_R$, or the $P_L$ promoter of lambda phage are all known to be potent promoters. The use of a potent promoter can be combined with increasing the number of gene copies.

Alternatively, the effect of the promoter can be enhanced by, for example, introducing a mutation into the promoter to increase the transcription level of a gene located downstream of the promoter. Furthermore, it is known that substitution of several nucleotides in the spacer region between the ribosome binding site (RBS) and the start codon, especially the sequences immediately upstream of the start codon, profoundly affect the mRNA translation. For example, a 20-fold range in the expression levels was found, depending on the nature of the three nucleotides preceding the start codon (Gold et al., Annu. Rev. Microbiol., 35, 365-403, 1981; Hui et al., EMBO J., 3, 623-629, 1984). Previously, it was shown that the rhtA23 mutation is an A-for-G substitution at the −1 position relative to the ATG start codon (ABSTRACTS of 17th International Congress of Biochemistry and Molecular Biology in conjugation with 1997 Annual Meeting of the American Society for Biochemistry and Molecular Biology, San Francisco, Calif. Aug. 24-29, 1997, abstract No. 457).

Moreover, it is also possible to introduce a nucleotide substitution into the promoter region of the gene on the bacterial chromosome, which results in stronger promoter function. The expression control sequence can be altered, for example, in the same manner as the gene substitution using a temperature-sensitive plasmid, as disclosed in International Publication WO 00/18935 and Japanese Patent Application Laid-Open No. 1-215280.

Methods for preparing plasmid DNA include, but are not limited to digestion and ligation of DNA, transformation, selection of an oligonucleotide as a primer, and the like, or other methods well known to one skilled in the art. These methods are described, for instance, in "Molecular Cloning A Laboratory Manual, Third Edition", Cold Spring Harbor Laboratory Press (2001).

EXAMPLES

The present invention will be explained in further detail with reference to the following non-limiting examples.

Example 1

Screening for Strains having L-Ile Hydroxylase

<1> Screening for Strains able to Produce 4-Hydroxyisoleucine, and Analysis of the Broth By using L-isoleucine as a substrate, microorganisms were screened for the presence of 4-hydroxyisoleucine. In water, 0.4% (w/v) of soluble starch, 0.4% of yeast extract, 1% of malt extract, and 0.2% of L-isoleucine were dissolved, then the solution was adjusted to pH 7 to 7.5. Soil bacteria were inoculated into this solution. After culturing with shaking at 28° C. for 2 days, the presence of 4-hydroxyisoleucine was determined by amino acid analysis of the centrifugation supernatant.

Amino Acid Analysis Conditions

4-Hydroxyisoleucine was detected by using the Waters AccQ-Tag™ method. Amino acids in 5 µl were diluted to an appropriate concentration and derivatized in a conventional manner, and the amount of 4-hydroxyisoleucine was measured by HPLC analysis. As a result, one of the bacterial strains (strain 2-e-2) was found to have the activity of producing a substance showing the same retention time as that of 4-hydroxyisoleucine. On the basis of the analysis of 16S rDNA, the strain 2-e-2 was identified as *Bacillus thuringiensis*. Therefore, other *Bacillus* bacteria were also screened, and a similar activity was also found in *Bacillus licheniformis* (AKU 223, IAM 11054), *Bacillus sphaericus* (AKU 227, NBRC 3526), and *Bacillus thuringiensis* (AKU 238, NBRC 3958).

Identification of Product

The substance produced from L-isoleucine as a substrate by the *Bacillus* strains obtained in the aforementioned screening was identified. First, the molecular weight of the product was analyzed by MS, and found to be 145, which is twice as small as that of 4-hydroxyisoleucine. When the composition formula was estimated by precise mass measurement using a high resolution mass spectrometer (Q-TofMS), $C_6H_{11}NO_3$ was obtained, and found to have 2 times fewer hydrogen atoms than that of 4-hydroxyisoleucine. The above results suggested that the substance produced by the *Bacillus* strains may be 2-amino-3-keto-4-methylpentanoic acid (AMKP). According to the experimental method previously described, AMKP was synthesized and purified from the culture media of *Bacillus* bacteria, and NMR analysis was performed (Bioorganic Chemistry, Vol. 6, pp. 263-271, 1977). As a result, both showed similar chemical shifts.

From the above, it was determined that the *Bacillus* bacteria found in this experiment produced AMKP. The amount of AMKP produced by the strain 2-e-2 was about 1 to 2 mM. The amount of AMKP produced by the *Bacillus* bacteria described in the Bioorganic Chemistry article 7 was 0.04 mM, and thus, the 2-e-2 strain was capable of producing a much larger amount than previously described.

<2> Establishing a Method for the Separation and Analysis of AMKP and HIL

Since *Bacillus* bacteria were found to produce AMKP, a method for the separation and analysis of AMKP and 4-hydroxyisoleucine was necessary. As a result of various examinations, the method for the separation and analysis of AMKP and 4-hydroxyisoleucine was established by modifying the Waters AccQ-Tag™ method. Specifically, the column was changed to XBridge C18 5 mm, 2.1×150 mm (Waters), Eluent B was changed to MeOH, and the flow rate of the eluent was changed to 0.3 ml/min. The gradient of the eluent is shown in the following table.

TABLE 2

Eluent conditions in a simultaneous analysis of HIL and AMKP

| Time (min) | Flow (ml/min) | Accq Tag Eluent A % A | 100% MeOH % B | $H_2O$ % C | Curve |
|---|---|---|---|---|---|
| — | 0.3 | 80 | 20 | 0 | — |
| 15 | 0.3 | 60 | 40 | 0 | 6 |
| 15.1 | 0.3 | 0 | 60 | 40 | 11 |
| 18.0 | 0.3 | 80 | 20 | 0 | 11 |

Under the above conditions, AMKP in the medium eluted at around 11.0 minutes and 4-hydroxyisoleucine eluted at around 11.9 minutes. Therefore these products could be separated.

<3> Change in Amount of AMKP Produced by the Addition of Cofactors During the Culture The possibility of molecular oxygen uptake by hydroxylation was considered as a possible mechanism for the production of AMKP. Accordingly, the production of AMKP was analyzed when NAD(P)H, or $Fe^{2+}$, 2-oxoglutaric acid and ascorbic acid, were added during the culture of the 2-e-2 strain. NAD(P)H is a cofactor of monooxygenases and $Fe^{2+}$, 2-oxoglutaric acid and ascorbic acid are cofactors of dioxygenases.

The culture medium used in the previous screening was used as a control, and the production of AMKP was compared among cultures containing the cofactors as shown in Table 3. The culture temperature was 30° C., and the culture time was 22 hours. The concentration of AMKP in the culture supernatants was measured. The results are shown in Table 3.

TABLE 3

Effect of addition of cofactors on AMKP production activity in culture of strain 2-e-2

| | AMKP concentration (mM) |
|---|---|
| Control | 1.34 |
| NAD(P)H | 1.58 |
| $Fe^{2+}$ | 2.53 |
| $Fe^{2+}$, 2-oxoglutaric acid, ascorbic acid | 3.06 |

It was suggested that a dioxygenase might be involved in the production of AMKP.

<4> Changes in the 2-e-2 Strain Broth Over Time

The AMKP production medium (0.4% (w/v) of soluble starch, 0.4% of yeast extract, 1% of malt extract, 0.2% of L-isoleucine, 0.5% of glucose, 1 mM ascorbic acid, 1 mM 2-oxoglutaric acid, 1 mM $CaCl_2$, 1 mM $MgSO_4$, pH 7 to 7.5) was put into a 3-L Sakaguchi flask, and the 2-e-2 strain was cultured at 23° C. with shaking. At 0, 6, 8, 10, 12, 14, 16, 18, and 20 hours after the start of the culture, the culture broth was sampled, and the 4-hydroxyisoleucine and AMKP were quantified by the method described in <2> above. Further, turbidity ($OD_{660}$) was also measured.

Figure 2:
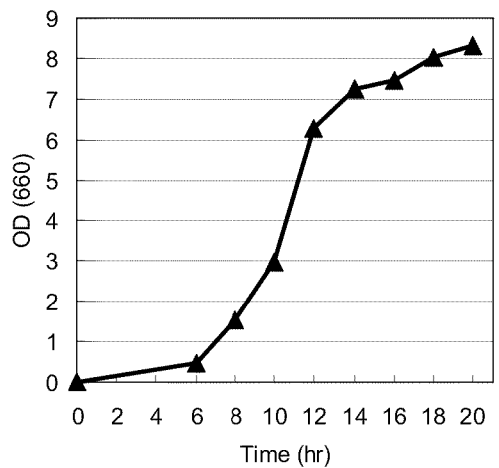
FIG. 2 is a graph which shows the change in turbidity over time of the culture of the 2-e-2 strain.

The concentrations of 4-hydroxyisoleucine (HIL) and AMKP are shown in FIG. 1. The turbidity of the culture broth is shown in FIG. 2. The 4-hydroxyisoleucine and AMKP increased in the logarithmic growth phase and then reached a plateau. After the level reached the plateau, 4-hydroxyisoleucine gradually decreased, and AMKP gradually increased.

Figure 3:
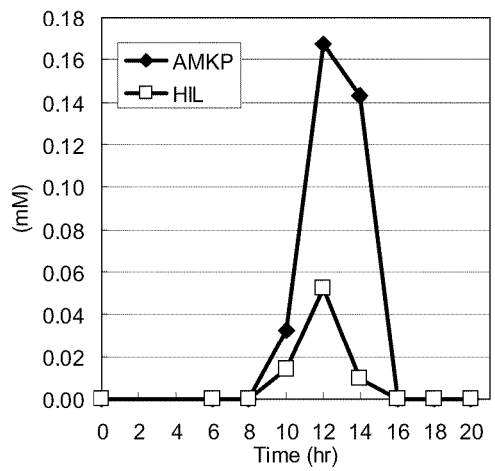
FIG. 3 is a graph which shows the accumulation over time of 4-hydroxyisoleucine and AMKP using resting cells of the 2-e-2 strain.

At each of the aforementioned culture times, 2-e-2 cells were obtained from 200 μl of the culture broth, washed with physiological saline, and then suspended in 100 μl of a dioxygenase reaction mixture (10 mM Ile, 1 mM $Fe^{2+}$, 10 mM 2-oxoglutaric acid, 10 mM ascorbic acid, 50 mM potassium phosphate buffer (pH 7.0)). The reaction occurred at 30° C. for 1 hour with shaking, and the amounts of 4-hydroxyisoleucine and AMKP in the supernatant were measured. As a result, only cells in the logarithmic growth phase were able to produce 4-hydroxyisoleucine and AMKP, although only in trace amounts, as shown in FIG. 3.

<5> Production of HIL with 2-e-2 Cell Lysate

Figure 4:
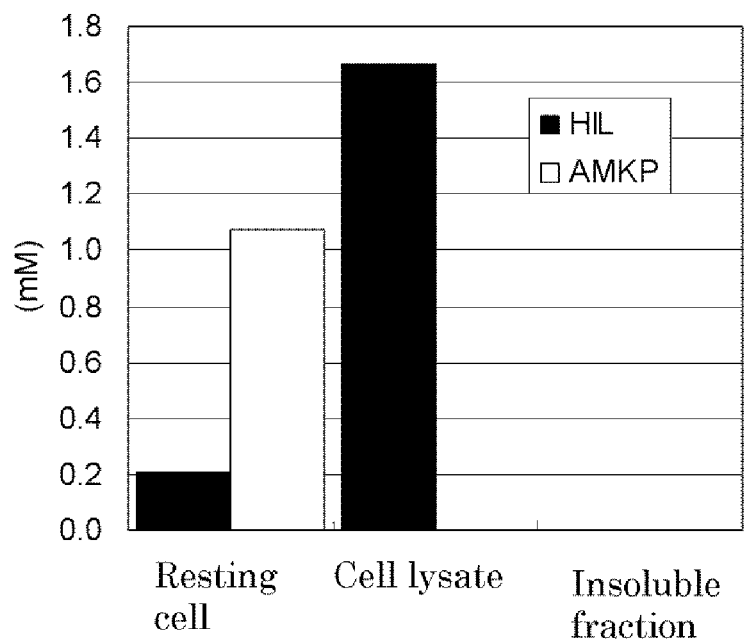
FIG. 4 is a graph which shows the 4-hydroxyisoleucine production in various samples.

The cells were cultured in the AMKP medium until $OD_{660}$ of 3.2 was achieved, then the collected and washed 2-e-2 cells were disrupted using a mortar, and suspended in a buffer (50 mM HEPES (pH 7.0), 10% of glycerol, Complete Mini (Roche)) until a suspension (lysate) is obtained having a protein concentration of about 10 mg/ml including centrifugation precipitates. The centrifugation precipitates were finally suspended in physiological saline of the same volume as the cell lysate. These were each mixed with an equal volume of a 2× dioxygenase reaction mixture (10 mM Ile, 2 mM $Fe^{2+}$, 10 mM 2-oxoglutaric acid, 10 mM ascorbic acid, 100 mM HEPES (pH 7.0)), and the reaction proceeded at 30° C. for 1 hour. Similarly, resting cells used for the preparation of the cell lysate were washed, and suspended in physiological saline at a concentration 10 times that in the culture broth, the suspension was mixed with an equal volume of the 2× dioxygenase reaction mixture, and the reaction proceeded. The amounts of AMKP and 4-hydroxyisoleucine in the samples are shown in FIG. 4.

By using the cell lysate, for the production of 4-hydroxyisoleucine using Ile as a substrate was confirmed.

<6> The Effects of Enzyme Cofactors in 2-e-2 Cell Lysate

By using a cell lysate of the 2-e-2 cells in the logarithmic growth phase, the effects of cofactors on the 4-hydroxyisoleucine production reaction by hydroxylation of Ile were examined. A 50 mM HEPES (pH 7) reaction mixture was used containing final concentrations of 5 mM Ile and 5 mM of one of various cofactors with a cell lysate of the 2-e-2 cells (lysate) in the logarithmic growth phase prepared by the method described in <5> above, and the amount of 4-hydroxyisoleucine produced was measured. As shown in Table 4, $Fe^{2+}$ (Fe) and 2-oxoglutaric acid (a-KG) were required for the production of 4-hydroxyisoleucine, and the amount of 4-hydroxyisoleucine which was produced was maximized by adding ascorbic acid (Asc.). Therefore, such results strongly suggest that a dioxygenase is involved in the production of 4-hydroxyisoleucine by hydroxylation of isoleucine.

TABLE 4

Effects of various cofactors on 4-hydroxyisoleucine production activity with 2-e-2 cell lysate

| Reaction mixture | HIL production (mM) |
|---|---|
| Lysate (—) | 0.00 |
| Lysate + Ile | 0.00 |
| Lysate + Ile + Fe | 0.00 |
| Lysate + Ile + Asc. | 0.00 |
| Lysate + Ile + a-KG | 0.00 |
| Lysate + Ile + Fe + Asc. | 0.00 |

TABLE 4-continued

Effects of various cofactors on 4-hydroxyisoleucine production activity with 2-e-2 cell lysate

| Reaction mixture | HIL production (mM) |
|---|---|
| Lysate + Ile + Fe + a-KG | 0.39 |
| Lysate + Ile + Asc. + a-KG | 0.00 |
| Lysate + Ile + Fe + Asc. + a-KG | 0.85 |

<7> Steric Configuration of Product Obtained with 2-e-2 Cell Lysate

4-Hydroxyisoleucine has asymmetric carbons at 3 sites, and 8 types of diastereomers and 4 pairs of enantiomers exist. Specifically, the 4 pairs of enantiomers are the following: the (2S,3S,4S) and (2R,3R,4R) enantiomers (also referred to as HIL1), the (2S,3S,4R) and (2R,3R,4S) enantiomers (also referred to as HIL2), the (2S,3R,4R) and (2R,3S,4S) enantiomers (also referred to as HIL3), and the (2S,3R,4S) and (2R,3S,4R) enantiomers (also referred to as HIL4). The naturally occurring HIL in Fenugreek and so forth is the (2S,3R,4S) enantiomer. Since (2S,3S)-isoleucine is used as a substrate, the 4-hydroxyisoleucine produced by the hydroxylation reaction is either the (2S,3R,4S) or (2S,3R,4R) enantiomer. Accordingly, the steric configuration of 4-hydroxyisoleucine produced by the 2-e-2 was determined.

(2R,3R,4R): HIL1 and (2S,3R,4R): HIL3 were obtained according to Tetrahedron (47(32), 6469-6482, (1991)), and (2R,3R,4S): HIL2 and (2S,3R,4S): HIL4 were obtained according to Eur. J. Org. Chem. (834-839, (2002)). When HIL1 to HIL4 were analyzed under the conditions of the simultaneous analysis of 4-hydroxyisoleucine and AMKP described in <2> above, the retention times were as shown in Table 5.

TABLE 5

Retention times of diastereomers of 4-hydroxyisoleucine

| | Retention time (min) |
|---|---|
| HIL1 | 7.25 |
| HIL2 | 14.28 |
| HIL3 | 11.10 |
| HIL4 | 11.98 |

When the sample prepared in <6> was analyzed, the retention time was 11.99 minutes. When it was mixed with 4-hydroxyisoleucine of the standard of HIL4 and analyzed, the peaks completely matched. Therefore, when (2S,3S)-isoleucine was used as the substrate, the 4-hydroxyisoleucine that was produced was HIL4, i.e., the naturally occurring 4-hydroxyisoleucine.

<8> Optimum pH of Enzyme in 2-e-2 Cell Lysate

Figure 5:
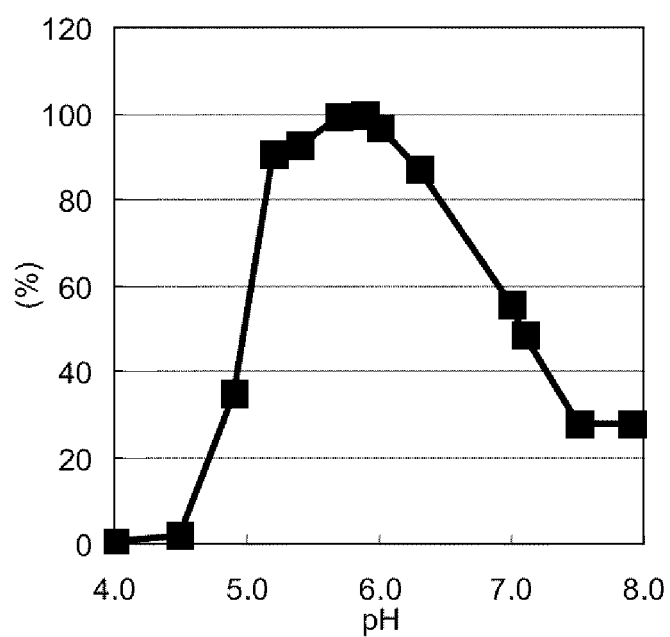
FIG. 5 is a graph which shows the relative pH dependency of the 4-hydroxyisoleucine production in the 2-e-2 cell lysate.

By using a cell lysate prepared from 2-e-2 cells at $OD_{660}$ of 7 according to the method described in <5>, the pH dependency of the 4-hydroxyisoleucine production was evaluated. The dioxygenase reaction mixture contained 5 mM Ile, 5 mM $Fe^{2+}$, 5 mM 2-oxoglutaric acid, 5 mM ascorbic acid, and 100 mM GTA, and the pH was measured after the reaction. The reaction temperature was 30° C. The 4-hydroxyisoleucine was analyzed by the method described in <2>. Activities at various pH values are shown in FIG. 5 in terms of relative activity ratios calculated on the basis of the amount of HIL produced at the pH which results in the maximum amount produced, which was taken as 100%. The activity was confirmed at pH 5 to 8.

<9> Optimum Temperature of Enzyme in the 2-e-2 Cell Lysate

Figure 6:
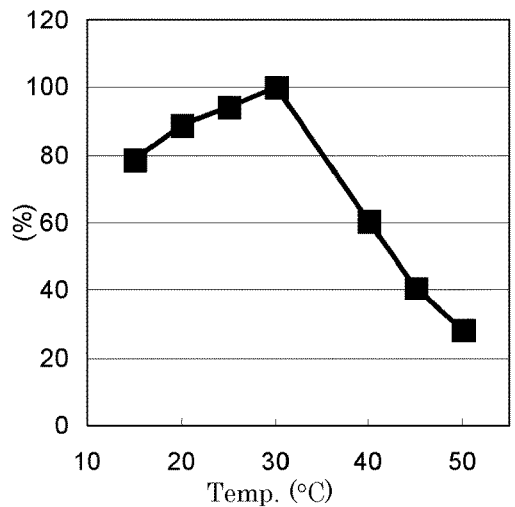
FIG. 6 is a graph which shows the relative temperature dependency of the 4-hydroxyisoleucine production in the 2-e-2 cell lysate.

By using a cell lysate prepared from 2-e-2 cells at $OD_{660}$ of 7 according to the method described in <5>, the temperature dependency of the 4-hydroxyisoleucine production was evaluated. The dioxygenase reaction mixture contained 5 mM Ile, 5 mM $Fe^{2+}$, 5 mM 2-oxoglutaric acid, 5 mM ascorbic acid and 100 mM GTA (pH 6), and the reaction temperature was 15 to 50° C. The 4-hydroxyisoleucine which was produced was analyzed by the method described in <2>. Activities at various temperatures are shown in FIG. 6 in terms of relative activity ratios calculated on the basis of the amount of 4-hydroxyisoleucine produced at the temperature which results in the maximum amount produced, which was taken as 100%. The optimum temperature was lower than 45° C.

<10> Temperature Stability of Enzyme in 2-e-2 Cell Lysate

Figure 7:
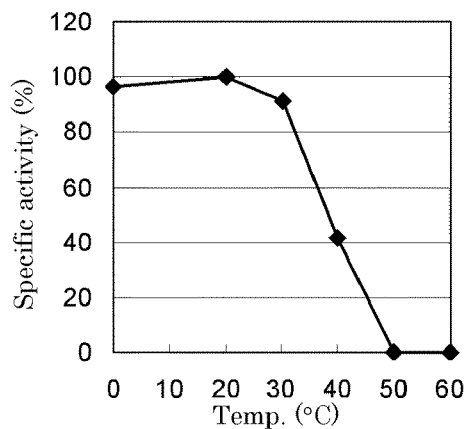
FIG. 7 is a graph which shows the relative temperature stability of the 4-hydroxyisoleucine production in the 2-e-2 cell lysate.

By using a cell lysate prepared from 2-e-2 cells at $OD_{660}$ of 7 according to the method described in <5>, the temperature stability of the 4-hydroxyisoleucine production was evaluated. The cell lysate was incubated at 0 to 50° C. for 1 hour, and then the Ile hydroxylation activity was measured. The substrate reaction mixture contained 5 mM Ile, 5 mM $Fe^{2+}$, 5 mM 2-oxoglutaric acid, 5 mM ascorbic acid, and 100 mM HEPES (pH 7), and the reaction temperature was 30° C. The 4-hydroxyisoleucine which was produced was analyzed by the method mentioned in Example 2. Temperature stabilities at various temperatures are shown in FIG. 7 in terms of relative activity ratios calculated on the basis of the amount of 4-hydroxyisoleucine produced at the temperature which results in the maximum amount produced, which was taken as 100%. The enzyme was inactivated at a temperature of 50° C. or higher.

<11> Substrate Reaction Characteristics of Enzyme in 2-e-2 Cell Lysate

By using a cell lysate prepared from 2-e-2 cells at $OD_{660}$ of 7 according to the method described in <5>, the reaction characteristics for various amino acids were evaluated. The cell lysate and a substrate solution were mixed, then the reaction proceeded at 30° C. for 1 hour, and the production of new substances was evaluated by TLC or amino acid analysis. The substrate reaction mixture contained 5 mM amino acid, 5 mM $Fe^{2+}$, 5 mM 2-oxoglutaric acid, 5 mM ascorbic acid, and 100 mM HEPES (pH 7). In addition to L-isoleucine, the amino acids L-leucine, L-valine, L-glutamic acid, and L-lysine were each individually evaluated. The 4-hydroxyisoleucine which was produced was analyzed by the method described in Example 1. The results are shown in Table 6. Production of amino acids other than L-isoleucine was not observed. Therefore, it was suggested that this enzyme was an isoleucine-specific dioxygenase.

TABLE 6

Reactivity for various amino acids

| | Product |
|---|---|
| L-Isoleucine | Produced (HIL) |
| L-Leucine | None |
| L-Valine | None |
| L-Glutamic acid | None |
| L-Lysine | None |

<12> Effect of Inhibitors in the 2-e-2 Cell Lysate

By using a cell lysate prepared from 2-e-2 cells at $OD_{660}$ of 7 according to the method described in <5>, the effects of inhibitors on the 4-hydroxyisoleucine production were examined. A cell lysate prepared from 2-e-2 cells at $OD_{660}$ of 7 according to the method described in <5> was used. The dioxygenase reaction mixture contained 5 mM Ile, 5 mM $Fe^{2+}$, 5 mM 2-oxoglutaric acid, 5 mM ascorbic acid, and 100 mM HEPES (pH 6), the reaction temperature was 30° C., and the reaction time was 1 hour. The amount of 4-hydroxyisoleucine which was produced when 10 mM of each inhibitor (EDTA, $Cu^{2+}$, $Zn^{2+}$) was added to the reaction system was measured. 4-Hydroxyisoleucine was analyzed by the method described in <2>. The isoleucine hydroxylation activity was inhibited by the inhibitors.

Example 2

Isolation and Purification of L-Ile Hydroxylase (1) Preparation of Cell-Free Extract The 2-e-2 strain was cultured in a total volume of 2 L of AMKP production medium until $OD_{660}$ of 6.0 was achieved, and then the cells were washed with physiological saline. The cells were suspended in a cell membrane treatment solution (10 mg/ml of lysing enzyme (SIGMA), 5 mg/ml of cellulase "ONOZUKA" R-10 (Yakult), Yatalase (Takara Bio), 1 mg/ml of lysozyme (SIGMA), dissolved in 0.2 M $NaH_2PO_4$ and 0.6 M KCl (pH 5.5)), and then incubated at 30° C. for 1 hour. The incubated cells were washed with physiological saline, and then suspended in Buffer A (50 mM HEPES (pH 7.0), 10% of glycerol, 2 mM DTT, 1 mM EDTA, Complete (Roche)), and the cells were disrupted by using an ultrasonic disruptor (Branson) while on ice. This treated suspension was centrifuged at 4° C. and 18,500×g for 60 minutes to obtain a supernatant. The subsequent isolation and purification procedures were all performed at 4° C. or on ice.

(2) Anion Exchange Chromatography

The supernatant obtained in the previous step was filtered through a filter with a pore size of 0.45 μm, and applied to a DEAE column (16 mm×100 mm, GE Healthcare Bio-Sciences) equilibrated beforehand with Buffer A. The column was washed with Buffer A, and elution was performed with a linear concentration gradient of sodium chloride in Buffer B (50 mM HEPES (pH 7.0), 10% of glycerol, 2 mM DTT, 1 mM EDTA, 0.5 M NaCl, Complete (Roche)).

(3) Detection of Active Fraction

Each fraction was reacted using an Ile hydroxylation activity reaction mixture (100 mM HEPES (pH 6.0), 5 mM L-Ile, 5 mM $Fe^{2+}$, 5 mM 2-oxoglutaric acid, 5 mM ascorbic acid at final concentrations) at 30° C. for 30 minutes. The enzyme was inactivated at 100° C., and then the amount of 4-hydroxyisoleucine was quantified by the aforementioned AMKP and HIL separation and measurement method. The 4-hydroxyisoleucine referred to in the subsequent analysis indicates a substance that is substantially composed of the isomer having the same retention time as that of the naturally occurring 4-hydroxyisoleucine. The enzyme activity that produces 1 nmol of HIL per minute was defined as 1 U.

(4) Cation Exchange Chromatography

The buffer in the active fraction obtained in the previous step was changed to Buffer C (50 mM MES (pH 5.2), 10% of glycerol, 2 mM DTT, 1 mM EDTA, Complete (Roche)) in a desalting column (GE Healthcare Bio-Sciences). Then it was applied to a MonoS column (10 mm×100 mm, GE Healthcare Bio-Sciences) equilibrated beforehand with Buffer C. The column was washed with Buffer C, then eluted with a linear concentration gradient of sodium chloride in Buffer D (50 mM MES (pH 5.2), 10% of glycerol, 2 mM DTT, 1 mM EDTA, 0.5 M NaCl, Complete (Roche)), and the Ile hydroxylation activity of each fraction was measured.

(5) Ammonium Sulfate Precipitation

2 M Ammonium sulfate was added to the soluble fraction obtained in the previous step and dissolved. The solution was sufficiently stirred, and then fractionated into a soluble fraction and a precipitate fraction by centrifugation, and the precipitate fraction was dissolved in Buffer A. When the Ile hydroxylation activity of each fraction was measured, the activity was detected in the precipitate fraction.

(6) Size Exclusion Chromatography

The active fraction obtained in the previous step was applied to a Superdex 75 column (10 mm×300 mm, GE Healthcare Bio-Sciences) equilibrated beforehand with Buffer A. Elution was performed with Buffer A, and the Ile hydroxylation activity of each fraction was measured.

(7) Hydrophobic Interaction Chromatography

The buffer in the active fraction obtained in the previous step was changed to Buffer E (50 mM MES (pH 6.5), 10% of glycerol, 2 mM DTT, 1 mM EDTA, 1 M ammonium sulfate, Complete (Roche)). The this fraction was then applied to a Resource PHE column (1 ml, GE Healthcare Bio-Sciences) equilibrated beforehand with Buffer E. The column was washed with Buffer E, and then a fraction containing the enzyme having the Ile hydroxylation activity was eluted with Buffer F (50 mM MES (pH 6.5), 10% of glycerol, 2 mM DTT, 1 mM EDTA, Complete (Roche)) by using a reverse linear concentration gradient of ammonium sulfate.

The outline of the isolation and purification of L-Ile hydroxylase are summarized in Table 7.

TABLE 7

Summary of isolation and purification

| Fraction | Total protein (mg) | Specific activity (U/mg) | Total activity (U) | Yield (%) |
|---|---|---|---|---|
| Cell-free extract | 678.173 | 3.8 | 2593.7 | 100.0 |
| DEAE | 73.324 | 17.8 | 1306.5 | 50.4 |
| monoS | 3.639 | 96.5 | 351.0 | 13.5 |
| Ammonium sulfate precipitation | 0.578 | 209.5 | 121.1 | 4.7 |
| GPC | 0.093 | 1222.8 | 113.4 | 4.4 |
| Resource PHE | 0.004 | 3694.9 | 13.2 | 0.5 |

Example 3

Characterization of L-Ile Hydroxalase

<1> Analysis by Electrophoresis

The purified sample obtained in Example 2 was analyzed by sodium dodecylsulfate-polyacrylamide gel electrophoresis (polyacrylamide gel: PAG Mini "Daiichi" 15/25 (13 wells) produced by Daiich Pure Chemicals Co., Ltd., molecular weight standards: Prestained SDS-PAGE Standards, Low Range, produced by Bio-Rad). As a result, the enzyme is made up of substantially uniform subunits each having a molecular weight of about 31,000±20,000.

<2> Effects of Addition of Cofactors

The effects of cofactors on the production of 4-hydroxyisoleucine by hydroxylation of Ile were examined by using the purified enzyme. The L-Ile hydroxylase prepared as described in Example 2 was used in a 100 mM HEPES (pH 6) reaction mixture containing final concentrations of 5 mM L-Ile and 5 mM of a cofactor, and the amount of 4-hydroxyisoleucine which was produced was measured. As shown in Table 8, $Fe^{2+}$ and 2-oxoglutaric acid were essential for the production of 4-hydroxyisoleucine, and the amount of 4-hydroxyisoleucine produced was maximized by further adding ascorbic acid. Therefore, these data strongly suggest that a dioxygenase might be involved in the production of 4-hydroxyisoleucine by hydroxylation of L-isoleucine. This result was the same as the when using a cell lysate.

TABLE 8

Effect of various cofactors on the production of purified 4-hydroxyisoleucine

| Extract | Substrate (L-Ile) | Cofactor | HIL (mM) |
|---|---|---|---|
| + | − | — | 0.00 |
| + | + | — | 0.00 |
| + | + | α-KG | 0.00 |
| + | + | Ascorbate | 0.00 |
| + | + | $Fe^{2+}$ | 0.00 |
| + | + | α-KG + ascorbate | 0.00 |
| + | + | α-KG + $Fe^{2+}$ | 0.02 |
| + | + | Ascorbate + $Fe^{2+}$ | 0.00 |
| + | + | α-KG + ascorbate + $Fe^{2+}$ | 0.26 |

<3> Optimum pH

Figure 8:
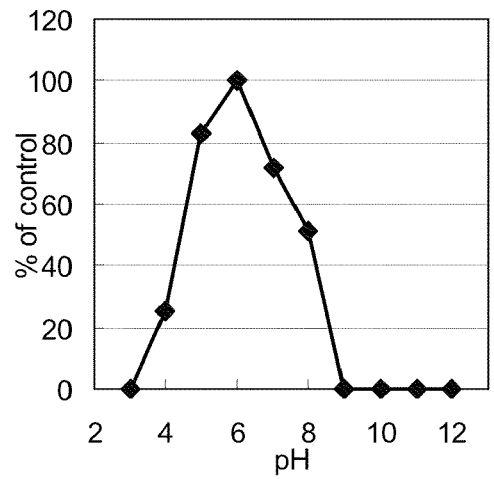
FIG. 8 is a graph showing the pH dependency of the 4-hydroxyisoleucine production using a purified enzyme.

By using L-Ile hydroxylase prepared as described in Example 2, pH dependency on the producing of the 4-hydroxyisoleucine was evaluated. The enzymatic reaction solution contained 5 mM L-Ile, 5 mM $Fe^{2+}$, 5 mM 2-oxoglutaric acid, 5 mM ascorbic acid and 200 mM GTA (pH 3 to 12). The reaction temperature was 30° C. The relative amounts of 4-hydroxyisoleucine produced at various pH values are shown in FIG. 8. These values are relative to the pH which resulted in the production of the maximum amount of 4-hydroxyisoleucine, which was set as 100%. Production of a large amount was confirmed at pH 4 to 8, and production of the most 4-hydroxyisoleucine was confirmed at pH 5 to 8.

<4> Optimum Temperature

Figure 9:
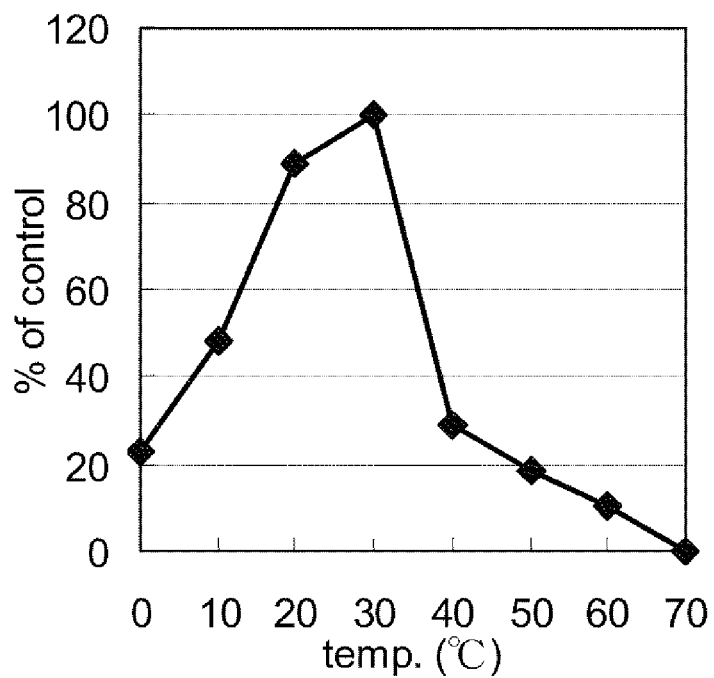
FIG. 9 is a graph showing the temperature dependency of the 4-hydroxyisoleucine production using a purified enzyme.

By using L-Ile hydroxylase prepared as described in Example 2, the optimum temperature of the 4-hydroxyisoleucine production activity was evaluated. The enzymatic reaction solution contained 5 mM Ile, 5 mM $Fe^{2+}$, 5 mM 2-oxoglutaric acid, 5 mM ascorbic acid, and 100 mM HEPES (pH 6). The relative amounts of 4-hydroxyisoleucine at various temperatures are shown in FIG. 9. These values are relative to the temperature which resulted in the production of the maximum amount of 4-hydroxyisoleucine, which was set as 100%. High production was confirmed for the temperature range of 0 to 40° C.

<5> Temperature Stability

Figure 10:
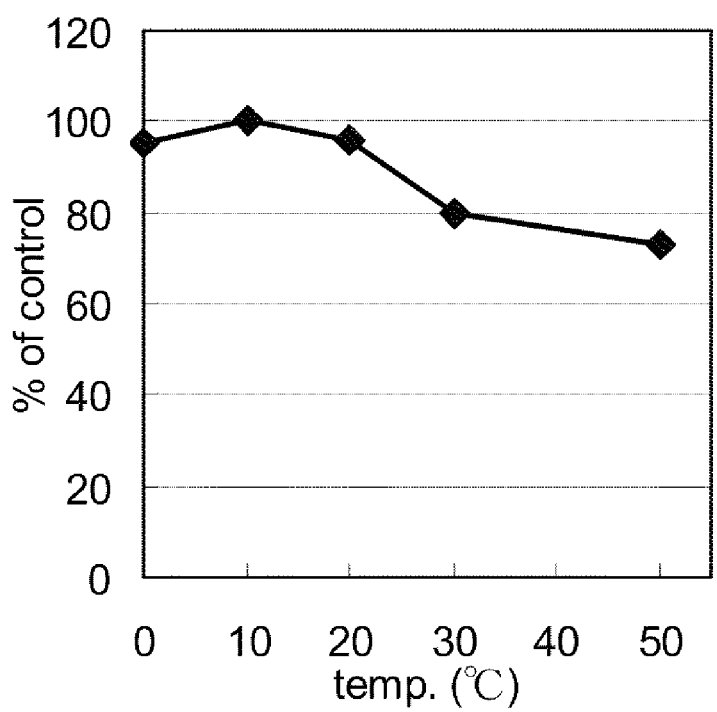
FIG. 10 is a graph which shows the temperature stability of the 4-hydroxyisoleucine production using a purified enzyme.

By using L-Ile hydroxylase prepared as described in Example 2, the temperature stability during production of 4-hydroxyisoleucine was evaluated. The enzyme solution at pH 7.0 was incubated at 0 to 70° C. for 1 hour, and then the Ile hydroxylation activity was measured. The enzymatic reaction solution contained 5 mM Ile, 5 mM $Fe^{2+}$, 5 mM 2-oxoglutaric acid, 5 mM ascorbic acid, and 100 mM HEPES (pH 6), and the reaction temperature was 30° C. The relative temperature stability at various temperatures is shown in FIG. 10. These values are relative to the storage temperature which produced the maximum amount of hydroxyisoleucine, which was set as 100%. The enzyme was inactivated at 60° C. or higher.

<6> Substrate Reaction Characteristics

By using L-Ile hydroxylase prepared as described in Example 2, the reaction characteristics for various amino acids were evaluated. The enzyme solution and the reaction mixture were mixed, and then the reaction proceeded at 30° C. for 1 hour, and the production of new substances was evaluated by HPLC analysis. The enzymatic reaction solution contained 5 mM amino acid, 5 mM $Fe^{2+}$, 5 mM 2-oxoglutaric acid, 5 mM ascorbic acid, and 100 mM HEPES (pH 6). In addition to L-isoleucine, the amino acids D-isoleucine, L-leucine, L-valine, L-glutamic acid, and L-lysine were also individually evaluated. The produced 4-hydroxyisoleucine was analyzed as in Example 1. The results are shown in Table 9. Like when using a cell lysate, production of a new substance could not be confirmed for amino acids other than L-isoleucine. Therefore, these data suggest that the enzyme is an L-isoleucine-specific dioxygenase, and contributes to the production of naturally occurring HIL, as similarly shown by the results of the examination using a cell lysate.

TABLE 9

Reactivity for each amino acid

| | Product |
|---|---|
| L-Isoleucine | Produced (HIL) |
| D-Isoleucine | None |
| L-Leucine | None |
| L-Valine | None |
| L-Glutamic acid | None |
| L-Lysine | None |

<7> Effects of Inhibitors

By using L-Ile hydroxylase prepared as described in Example 2, the effect of inhibitors on the production of 4-hydroxyisoleucine were examined. The enzymatic reaction solution contained 5 mM Ile, 5 mM $Fe^{2+}$, 5 mM 2-oxoglutaric acid, 5 mM ascorbic acid, and 100 mM HEPES (pH 6), the reaction temperature was 30° C., and the reaction time was 1 hour. The amount of 4-hydroxyisoleucine produced when 10 mM of each inhibitor (EDTA, $Cu^{2+}$, $Zn^{2+}$) was added to the reaction system was measured. The production of 4-hydroxyisoleucine in the presence of the inhibitors is shown in Table 10. These values are relative to the 4-hydroxyisoleucine production observed with no inhibitor, which was set as 100%. The isoleucine hydroxylation activity was lost in the presence of the inhibitors.

TABLE 10

Effect of inhibitors

| Inhibitor | Relative activity (%) |
|---|---|
| None | 100 |
| EDTA | 0 |
| $Cu^{2+}$ | 0 |
| $Zn^{2+}$ | 0 |

<8> N-Terminus Amino Acid Sequence

L-Ile hydroxylase prepared as described in Example 2 was subjected to electrophoresis as described in Example 3, transferred to a PVDF membrane (sequi-Blot™ PVDF membrane, Bio-Rad), and used in PPSQ-10 (a protein sequencer produced by Shimadzu Corporation). The following N-terminal sequence of the enzyme was obtained by this method.

(SEQ ID NO: 5)
```
 1    LysMetSerGlyPheSerIleGluGluLys      10
11    ValHisGluPheGluSerLysGlyPheLeu      20
```

Example 4

Purification of IDO from *Bacillus thuringiensis* (2-e-2) Strain

Environmental microorganisms were screened and a unique microbe possessing α-ketoglutarate-dependent L-isoleucine dioxygenase activity was found. It was identified as *Bacillus thuringiensis* and stocked as *Bacillus thuringiensis* strain 2-e-2 (FERM BP-10688).

1.1. Cultivation Conditions: the Following Cultivation Medium was Used in the experiments:

CM1 (Tryptone 10 g/l; Yeast extract 10 g/l; pH 7.0 adjusted by NaOH);

CM6 (Tryptone 10 g/l; Yeast extract 40 g/l; pH 7.0 adjusted by NaOH).

1.2. Inoculum preparation: *Bacillus thuringiensis* strain 2-e-2 was cultivated overnight at 30° C. in CM1 medium supplemented with 90 mM KPi buffer (90 mM $KH_2PO_4$(pH 7) adjusted with KOH). Then, glycerol was added up to 20%. The resulting cell suspension was aliquoted in 1.9 ml vials and stored at −70° C. until used.

1.3. Fermentation conditions: *Bacillus thuringiensis* strain 2-e-2 was fermented in Marubischi fermenters. The following cultivation parameters were used: starting culture volume: 600 ml; agitation: 800 rev/min; air: 1:1; pH 7.0 was stabilized using 1H NaOH/HCl feeding. One vial of a frozen suspension from (1.2) above (1.9 ml) was used to inoculate 600 ml of CM6 medium. Strain 2-e-2 was cultivated for about 7.5 hours. Then, the cells were harvested by centrifugation and stored at −70° C. until used.

1.4. IDO activity assay: Cells from 25-100 ml of the *Bacillus thuringiensis* 2-e-2 culture were harvested by centrifugation at 4° C. and re-suspended in 2 ml of buffer A (50 mM MOPS, 10% glycerol, 1 mM EDTA, 1 mM DTT, protease inhibitor, pH 7.2). The cells were disrupted using a French-pressure cell (3× at 1000 Psi). The reaction mixture (50 μl) contained 50 mM HEPES (pH 7.0), 5 mM Ile, 5 mM ascorbate, 10 mM $FeSO_4$, 5 mM α-ketoglutarate, and an aliquot of the protein preparation. The reaction was incubated at 34° C. for 40 min with shaking. The synthesized 4HIL was detected using TLC analysis. Thin-layer silica gel plate (10×15 cm) spotted with an aliquot (1-2 μl) of the reaction solution was developed with a developing solvent (2-propanol:acetone: ammonia:water=1100:100:25:16), and 4HIL was detected with the ninhydrin reagent. HPLC analysis was carried out as described in Example 4.

1.5. Purification and Identification of IDO from *Bacillus thuringiensis* 2-e-2.

All chromatographic procedures were carried out using AKTAbasic100 system (Amersham Pharmacia Biotech). The purification protocol includes the following steps. Frozen cells (62 g of weight biomass) were thawed and re-suspended in 150 ml buffer A [50 mM TRIZMA, 5% glycerol, 1 mM EDTA, 1 mM DTT, protease inhibitor, pH 7 adjusted with HCl].

Step 1: Cells were disrupted by 2 passages through the French pressure cell (max P 1000 Psi) followed by centrifugation (14000 g, 4° C., 20 min) to remove cellular debris. The protein preparation was added to 150 ml of the DEAE resin equilibrated with buffer A. The final suspension was incubated at 4° C. for about 10 minutes with low shaking. Then, the resin with the adsorbed protein was transferred to the column (26×30 cm) and a two-step protein elution was carried out. At first, the column was washed with 50 mM NaCl in buffer A. Then, the IDO activity was eluted with 250 mM NaCl in buffer A.

Step 2: The IDO activity was concentrated by ammonium sulphate precipitation (at 1.9 M) and resuspended in about 3 ml of buffer B[50 mM TRIZMA, 5% glycerol, 1 mM EDTA, 1 mM DTT, 100 mM NaCl, pH 7].

Step 3: 1.5 ml of the preparation from Step 2 was applied to the Superdex 200 HR 10/30A column equilibrated with buffer B. Isocratic elution was performed at a 0.5 ml/min flow rate. Active fractions were pooled.

Step 4: The protein preparation from step 3 was applied to a 1.6 ml Sourse15Q column equilibrated with buffer A. The elution was carried out at a flow rate of 0.5 ml/min by liner gradient 0-0.5 M NaCl in buffer B (10 column volumes). Each 1 ml fraction was collected. Active fractions were pooled.

As a result, IDO was purified about 120-fold (see Table 11). SDS-PAGE of the final protein preparation revealed only one major band (about 70% of total protein, see FIG. 12).

TABLE 11

Purification of IDO from *Bacillus thuringiensis* 2-e-2.

| Step | Total protein (mg) | Total activity (nmoles/min) | Specific activity (nmoles/min/mg) | Yield (%) | Purification fold |
|---|---|---|---|---|---|
| Cell extract | 3072 | 19046 | 6 | 100 | 1 |
| DEAE (batch) | 1500 | 18750 | 12.5 | 98 | 2 |
| $(NH_4)_2SO_4$ | 109 | 12514 | 115 | 65 | 19 |
| Superdex 200 HR | 6 | 1356 | 226 | 7 | 38 |
| Source 15Q | 0.03 | 21 | 700 | 0.1 | 117 |

1.6 Identification of IDO.

The major protein was extracted from the SDS-PAGE gel and analyzed by mass spectrometry analysis. The treatment of gels, trypsinolysis, protein extraction, and mass analysis by time-of-flight matrix-assisted laser desorption-ionization (MALDI-TOF) were carried out according to protocols described by Govorun, V. M. et al, (The proteome comparative analysis of *Helicobacter pylori* clinical isolates. *Biochemistry* (Mosc), 68, 1, 42-49 (2003)). The protein was identified by the set of its photolytic peptide masses using Peptide Fingerprint option of Mascot software (Matrix Science, USA). The analyzed protein was identified by MS-analysis as a putative RBTH_06809 protein from the *Bacillus thuringiensis* (serovar israelensis; ATCC 35646) strain (FIG. 13).

Example 5

Cloning IDO Genes from *Bacillus thuringiensis* Strain 2-e-2 and *Bacillus thuringiensis* (Serovar Israelensis, ATCC 35646) Strains The purified sample was electrophoresed in a SDS (15-25%) polyacrylamide gel. Protein transfer was performed for 1 h at 1 mA cm at room temperature onto a polyvinylidenedifluoride membrane. After being stained with CBB, the IDO band was cut out and subjected to automated Edman degradation on the protein sequencer model PPSQ-10 (Shimadzu Co. Ltd., Kyoto, Japan). The first 20 N-terminal amino acids of the purified protein were determined.

The N-terminal amino acid sequence of the 31-kDa polypeptide was determined to be KMSGF-SIEEKVHEFESKGFL (SEQ ID NO: 5). After a BLAST search, this amino acids sequence showed high homology with hypothetical proteins of RBTH_06809 from *Bacillus thuringiensis* (serovar israelensis) ATCC 35646 and BC1061 from *Bacillus cereus* ATCC 14579 as shown in Table 1.

Sequence analysis of the RBTH_06809 ORF and determination of the N-terminal amino acid of the purified protein indicate that there is only one potential IDO translation start because the classic SD sequence is located 8 bp upstream of the ATG start codon (FIG. 14). However, Lys(7) is an N-terminal amino acid of the purified protein. Therefore, N-terminal processing, or the cleavage of the N-terminal amino acids, is likely necessary for IDO activity. Seemingly, such cleavage is likely accomplished by a specific protease which co-expresses with the IDO in Bacillus sp., but is not present in E. coli. Therefore, to produce mature IDO in E. coli, special recombinant plasmids were constructed.

2.1. Bacteria: Bacillus thuringiensis (serovar israelensis, ATCC 35646) strain was obtained from the Russian Collection of Industrial Microorganisms (VKPM), accession number B-197.

2.2 Construction of the pMW19-IDO(Lys, 32) plasmid: To construct pMW119-IDO(Lys, 32) the following procedures were carried out.

Figure 15:
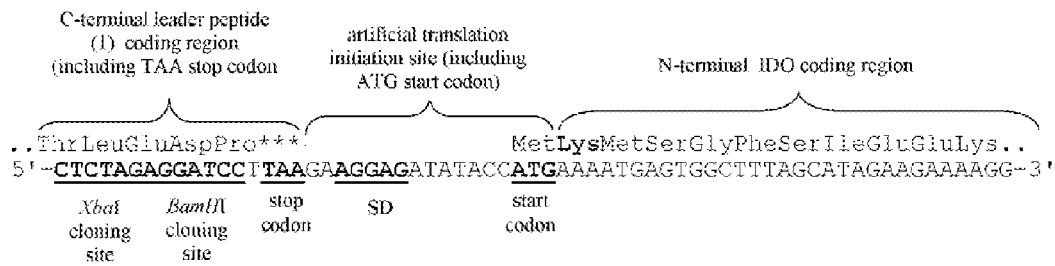
FIGS. 15A, B and C shows the artificial expression modules of the recombinant pMW119-IDO(Lys, 32/23) plasmids.
In FIG. 15B, the nucleotide sequence is shown in SEQ ID NO:38 and amino acid sequences are shown in SEQ ID NOs:39-40.
In FIG. 15C, the nucleotide sequence is shown in SEQ ID NO:41 and the amino acid sequences are shown in SEQ ID NOs:42 and 40.

A 0.8 kb DNA fragment of the chromosome of the Bacillus thuringiensis (serovar israelensis, ATCC 35646) strain was amplified using oligonucleotides SVS 170 (SEQ ID No:3) and SVS 169 (SEQ ID No:4) as primers (for detail see FIG. 15), and the purified chromosomal DNA as the template. The following PCR protocol was used: initial cycle for 30 seconds at 94° C.; 4 cycles for 40 seconds at 94° C.; 30 seconds at 49° C.; 40 seconds at 72° C.; 35 cycles for 30 seconds at 94° C.; 30 seconds at 54° C.; 30 seconds at 72° C. The PCR-fragment was digested with BamHI and SacI endonucleases and then ligated into a pMW119 vector which had been previously treated with the same restrictases.

2.3 Construction of the pMW19-IDO(Lys, 23) plasmid: A 0.8 kb DNA fragment of the chromosome of the Bacillus thuringiensis strain 2-e-2 was amplified using oligonucleotides SVS 170 (SEQ ID No:3) and SVS 169 (SEQ ID No:4) as primers (for detail see FIG. 15), and the purified chromosomal DNA as the template. The following PCR protocol was used: initial cycle for 30 seconds at 94° C.; 4 cycles for 40 seconds at 94° C.; 30 seconds at 49° C.; 40 seconds at 72° C.; 35 cycles for 30 seconds at 94° C.; 30 seconds at 54° C.; 30 seconds at 72° C. The PCR-fragment was digested with BamHI and SacI endonucleases and then ligated into a pMW119 vector which had been previously treated with the same restrictases.

Cells of E. coli strain TG1 were transformed with the ligation mixtures. The resulting clones were selected on a X-gal/IPTG agar-plate (blue/white test). Then, the IDO activity was tested in the crude cell lysates of selected clones.

Figure 16:
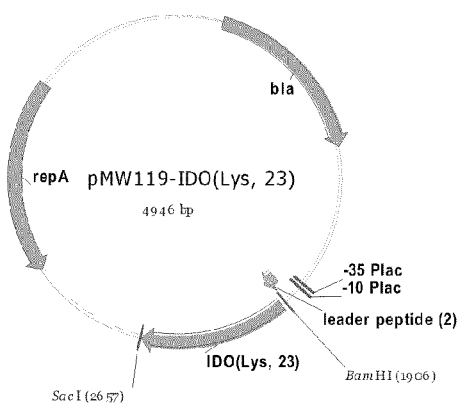
FIG. 16 is a physical map of the pMW119-IDO(Lys, 23) plasmid and the DNA sequence of the cloned BamHI-SacI fragment containing the IDO structural gene. The spontaneous point mutation in the regulatory region is marked by shading. The nucleotide sequence is shown in SEQ ID NO:43. The amino acid sequence is shown in SEQ ID NO:44.

As a result, two clones, TG1 [pMW119-(Lys, 32)] and TG1 [pMW119-(Lys, 23)], were selected. Corresponding plasmids were isolated and sequence analysis of the cloned BamHI-Sac fragments for each plasmid was carried out (see FIG. 16, FIG. 17).

Analyses of the determined DNA sequences revealed discrepancy between the cloned genes and the known RBTH_06809 ORF (FIG. 18, FIG. 19). In addition, a point mutation in the regulatory region of IDO(Lys, 23) on the plasmid pMW119 was found (FIG. 15 C) resulting in elimination of the TAA stop codon of the leader peptide (1) and prolongation of translation up to the TGA stop codon (leader peptide (2)) which overlaps with the ATG start codon (see FIG. 15 A, C). An additional mutation was detected in the "−2" position, where a C was substituted by an A (see FIG. 15, C).

2.4. The IDO activity assay in crude cell lysate of TG1 [pMW119-IDO(Lys, 23) and TG1[pMW119-IDO(Lys, 32): To investigate the IDO activity in crude cell lysates of recombinant E. coli strains, the following procedures were carried out. Cells from 5 ml of culture were harvested by centrifugation at 4° C., re-suspended in 0.5 ml of buffer A*(50 mM TRIZMA, 5% glycerol, 1 mM EDTA, 1 mM DTT, pH 7 adjusted by HCl) and disrupted by sonication at 4° C. The reaction mixture (50 μl) contained 50 mM HEPES pH 7.0, 5 mM Ile, 0.5 mM α-ketoglutarate, 5 mM ascorbate, 5 mM $FeSO_4$, and an aliquot of the protein preparation. The reaction was incubated at 34° C. for 1 hour with shaking. The synthesized 4HIL was detected using TLC or HPLC analysis as described in Example 4. The results are summarized in Table 12.

TABLE 12

| Strain | IDO activity (nmoles/mg * min) |
| --- | --- |
| TG1[pMW119] | ND[a] |
| TG1[pMW119-IDO(Lys, 23)] | 15 |
| TG1[pMW119-IDO(Lys, 32)] | 3 |

[a]ND—non detected (($\leq$0.03 nmoles/mg * min)

Example 6

Biotransformation of L-Isoleucine into 4HIL Using IDO

Cells of recombinant E. coli strains TG1[pMW19-IDO(Lys, 23)] and TG1[pMW119-IDO(Lys, 32)] were cultivated in LB medium supplemented with ampicillin (100 mg/l), until an optical density of $A_{540}$=4-5 was reached (approximately 6 hours). After that, cells from 2 ml culture broth were harvested by centrifugation and resuspended in 1 ml of MI50 solution (100 mM $KH_2PO_4$(pH 7 adjusted by NaOH), $NH_4Cl$ 20 mM, $MgSO_4$ 2 mM, $CaCl_2$ 0.1 mM, ampicillin 150 μg/ml, Ile 50 mM, 0.5 mM α-ketoglutarate, glycerol 1%, yeast extract −0.005 g/l).

Then, the cells were cultivated for about 12 hours. After that, the concentration of 4HIL was analyzed by TLC (HPLC). The data are summarized in Table 13. As shown in Table 12, cultivation of TG1[pMW119-IDO(Lys, 23)] resulted in the production of a more 4HIL as compared with TG1[pMW119-IDO(Lys, 32)].

TABLE 13

| Strain | OD540 0 h | OD540 12 h | Ile supplied (mM) | 4HIL obtained (mM) | Yield[b] (%) |
| --- | --- | --- | --- | --- | --- |
| TG1[pMW119] | 10 | 20 | 50 | ND[a] | — |
| TG1[pMW119-IDO(Lys, 23)] | 10 | 20 | 50 | 7 | 14 |
| TG1[pMW119-IDO(Lys, 32)] | 10 | 20 | 50 | 5 | 10 |

[a]ND—non detected ($\leq$0.02 mM)
[b]Yield was calculated as (4HIL obtained/Ile supplied) * 100

Example 7

HPLC Measurement of 4-Hydroxy-L-Isoleucine

HPLC analysis: High pressure chromatograph (Waters, USA) with spectrofluorometer 1100 series (Agilent, USA) was used. The chosen detection wave range: excitation wavelength at 250 nm, range of emission wavelengths were 320-560 nm. The separation by the accq-tag method was performed in a Nova-Pak C18 150×3.9 mm, 4 μm column (Waters, USA) at +400° C. The injection volume of the sample was 5 μl. The formation of amino acid derivatives and their separation was performed according to Waters manufacturer's recommendation (Liu, H. et al, J. Chromatogr. A, 828, 383-395 (1998); Waters accq-tag chemistry package. Instruction manual. Millipore Corporation, pp. 1-9 (1993)). To obtain amino acid derivatives with 6-aminoquinolil-N-hydroxysuccinymidyl carbamate, the Accq-Fluor™ kit (Waters, USA) was used. The analysis by the accq-tag method was performed using concentrated Accq-tag Eluent A (Waters, USA). All solutions were prepared using Milli-Q water, and standard solutions were stored at +4° C.

Example 8

Cloning of IDO Genes from *Bacillus cereus* ATCC 14597, *B. thurigiensis* AKU238, and *B. weihenstephanensis* KBAB4

(1) Preparation of Chromosomal DNA

*Bacillus cereus* ATCC 14579, *B. thurigiensis* AKU238, and *B. weihenstephanensis* KBAB4 were each cultivated overnight at 28° C. in 5 ml of LB medium (pre-culture). By using 1.5 ml of the culture broth as a seed, a main culture was carried out in 50 ml of LB medium. After cultivation up to the logarithmic growth phase, cells were harvested from 50 ml of the culture broth by centrifugation (12000×g, 4° C., 15 min). From these cells, chromosomal DNA was prepared according to a known method.

(2) Isolation of the IDO Genes by PCR

Based on the published genomic sequence information about *B. cereus* ATCC 14579 (GenBank accession No. AE016877), the following primers were synthesized:

```
CATATGGAGGTTTTTATAATGACGTTTGTT    (SEQ ID NO: 10)

CTCGAGTTTTGTCTCCTTATAAGAAAATGT    (SEQ ID NO: 11)
```

By using the prepared primers and chromosomal DNA of *B. cereus* ATCC 14578 as the template, amplification by PCR was carried out with PrimeSTAR (TaKaRa) under the following conditions: 30 cycles for 10 seconds at 98° C., 15 seconds at 52° C. and 1 minute at 72° C.

The PCR product was subjected to agarose gel electrophoresis and a fragment of about 750 bp was amplified. The DNA fragment was collected, digested with NdeI and XhoI endonucleases, and cloned into the expression vector pET21b (Novagene) which had been digested with the same endonucleases. Then, the nucleotide sequence was determined and the corresponding amino acid sequence was deduced (SEQ ID NOS: 12 and 13). As a result, it was confirmed that the ido gene is homologous to the obtained DNA fragment. The homology at nucleotide sequence level was 98% relative to both the ido gene from *B. thuringiensis israelensis* ATCC 35646 and the ido gene from *B. thuringiensis* 2-e-2.

The ido gene from *B. thuringiensis* AKU238 was cloned using the same primers (SEQ ID NOS: 14 and 15) which were used to clone the ido gene from *B. thuringiensis* 2-e-2 (SEQ ID NOS: 16 and 17). The homology at nucleotide sequence level was 98% relative to both the ido gene from *B. thuringiensis israelensis* ATCC 35646 and the ido gene from *B. thuringiensis* 2-e-2.

```
CATATGAAAATGAGTGGCTTTAGCATAGAA    (SEQ ID NO: 14)

CTCGAGTTTTGTCTCCTTATAAGAAAATGT    (SEQ ID NO: 15)
```

The ido gene from *B. weihenstephanensis* KBAB4 was cloned using primers based on the published genomic sequence (GenBank accession No. NZ_AAOY01000001 (SEQ ID NOS: 18 and 19). PCR was used to clone an ido gene, which was sequenced in a similar manner to the above (SEQ ID NOS: 20 and 21). The homology at nucleotide sequence level was 78% relative to both the ido gene from *B. thuringiensis israelensis* ATCC 35646 and the ido gene from *B. thuringiensis* 2-e-2.

```
CATATGCTAACAACAGTTTCTAATAAGACA    (SEQ ID NO: 18)

CTCGAGTTTTGGCTCCTTATAAGAAAACGT    (SEQ ID NO: 19)
```

Example 9

Expression of ido Genes in *E. coli* and Production of HIL from Ile (1) Expression of ido Genes in *E. coli*

The plasmid expressing the ido gene from *B. cereus* ATCC 14579, *B. thuringiensis* AKU238, or *B. weihenstephanensis* KBAB4, which was constructed in Example 8, was introduced into *E. coli* Rosetta2 (DE3), and the transformants were cultivated with shaking in LB medium supplemented with 50 μg/ml ampicillin (preculture). By seeding the preculture broth in 50 ml LB medium at 1%, the main culture was carried out at 37° C. 2 hours after the start of the cultivation, IPTG was added to a final concentration of 1 mM, and the cultivation was carried out for an additional 3 hours. After completion of the cultivation, the cells were harvested, washed, suspended in 1 ml of 20 mM Tris-HCl (pH 7.6), and disrupted with a sonicator (INSONATOR 201M, KUBOTA). The lysate was centrifuged at 15000 rpm for 10 minutes, and the supernatant was used as a crude enzyme solution.

(2) Production of HIL from Ile and the Crude Enzyme Solution

By using the crude enzyme solution prepared in (1), the conversion of Ile to HIL was measured. The reaction mixture is described below. The reaction mixture was reacted with shaking (300 rpm) at 28° C. for 3 hours, and then the amount of HIL produced was determined by HPLC. The results are shown in Table 14.

| Reaction mixture: | |
|---|---|
| Cell lysate (Ultrasonic disruption) | 500 μl |
| 2% Ile | 100 μl |
| 1 M α-KG | 5 μl |
| 1 M Ascorbate | 5 μl |
| 0.1 M $FeCl_2$ | 10 μl |
| 1 M KPB (pH 6) | 100 μl |
| Total | 1 ml |

TABLE 14

Amount of HIL produced from Ile

| | HIL (μM) |
|---|---|
| *B. thuringiensis israelensis* ATCC35646 | 2150 |
| *B. thuringiensis* 2e2 | 2321 |
| *B. thuringiensis* AKU238 | 2016 |
| *B. cereus* ATCC 14579 | 90 |
| *B. weihenstephanensis* KBAB4 | 3116 |
| control (pET21b) | 11 |

When cells expressing the ido gene from *B. cereus* ATCC 14579, and when the plasmid expressing the ido gene from *B. thuringiensis* AKU238 or *B. weihenstephanensis* KBAB4, were used, HIL was clearly produced. Thus, it was confirmed that these genes are useful in HIL production.

EXPLANATION OF SEQUENCES

1: Nucleotide sequence of IDO gene from *B. thuringiensis* strain 2-e-2
2: Amino acid sequence of IDO from *B. thuringiensis* strain 2-e-2
3: Primer svs 170; for amplification of IDO gene
4: Primer svs 169; for amplification of IDO gene
5: N-Terminal sequence of IDO from *B. thuringiensis* strain 2-e-2
6: IDO conserved sequence among *Bacillus* genus
7: Nucleotide sequence of IDO gene from *B. thuringiensis* strain ATCC 35646
8: Amino acid sequence of IDO from *B. thuringiensis* strain ATCC 35646
9: 16S rDNA nucleotide sequence of *B. thuringiensis* strain 2-e-2
10: Primer for amplification of IDO gene from *B. cereus* ATCC 14579
11: Primer for amplification of IDO gene from *B. cereus* ATCC 14579
12: Nucleotide sequence of IDO gene from *B. cereus* ATCC 14579
13: Amino acid sequence of IDO from *B. cereus* ATCC 14579
14: Primer for amplification of IDO gene from *B. thuringiensis* AKU238
15: Primer for amplification of IDO gene from *B. thuringiensis* AKU238
16: Nucleotide sequence of IDO gene from *B. thuringiensis* AKU238
17: Amino acid sequence of IDO from *B. thuringiensis* AKU238
18: Primer for amplification of IDO gene from *B. weihenstephanensis* KBAB4
19: Primer for amplification of IDO gene from *B. weihenstephanensis* KBAB4
20: Nucleotide sequence of IDO gene from *B. weihenstephanensis* KBAB4
21: Amino acid sequence of IDO from *B. weihenstephanensis* KBAB4

INDUSTRIAL APPLICABILITY

According to the present invention, a method is provided for producing 4-hydroxyisoleucine using an enzyme derived from a microorganism and catalyzing production of 4-hydroxyisoleucine by direct hydroxylation of isoleucine. The present invention is extremely useful in the fields of pharmaceuticals and food.

The L-isoleucine dioxygenase described herein is a novel dioxygenase that catalyzes the hydroxylation of L-isoleucine, and may be used to synthesize (2S,3R,4S)-4-hydroxy-L-isoleucine. This compound is useful as a component of pharmaceutical compositions with insulinotropic activity.

The invention claimed is:

1. An isolated dioxygenase which has the following properties and is able to be isolated from *Bacillus thuringiensis:*

(a) requires oxygen, $Fe^{2+}$, ascorbic acid and 2-oxoglutaric acid, (b) has an optimum reaction pH of 5 to 8, (c) has an optimum reaction temperature of 45° C. or lower, (d) is inactivated at 50° C. or higher, (e) is inhibited by EDTA, $Cu^{2+}$, and $Zn^{2+}$, (f) comprises one or more subunits having a molecular weight of 29,000±2,000 as measured by sodium dodecylsulfate-polyacrylamide gel electrophoresis, (g) comprises the amino acid sequence of SEQ ID NO: 5 at the N-terminus.

2. An isolated protein selected from the group consisting of:

(a) a protein comprising the amino acid sequence of SEQ ID No: 2;

(b) a protein comprising the amino acid sequence of SEQ ID No: 2, but which includes one to 13 substitutions, deletions, insertions, additions, or inversions of one to 13 amino acids, and has L-isoleucine dioxygenase activity; and (c) a protein that is at least 98% homologous to the amino acid sequence of SEQ ID No: 2 and has L-isoleucine dioxygenase activity.

3. An isolated protein comprising:

(A) the ability to catalyze the production of (2S,3R,4S)-4-hydroxy-L-isoleucine by hydroxylation of L-isoleucine, wherein $Fe^{2+}$ and 2-oxoglutaric acid are essential for said ability, and (B) a molecular weight as measured by SDS-PAGE of about 29±2.0 kDa, wherein the protein is able to be isolated from *Bacillus thuringiensis.*

* * * * *

SEQUENCE LISTING

```
<160> NUMBER OF SEQ ID NOS: 51

<210> SEQ ID NO 1
<211> LENGTH: 717
<212> TYPE: DNA
<213> ORGANISM: Bacillus thuringiensis
<220> FEATURE:
<221> NAME/KEY: CDS
<222> LOCATION: (1)..(717)
<223> OTHER INFORMATION:

<400> SEQUENCE: 1 aaa atg agt ggc ttt agc ata gaa gaa aag gta cat gaa ttt gaa tct        48
Lys Met Ser Gly Phe Ser Ile Glu Glu Lys Val His Glu Phe Glu Ser
1               5                   10                  15 aaa ggg ttt ctt gaa atc tca aat gaa atc ttt tta caa gag gaa gag        96
Lys Gly Phe Leu Glu Ile Ser Asn Glu Ile Phe Leu Gln Glu Glu Glu
                20                  25                  30 aat cat agt tta tta aca caa gca cag tta gat tat tat aat ttg gaa       144
Asn His Ser Leu Leu Thr Gln Ala Gln Leu Asp Tyr Tyr Asn Leu Glu
            35                  40                  45 gat gat gcg tac ggt gaa tgc cgt gct aga tct tat tca agg tat ata       192
Asp Asp Ala Tyr Gly Glu Cys Arg Ala Arg Ser Tyr Ser Arg Tyr Ile
        50                  55                  60 aag tat gtt gat tca cca gat tat att tta gat aat agt aat gat tac       240
Lys Tyr Val Asp Ser Pro Asp Tyr Ile Leu Asp Asn Ser Asn Asp Tyr
65                  70                  75                  80 ttc caa tct aaa gaa tat aac tat gat gat ggc ggg aaa gtt aga cag       288
Phe Gln Ser Lys Glu Tyr Asn Tyr Asp Asp Gly Gly Lys Val Arg Gln
                85                  90                  95 ttc aat agc ata aat gat agc ttt tta tgt aat cct tta att caa aat       336
```

```
Phe Asn Ser Ile Asn Asp Ser Phe Leu Cys Asn Pro Leu Ile Gln Asn
                100                 105                 110 atc gtg cgt ttc gat act gag ttt gca ttt aaa aca aat ata ata gat      384
Ile Val Arg Phe Asp Thr Glu Phe Ala Phe Lys Thr Asn Ile Ile Asp
            115                 120                 125 aaa agt aaa gat tta att ata ggc tta cat caa gta aga tat aaa gct      432
Lys Ser Lys Asp Leu Ile Ile Gly Leu His Gln Val Arg Tyr Lys Ala
        130                 135                 140 act aaa gaa aga cca tct ttt agt tca cct att tgg tta cat aaa gat      480
Thr Lys Glu Arg Pro Ser Phe Ser Ser Pro Ile Trp Leu His Lys Asp
145                 150                 155                 160 gat gaa cca gta gta ttt tta cac ctt atg aat tta agt aat aca gct      528
Asp Glu Pro Val Val Phe Leu His Leu Met Asn Leu Ser Asn Thr Ala
                165                 170                 175 atc ggc gga gat aat tta ata gct aat tct cct cgg gaa att aat cag      576
Ile Gly Gly Asp Asn Leu Ile Ala Asn Ser Pro Arg Glu Ile Asn Gln
            180                 185                 190 ttt ata agt ttg aag gag cct tta gaa act tta gta ttt gga caa aag      624
Phe Ile Ser Leu Lys Glu Pro Leu Glu Thr Leu Val Phe Gly Gln Lys
        195                 200                 205 gtc ttc cat gcc gta acg cca ctt gga aca gaa tgt agt acg gag gct      672
Val Phe His Ala Val Thr Pro Leu Gly Thr Glu Cys Ser Thr Glu Ala
210                 215                 220 ttt cgt gat att tta tta gta aca ttt tct tat aag gag aca aaa          717
Phe Arg Asp Ile Leu Leu Val Thr Phe Ser Tyr Lys Glu Thr Lys
225                 230                 235

<210> SEQ ID NO 2
<211> LENGTH: 239
<212> TYPE: PRT
<213> ORGANISM: Bacillus thuringiensis

<400> SEQUENCE: 2

Lys Met Ser Gly Phe Ser Ile Glu Glu Lys Val His Glu Phe Glu Ser
1               5                   10                  15

Lys Gly Phe Leu Glu Ile Ser Asn Glu Ile Phe Leu Gln Glu Glu Glu
            20                  25                  30

Asn His Ser Leu Leu Thr Gln Ala Gln Leu Asp Tyr Tyr Asn Leu Glu
        35                  40                  45

Asp Asp Ala Tyr Gly Glu Cys Arg Ala Arg Ser Tyr Ser Arg Tyr Ile
    50                  55                  60

Lys Tyr Val Asp Ser Pro Asp Tyr Ile Leu Asp Asn Ser Asn Asp Tyr
65                  70                  75                  80

Phe Gln Ser Lys Glu Tyr Asn Tyr Asp Asp Gly Gly Lys Val Arg Gln
                85                  90                  95

Phe Asn Ser Ile Asn Asp Ser Phe Leu Cys Asn Pro Leu Ile Gln Asn
            100                 105                 110

Ile Val Arg Phe Asp Thr Glu Phe Ala Phe Lys Thr Asn Ile Ile Asp
        115                 120                 125

Lys Ser Lys Asp Leu Ile Ile Gly Leu His Gln Val Arg Tyr Lys Ala
    130                 135                 140

Thr Lys Glu Arg Pro Ser Phe Ser Ser Pro Ile Trp Leu His Lys Asp
145                 150                 155                 160

Asp Glu Pro Val Val Phe Leu His Leu Met Asn Leu Ser Asn Thr Ala
                165                 170                 175

Ile Gly Gly Asp Asn Leu Ile Ala Asn Ser Pro Arg Glu Ile Asn Gln
            180                 185                 190

Phe Ile Ser Leu Lys Glu Pro Leu Glu Thr Leu Val Phe Gly Gln Lys
```

```
                195                 200                 205
Val Phe His Ala Val Thr Pro Leu Gly Thr Glu Cys Ser Thr Glu Ala
    210                 215                 220

Phe Arg Asp Ile Leu Leu Val Thr Phe Ser Tyr Lys Glu Thr Lys
225                 230                 235

<210> SEQ ID NO 3
<211> LENGTH: 65
<212> TYPE: DNA
<213> ORGANISM: Artificial sequence
<220> FEATURE:
<223> OTHER INFORMATION: primer SVS 170

<400> SEQUENCE: 3
ctctagagga tccttaagaa ggagatatac catgaaaatg agtggcttta gcatagaaga    60
aaagg                                                                65

<210> SEQ ID NO 4
<211> LENGTH: 35
<212> TYPE: DNA
<213> ORGANISM: Artificial sequence
<220> FEATURE:
<223> OTHER INFORMATION: primer SVS 169

<400> SEQUENCE: 4
gaattcgagc tcttattttg tctccttata agaaa                               35

<210> SEQ ID NO 5
<211> LENGTH: 20
<212> TYPE: PRT
<213> ORGANISM: Bacillus thuringiensis

<400> SEQUEN

```
Phe Xaa Ser Ile Xaa Asp Xaa Phe Leu Xaa Asn Xaa Leu Ile Xaa Xaa
            100                 105                 110

Ile Val Arg Phe Asp Xaa Glu Phe Ala Xaa Xaa Thr Asn Ile Xaa Asp
        115                 120                 125

Thr Ser Lys Asp Leu Xaa Ile Gly Leu His Gln Val Arg Tyr Lys Ala
130                 135                 140

Thr Xaa Glu Xaa Pro Ser Phe Ser Pro Ile Trp Leu His Lys Asp
145                 150                 155                 160

Asp Glu Pro Xaa Val Phe Leu His Leu Met Asn Leu Ser Asn Thr Ala
                165                 170                 175

Xaa Gly Gly Asp Asn Leu Ile Ala Asn Ser Pro Arg Glu Ile Asn Xaa
        180                 185                 190

Xaa Ile Ser Leu Lys Xaa Pro Leu Glu Thr Leu Val Phe Gly Gln Lys
        195                 200                 205

Val Phe His Ala Val Thr Pro Leu Gly Thr Glu Cys Xaa Thr Glu Ala
210                 215                 220

Xaa Arg Asp Ile Leu Leu Val Thr Phe Ser Tyr Lys Glu Xaa Lys
225                 230                 235

<210> SEQ ID NO 7
<211> LENGTH: 720
<212> TYPE: DNA
<213> ORGANISM: Bacillus thuringiensis
<220> FEATURE:
<221> NAME/KEY: CDS
<222> LOCATION: (1)..(720)

<400> SEQUENCE: 7 aaa atg agt ggc ttt agc ata gaa gaa aag gta cat gaa ttt gaa tct    48
Lys Met Ser Gly Phe Ser Ile Glu Glu Lys Val His Glu Phe Glu Ser
1               5                   10                  15 aaa ggg ttt ctt gaa atc tca aat gaa atc ttt tta caa gag gaa gag    96
Lys Gly Phe Leu Glu Ile Ser Asn Glu Ile Phe Leu Gln Glu Glu Glu
            20                  25                  30 aat cat agt tta tta aca caa gca cag tta gat tat tat aat ttg gaa   144
Asn His Ser Leu Leu Thr Gln Ala Gln Leu Asp Tyr Tyr Asn Leu Glu
        35                  40                  45 gat gat gcg tac ggt gaa tgc cgt gct aga tct tat tca agg tat ata   192
Asp Asp Ala Tyr Gly Glu Cys Arg Ala Arg Ser Tyr Ser Arg Tyr Ile
    50                  55                  60 aag tat gtt gat tca cca gat tat att tta gat aat agt aat gat tac   240
Lys Tyr Val Asp Ser Pro Asp Tyr Ile Leu Asp Asn Ser Asn Asp Tyr
65                  70                  75                  80 ttc caa tct aaa gaa tat aac tat gat gat ggc ggg aaa gtt aga cag   288
Phe Gln Ser Lys Glu Tyr Asn Tyr Asp Asp Gly Gly Lys Val Arg Gln
                85                  90                  95 ttc aat agc ata aat gat agc ttt ttg tgt aat cct tta att caa aat   336
Phe Asn Ser Ile Asn Asp Ser Phe Leu Cys Asn Pro Leu Ile Gln Asn
            100                 105                 110 atc gtg cat ttc gat act gag ttt gca ttt aaa aca aat ata ata gat   384
Ile Val His Phe Asp Thr Glu Phe Ala Phe Lys Thr Asn Ile Ile Asp
        115                 120                 125 aaa agt aaa gat tta att ata ggc tta cat caa gta aga tat aaa gct   432
Lys Ser Lys Asp Leu Ile Ile Gly Leu His Gln Val Arg Tyr Lys Ala
130                 135                 140 act aaa gaa aga cca tct ttt agt tca cct att tgg tta cat aaa gat   480
Thr Lys Glu Arg Pro Ser Phe Ser Ser Pro Ile Trp Leu His Lys Asp
145                 150                 155                 160 gat gaa cca gta gtg ttt tta cac ctt atg aat tta agt aat aca gct   528
Asp Glu Pro Val Val Phe Leu His Leu Met Asn Leu Ser Asn Thr Ala
```

```
                 165                 170                 175
atc ggc gga gat aat tta ata gct aat tct cct cgg gaa att aat cag      576
Ile Gly Gly Asp Asn Leu Ile Ala Asn Ser Pro Arg Glu Ile Asn Gln
            180                 185                 190 ttt ata agt ttg aag gag ccg tta gaa act tta gta ttt gga caa aag      624
Phe Ile Ser Leu Lys Glu Pro Leu Glu Thr Leu Val Phe Gly Gln Lys
        195                 200                 205 gtc ttc cat gcc gta acg cca ctt gga aca gaa tgt agt acg gag gct      672
Val Phe His Ala Val Thr Pro Leu Gly Thr Glu Cys Ser Thr Glu Ala
    210                 215                 220 ttt cgt gat att tta tta gta aca ttt tct tat aag gag aca aaa taa      720
Phe Arg Asp Ile Leu Leu Val Thr Phe Ser Tyr Lys Glu Thr Lys
225                 230                 235

<210> SEQ ID NO 8
<211> LENGTH: 239
<212> TYPE: PRT
<213> ORGANISM: Bacillus thuringiensis

<400> SEQUENCE: 8

Lys Met Ser Gly Phe Ser Ile Glu Glu Lys Val His Glu Phe Glu Ser
1               5                   10                  15

Lys Gly Phe Leu Glu Ile Ser Asn Glu Ile Phe Leu Gln Glu Glu Glu
            20                  25                  30

Asn His Ser Leu Leu Thr Gln Ala Gln Leu Asp Tyr Tyr Asn Leu Glu
        35                  40                  45

Asp Asp Ala Tyr Gly Glu Cys Arg Ala Arg Ser Tyr Ser Arg Tyr Ile
    50                  55                  60

Lys Tyr Val Asp Ser Pro Asp Tyr Ile Leu Asp Asn Ser Asn Asp Tyr
65                  70                  75                  80

Phe Gln Ser Lys Glu Tyr Asn Tyr Asp Asp Gly Gly Lys Val Arg Gln
                85                  90                  95

Phe Asn Ser Ile Asn Asp Ser Phe Leu Cys Asn Pro Leu Ile Gln Asn
            100                 105                 110

Ile Val His Phe Asp Thr Glu Phe Ala Phe Lys Thr Asn Ile Ile Asp
        115                 120                 125

Lys Ser Lys Asp Leu Ile Ile Gly Leu His Gln Val Arg Tyr Lys Ala
    130                 135                 140

Thr Lys Glu Arg Pro Ser Phe Ser Ser Pro Ile Trp Leu His Lys Asp
145                 150                 155                 160

Asp Glu Pro Val Val Phe Leu His Leu Met Asn Leu Ser Asn Thr Ala
                165                 170                 175

Ile Gly Gly Asp Asn Leu Ile Ala Asn Ser Pro Arg Glu Ile Asn Gln
            180                 185                 190

Phe Ile Ser Leu Lys Glu Pro Leu Glu Thr Leu Val Phe Gly Gln Lys
        195                 200                 205

Val Phe His Ala Val Thr Pro Leu Gly Thr Glu Cys Ser Thr Glu Ala
    210                 215                 220

Phe Arg Asp Ile Leu Leu Val Thr Phe Ser Tyr Lys Glu Thr Lys
225                 230                 235

<210> SEQ ID NO 9
<211> LENGTH: 537
<212> TYPE: DNA
<213> ORGANISM: Bacillus thuringiensis

<400> SEQUENCE: 9
tggagagttt gatcctggct caggatgaac gctggcggcg tgcctaatac atgcaagtcg      60
```
agcgaatgga ttgagagctt gctctcaaga agttagcggc ggacgggtga gtaacacgtg 120
ggtaacctgc ccataagact gggataactc cgggaaaccg gggctaatac cggataacat 180
tttgaactgc atggttcgaa attgaaaggc ggcttcggct gtcacttatg gatggacccg 240
cgtcgcatta gctagttggt gaggtaacgg ctcaccaagg caacgatgcg tagccgacct 300
gagagggtga tcggccacac tgggactgag acacggccca gactcctacg ggaggcagca 360
gtagggaatc ttccgcaatg gacgaaagtc tgacggagca acgccgcgtg agtgatgaag 420
gctttcgggt cgtaaaactc tgttgttagg gaagaacaag tgctagttga ataagctggc 480
accttgacgg tacctaacca gaaagccacg gctaactacg tgccagcagc cgcggta 537

<210> SEQ ID NO 10
<211> LENGTH: 30
<212> TYPE: DNA
<213> ORGANISM: Artificial Sequence
<220> FEATURE:
<223> OTHER INFORMATION: Primer

<400> SEQUENCE: 10
catatggagg tttttataat gacgtttgtt 30

<210> SEQ ID NO 11
<211> LENGTH: 30
<212> TYPE: DNA
<213> ORGANISM: Artificial Sequence
<220> FEATURE:
<223> OTHER INFORMATION: Primer

<400> SEQUENCE: 11
ctcgagtttt gtctccttat aagaaaatgt 30

<210> SEQ ID NO 12
<211> LENGTH: 753
<212> TYPE: DNA
<213> ORGANISM: Bacillus cereus

<400> SEQUENCE: 12
gtggaggttt ttataatgac gtttgttctt agtaaaatga atgggtttag catagaagaa 60
aaggtacatg aatttgaatc taaaggattc cttgaaatct caaatgaaat ctttttacaa 120
gaggaagaga atcatcgttt attaacacaa gcacagttag attattataa tttggaagat 180
gatgcgtacg gtgaatgccg tgctagatct tattcaaggt atataaagta tgttgattca 240
ccagattata ttttagataa tagtaatgat tacttccaat ctaaagaata taactatgac 300
gatggcggga aagttagaca gttcaatagc ataaatgata gctttttatg caatccttta 360
attcaaaata tcgtgcgttt cgatactgaa tttgcattta aaacaaatat aatagataca 420
agtaaagact taattatagg tttacatcaa gtaagatata aagctactaa agaaagacca 480
tcttttagtt cacctatttg gttacataaa gatgatgaac cagtagtatt tttacacctt 540
atgaatttaa gtaatacagc tattggtgga gataatttaa tagctaattc tcctcgagaa 600
attaatcagt ttataagttt gaaggagcct ttagaaactt tagtatttgg acaaaaggtc 660
ttccatgccg taacgccact tggaacagaa tgtagtacgg aggcttttcg tgatatttta 720
ttagtaacat tttcttataa ggagacaaaa tga 753

<210> SEQ ID NO 13
<211> LENGTH: 250
<212> TYPE: PRT
<213> ORGANISM: Bacillus cereus

<400> SEQUENCE: 13

| | | | | | | | | | | | | | | | |
|---|---|---|---|---|---|---|---|---|---|---|---|---|---|---|---|
|Met|Glu|Val|Phe|Ile|Met|Thr|Phe|Val|Leu|Ser|Lys|Met|Asn|Gly|Phe|
|1| | | |5| | | | |10| | | | |15| |
|Ser|Ile|Glu|Glu|Lys|Val|His|Glu|Phe|Glu|Ser|Lys|Gly|Phe|Leu|Glu|
| | | |20| | | | |25| | | | |30| | |
|Ile|Ser|Asn|Glu|Ile|Phe|Leu|Gln|Glu|Glu|Asn|His|Arg|Leu|Leu| |
| | |35| | | | |40| | | | |45| | | |
|Thr|Gln|Ala|Gln|Leu|Asp|Tyr|Tyr|Asn|Leu|Glu|Asp|Asp|Ala|Tyr|Gly|
| |50| | | | |55| | | | |60| | | | |
|Glu|Cys|Arg|Ala|Arg|Ser|Tyr|Ser|Arg|Tyr|Ile|Lys|Tyr|Val|Asp|Ser|
|65| | | | |70| | | | |75| | | | |80|
|Pro|Asp|Tyr|Ile|Leu|Asp|Asn|Ser|Asn|Asp|Tyr|Phe|Gln|Ser|Lys|Glu|
| | | | |85| | | | |90| | | | |95| |
|Tyr|Asn|Tyr|Asp|Asp|Gly|Gly|Lys|Val|Arg|Gln|Phe|Asn|Ser|Ile|Asn|
| | | |100| | | | |105| | | | |110| | |
|Asp|Ser|Phe|Leu|Cys|Asn|Pro|Leu|Ile|Gln|Asn|Ile|Val|Arg|Phe|Asp|
| | |115| | | | |120| | | | |125| | | |
|Thr|Glu|Phe|Ala|Phe|Lys|Thr|Asn|Ile|Ile|Asp|Thr|Ser|Lys|Asp|Leu|
| |130| | | | |135| | | | |140| | | | |
|Ile|Ile|Gly|Leu|His|Gln|Val|Arg|Tyr|Lys|Ala|Thr|Lys|Glu|Arg|Pro|
|145| | | | |150| | | | |155| | | | |160|
|Ser|Phe|Ser|Ser|Pro|Ile|Trp|Leu|His|Lys|Asp|Asp|Glu|Pro|Val|Val|
| | | | |165| | | | |170| | | | |175| |
|Phe|Leu|His|Leu|Met|Asn|Leu|Ser|Asn|Thr|Ala|Ile|Gly|Gly|Asp|Asn|
| | | |180| | | | |185| | | | |190| | |
|Leu|Ile|Ala|Asn|Ser|Pro|Arg|Glu|Ile|Asn|Gln|Phe|Ile|Ser|Leu|Lys|
| | |195| | | | |200| | | | |205| | | |
|Glu|Pro|Leu|Glu|Thr|Leu|Val|Phe|Gly|Gln|Lys|Val|Phe|His|Ala|Val|
| |210| | | | |215| | | | |220| | | | |
|Thr|Pro|Leu|Gly|Thr|Glu|Cys|Ser|Thr|Glu|Ala|Phe|Arg|Asp|Ile|Leu|
|225| | | | |230| | | | |235| | | | |240|
|Leu|Val|Thr|Phe|Ser|Tyr|Lys|Glu|Thr|Lys| | | | | | |
| | | | |245| | | | |250| | | | | | |

<210> SEQ ID NO 14
<211> LENGTH: 30
<212> TYPE: DNA
<213> ORGANISM: Artificial Sequence
<220> FEATURE:
<223> OTHER INFORMATION: Primer

<400> SEQUENCE: 14
catatgaaaa tgagtggctt tagcatagaa        30

<210> SEQ ID NO 15
<211> LENGTH: 30
<212> TYPE: DNA
<213> ORGANISM: Artificial Sequence
<220> FEATURE:
<223> OTHER INFORMATION: Primer

<400> SEQUENCE: 15
ctcgagtttt gtctccttat aagaaaatgt        30

<210> SEQ ID NO 16
<211> LENGTH: 753
<212> TYPE: DNA
<213> ORGANISM: Bacillus thuringiensis -continued

<400> SEQUENCE: 16

```
gtggaggttt ttataatgac gtttgttctt agtaaaatga gtggctttag catagaagaa    60
aaggtacatg aatttgaatc taaaggattc cttgaaattt caaatgaaat cttttttacaa  120
gaggaagaga atcatcgtct attaacacaa gcacagttag attattataa tttggaagat  180
gatgcatacg gtgaatgtcg tgctagatct tattcaaggt atataaagta tgttgattca  240
ccagattata ttttagataa tagtaatgat tacttccaat ctaaagaata taactatgac  300
gatggcggga agttagaca gttcaatagc ataaatgata gcttttatg taatccttta  360
attcaaaata tcgtgcgctt cgatactgaa tttgcattta aaacaaatat aatagataca  420
agtaaagact taattatagg tttacatcaa gtaagatata aagctactaa agaaagacca  480
tcttttagtt cacctatttg gttacataaa gatgatgaac cagtagtgtt tttacacctt  540
atgaatttaa gtaatacagc tattggtgga gataatttaa tagctaattc tcctcgggaa  600
attaatcagt ttataagttt gaaggagcct ttagaaactt tagtatttgg acaaaaggtc  660
ttccatgccg taacgccact tggaacagaa tgtagtacgg aggcttttcg tgatatttta  720
ttagtaacat tttcttataa ggagacaaaa tga                                753
```

<210> SEQ ID NO 17
<211> LENGTH: 250
<212> TYPE: PRT
<213> ORGANISM: Bacillus thuringiensis

<400> SEQUENCE: 17

```
Met Glu Val Phe Ile Met Thr Phe Val Leu Ser Lys Met Ser Gly Phe
1               5                   10                  15

Ser Ile Glu Glu Lys Val His Glu Phe Glu Ser Lys Gly Phe Leu Glu
            20                  25                  30

Ile Ser Asn Glu Ile Phe Leu Gln Glu Glu Asn His Arg Leu Leu
        35                  40                  45

Thr Gln Ala Gln Leu Asp Tyr Tyr Asn Leu Glu Asp Asp Ala Tyr Gly
    50                  55                  60

Glu Cys Arg Ala Arg Ser Tyr Ser Arg Tyr Ile Lys Tyr Val Asp Ser
65                  70                  75                  80

Pro Asp Tyr Ile Leu Asp Asn Ser Asn Asp Tyr Phe Gln Ser Lys Glu
                85                  90                  95

Tyr Asn Tyr Asp Asp Gly Gly Lys Val Arg Gln Phe Asn Ser Ile Asn
            100                 105                 110

Asp Ser Phe Leu Cys Asn Pro Leu Ile Gln Asn Ile Val Arg Phe Asp
        115                 120                 125

Thr Glu Phe Ala Phe Lys Thr Asn Ile Ile Asp Thr Ser Lys Asp Leu
    130                 135                 140

Ile Ile Gly Leu His Gln Val Arg Tyr Lys Ala Thr Lys Glu Arg Pro
145                 150                 155                 160

Ser Phe Ser Ser Pro Ile Trp Leu His Lys Asp Asp Glu Pro Val Val
                165                 170                 175

Phe Leu His Leu Met Asn Leu Ser Asn Thr Ala Ile Gly Gly Asp Asn
            180                 185                 190

Leu Ile Ala Asn Ser Pro Arg Glu Ile Asn Gln Phe Ile Ser Leu Lys
        195                 200                 205

Glu Pro Leu Glu Thr Leu Val Phe Gly Gln Lys Val Phe His Ala Val
    210                 215                 220

Thr Pro Leu Gly Thr Glu Cys Ser Thr Glu Ala Phe Arg Asp Ile Leu
```

```
225                 230                 235                 240
Leu Val Thr Phe Ser Tyr Lys Glu Thr Lys
                245                 250

<210> SEQ ID NO 18
<211> LENGTH: 30
<212> TYPE: DNA
<213> ORGANISM: Artificial Sequence
<220> FEATURE:
<223> OTHER INFORMATION: Primer

<400> SEQUENCE: 18
catatgctaa caacagtttc taataagaca                                       30

<210> SEQ ID NO 19
<211> LENGTH: 30
<212> TYPE: DNA
<213> ORGANISM: Artificial Sequence
<220> FEATURE:
<223> OTHER INFORMATION: Primer

<400> SEQUENCE: 19
ctcgagtttt ggctccttat aagaaaacgt                                       30

<210> SEQ ID NO 20
<211> LENGTH: 741
<212> TYPE: DNA
<213> ORGANISM: Bacillus weihenstephanensis

<400> SEQUENCE: 20
atgctaacaa cagtttctaa taagacaagc agttttgacg tagaacaaaa ggtacatgaa      60
ttcgaatcaa atggatacat tcaaatcttt aatgatattt ttttacaaga tcaagaagat     120
caagcattac taacgaaagc acagttagac tactacagct acaaaacga cgcatatggc      180 gaatgtcgcg ctagagccta ttcaagatat ataaaatacg ctggttcttc agattatgtt     240
ctagatacag acaatggata tttccaatct gaagaatata attatgacga tggtgggaaa     300
attagaaatt tcaacagtat aacagatgaa ttttacata attcattaat tgagaaaatt      360
gttcgctttg atagtgaatt tgcatctaat acaaatatac ttgatacaag taaggatttg     420
gttataggtc tacatcaagt aagatataag gcaactagag aaaatccttc ttttagctct     480
ccaatttggc tacataagga tgatgagccg attgtctttt tacatctcat gaatttaagt     540
aatacagctc ttggcggaga caatctgatt gcaaacagcc tagggaaat taacaagctt      600 attagcttga aggatcccct agaaacttta gtatttggac aaaaggtatt ccacgctgta     660
acaccactag aacagagtg taatacagaa gccttacgtg catttttatt agtaacgttt      720
tcttataagg agccaaaatg a                                              741

<210> SEQ ID NO 21
<211> LENGTH: 246
<212> TYPE: PRT
<213> ORGANISM: Bacillus weihenstephanensis

<400> SEQ

```
Leu Asp Tyr Tyr Ser Leu Gln Asn Asp Ala Tyr Gly Glu Cys Arg Ala
         50                  55                  60

Arg Ala Tyr Ser Arg Tyr Ile Lys Tyr Ala Gly Ser Ser Asp Tyr Val
 65                  70                  75                  80

Leu Asp Thr Asp Asn Gly Tyr Phe Gln Ser Glu Tyr Asn Tyr Asp
                 85                  90                  95

Asp Gly Gly Lys Ile Arg Asn Phe Asn Ser Ile Thr Asp Glu Phe Leu
            100                 105                 110

His Asn Ser Leu Ile Glu Lys Ile Val Arg Phe Asp Ser Glu Phe Ala
            115                 120                 125

Ser Asn Thr Asn Ile Leu Asp Thr Ser Lys Asp Leu Val Ile Gly Leu
        130                 135                 140

His Gln Val Arg Tyr Lys Ala Thr Arg Glu Asn Pro Ser Phe Ser Ser
145                 150                 155                 160

Pro Ile Trp Leu His Lys Asp Asp Glu Pro Ile Val Phe Leu His Leu
                165                 170                 175

Met Asn Leu Ser Asn Thr Ala Leu Gly Gly Asp Asn Leu Ile Ala Asn
            180                 185                 190

Ser Pro Arg Glu Ile Asn Lys Leu Ile Ser Leu Lys Asp Pro Leu Glu
        195                 200                 205

Thr Leu Val Phe Gly Gln Lys Val Phe His Ala Val Thr Pro Leu Gly
        210                 215                 220

Thr Glu Cys Asn Thr Glu Ala Leu Arg Asp Ile Leu Leu Val Thr Phe
225                 230                 235                 240

Ser Tyr Lys Glu Pro Lys
                245

<210> SEQ ID NO 22
<211> LENGTH: 9
<212> TYPE: PRT
<213> ORGANISM: Bacillus thuringiensis

<400> SEQUENCE: 22

Lys Val His Glu Phe Glu Ser Lys Gly
1               5

<210> SEQ ID NO 23
<211> LENGTH: 10
<212> TYPE: PRT
<213> ORGANISM: Bacillus thuringiensis

<400> SEQUENCE: 23

Arg Phe Asp Thr Glu Phe Ala Phe Lys Thr
1               5                  10

<210> SEQ ID NO 24
<211> LENGTH: 11
<212> TYPE: PRT
<213> ORGANISM: Bacillus thuringiensis

<400> SEQUENCE: 24

Lys Met Ser Gly Phe Ser Ile Glu Glu Lys Val
1               5                  10

<210> SEQ ID NO 25
<211> LENGTH: 11
<212> TYPE: PRT
<213> ORGANISM: Bacillus thuringiensis

<400> SEQUENCE: 25
```

```
Lys Glu Tyr Asn Tyr Asp Asp Gly Gly Lys Val
1               5                  10

<210> SEQ ID NO 26
<211> LENGTH: 11
<212> TYPE: PRT
<213> ORGANISM: Bacillus thuringiensis

<400> SEQUENCE: 26

Arg Glu Ile Asn Gln Phe Ile Ser Leu Lys Glu
1               5                  10

<210> SEQ ID NO 27
<211> LENGTH: 12
<212> TYPE: PRT
<213> ORGANISM: Bacillus thuringiensis

<400> SEQUENCE: 27

Lys Asp Leu Ile Ile Gly Leu His Gln Val Arg Tyr
1               5                  10

<210> SEQ ID NO 28
<211> LENGTH: 12
<212> TYPE: PRT
<213> ORGANISM: Bacillus thuringiensis

<400> SEQUENCE: 28

Arg Asp Ile Leu Leu Val Thr Phe Ser Tyr Lys Glu
1               5                  10

<210> SEQ ID NO 29
<211> LENGTH: 13
<212> TYPE: PRT
<213> ORGANISM: Bacillus thuringiensis

<400> SEQUENCE: 29

Lys Glu Pro Leu Glu Thr Leu Val Phe Gly Gln Lys Val
1               5                  10

<210> SEQ ID NO 30
<211> LENGTH: 15
<212> TYPE: PRT
<213> ORGANISM: Bacillus thuringiensis

<400> SEQUENCE: 30

Lys Glu Arg Pro Ser Phe Ser Ser Pro Ile Trp Leu His Lys Asp
1               5                  10                  15

<210> SEQ ID NO 31
<211> LENGTH: 20
<212> TYPE: PRT
<213> ORGANISM: Bacillus thuringiensis

<400> SEQUENCE: 31

Lys Thr Asn Ile Ile Asp Thr Ser Lys Asp Leu Ile Ile Gly Leu His
1               5                  10                  15

Gln Val Arg Tyr
            20

<210> SEQ ID NO 32
<211> LENGTH: 21
<212> TYPE: PRT
<213> ORGANISM: Bacillus thuringiensis

<400> SEQUENCE: 32
```

-continued

```
Lys Tyr Val Asp Ser Pro Asp Tyr Ile Leu Asp Asn Ser Asn Asp Tyr
1               5                   10                  15

Phe Gln Ser Lys Glu
            20

<210> SEQ ID NO 33
<211> LENGTH: 22
<212> TYPE: PRT
<213> ORGANISM: Bacillus thuringiensis

<400> SEQUENCE: 33

Arg Glu Ile Asn Gln Phe Ile Ser Leu Lys Glu Pro Leu Glu Thr Leu
1               5                   10                  15

Val Phe Gly Gln Lys Val
            20

<210> SEQ ID NO 34
<211> LENGTH: 42
<212> TYPE: DNA
<213> ORGANISM: Bacillus thuringiensis
<220> FEATURE:
<221> NAME/KEY: CDS
<222> LOCATION: (16)..(42)

<400> SEQUENCE: 34
gtggaggttt ttata atg acg ttt gtt ctt agt aaa atg agt                    42
               Met Thr Phe Val Leu Ser Lys Met Ser
                 1               5

<210> SEQ ID NO 35
<211> LENGTH: 9
<212> TYPE: PRT
<213> ORGANISM: Bacillus thuringiensis

<400> SEQUENCE: 35

Met Thr Phe Val Leu Ser Lys Met Ser
1               5

<210> SEQ ID NO 36
<211> LENGTH: 5
<212> TYPE: PRT
<213> ORGANISM: Artificial Sequence
<220> FEATURE:
<223> OTHER INFORMATION: SVS 170 leader

<400> SEQUENCE: 36

Thr Leu Glu Asp Pro
1               5

<210> SEQ ID NO 37
<211> LENGTH: 11
<212> TYPE: PRT
<213> ORGANISM: Artificial Sequence
<220> FEATURE:
<223> OTHER INFORMATION: SVS 170 N-terminus

<400> SEQUENCE: 37

Met Lys Met Ser Gly Phe Ser Ile Glu Glu Lys
1               5                   10

<210> SEQ ID NO 38
<211> LENGTH: 166
<212> TYPE: DNA
<213> ORGANISM: Artificial Sequence
<220> FEATURE:
<223> OTHER INFORMATION: pMW199-IDO(Lys, 32) expression module
<220> FEATURE:
```

```
<221> NAME/KEY: CDS
<222> LOCATION: (74)..(127)
<220> FEATURE:
<221> NAME/KEY: CDS
<222> LOCATION: (145)..(165)

<400> SEQUENCE: 38 ttacactttta tgcttccggc tcgtatgttg tgtggaattg tgagcggata acaatttcac    60
acaggaaaca gct atg acc atg att acg cca agc ttg cat gcc tgc agg      109
            Met Thr Met Ile Thr Pro Ser Leu His Ala Cys Arg
              1               5                  10 tcg act cta gag gat cct taagaaggag atatacc atg aaa atg agt ggc      159
Ser Thr Leu Glu Asp Pro                  Met Lys Met Ser Gly
         15                                    20 ttt agc a                                                            166
Phe Ser
     25

<210> SEQ ID NO 39
<211> LENGTH: 18
<212> TYPE: PRT
<213> ORGANISM: Artificial Sequence
<220> FEATURE:
<223> OTHER INFORMATION: pMW199-IDO(Lys, 32) expression module

<400> SEQUENCE: 39

Met Thr Met Ile Thr Pro Ser Leu His Ala Cys Arg Ser Thr Leu Glu
  1               5                  10                  15

Asp Pro

<210> SEQ ID NO 40
<211> LENGTH: 7
<212> TYPE: PRT
<213> ORGANISM: Artificial Sequence
<220> FEATURE:
<223> OTHER INFORMATION: pMW199-IDO(Lys, 32) expression module

<400> SEQUENCE: 40

Met Lys Met Ser Gly Phe Ser
  1               5

<210> SEQ ID NO 41
<211> LENGTH: 166
<212> TYPE: DNA
<213> ORGANISM: Artificial Sequence
<220> FEATURE:
<223> OTHER INFORMATION: pMW199-IDO(Lys, 23) expression module
<220> FEATURE:
<221> NAME/KEY: CDS
<222> LOCATION: (74)..(145)

<400> SEQUENCE: 41 ttacactttta tgcttccggc tcgtatgttg tgtggaattg tgagcggata acaatttcac    60
acaggaaaca gct atg acc atg att acg cca agc ttg cat gcc tgc agg      109
            Met Thr Met Ile Thr Pro Ser Leu His Ala Cys Arg
              1               5                  10 tcg act cta gag gat cct caa gaa gga gat ata aca tgaaaatgag          155
Ser Thr Leu Glu Asp Pro Gln Glu Gly Asp Ile Thr
         15                  20 tggctttagc a                                                         166

<210> SEQ ID NO 42
<211> LENGTH: 24
<212> TYPE: PRT
<213> ORGANISM: Artificial Sequence
```

```
<220> FEATURE:
<223> OTHER INFORMATION: pMW199-IDO(Lys, 23) expression module

<400> SEQUENCE: 42

Met Thr Met Ile Thr Pro Ser Leu His Ala Cys Arg Ser Thr Leu Glu
1               5                   10                  15

Asp Pro Gln Glu Gly Asp Ile Thr
            20

<210> SEQ ID NO 43
<211> LENGTH: 753
<212> TYPE: DNA
<213> ORGANISM: Artificial Sequence
<220> FEATURE:
<223> OTHER INFORMATION: pMW199-IDO(Lys, 23) BamHI-SacI
<220> FEATURE:
<221> NAME/KEY: CDS
<222> LOCATION: (25)..(744)

<400> SEQUENCE: 43
ggatcctcaa gaaggagata taac atg aaa atg agt ggc ttt agc ata gaa         51
                          Met Lys Met Ser Gly Phe Ser Ile Glu
                          1               5 gaa aag gta cat gaa ttt gaa tct aaa ggg ttt ctt gaa atc tca aat        99
Glu Lys Val His Glu Phe Glu Ser Lys Gly Phe Leu Glu Ile Ser Asn
 10              15                  20                  25 gaa atc ttt tta caa gag gaa gag aat cat agt tta tta aca caa gca      147
Glu Ile Phe Leu Gln Glu Glu Glu Asn His Ser Leu Leu Thr Gln Ala
            30                  35                  40 cag tta gat tat tat aat ttg gaa gat gat gcg tac ggt gaa tgc cgt      195
Gln Leu Asp Tyr Tyr Asn Leu Glu Asp Asp Ala Tyr Gly Glu Cys Arg
        45                  50                  55 gct aga tct tat tca agg tat ata aag tat gtt gat tca cca gat tat      243
Ala Arg Ser Tyr Ser Arg Tyr Ile Lys Tyr Val Asp Ser Pro Asp Tyr
    60                  65                  70 att tta gat aat agt aat gat tac ttc caa tct aaa gaa tat aac tat      291
Ile Leu Asp Asn Ser Asn Asp Tyr Phe Gln Ser Lys Glu Tyr Asn Tyr
75                  80                  85 gat gat ggc ggg aaa gtt aga cag ttc aat agc ata aat gat agc ttt      339
Asp Asp Gly Gly Lys Val Arg Gln Phe Asn Ser Ile Asn Asp Ser Phe
90                  95                 100                 105 tta tgt aat cct tta att caa aat atc gtg cgt ttc gat act gag ttt      387
Leu Cys Asn Pro Leu Ile Gln Asn Ile Val Arg Phe Asp Thr Glu Phe
                110                 115                 120 gca ttt aaa aca aat ata ata gat aaa agt aaa gat tta att ata ggc      435
Ala Phe Lys Thr Asn Ile Ile Asp Lys Ser Lys Asp Leu Ile Ile Gly
            125                 130                 135 tta cat caa gta aga tat aaa gct act aaa gaa aga cca tct ttt agt      483
Leu His Gln Val Arg Tyr Lys Ala Thr Lys Glu Arg Pro Ser Phe Ser
        140                 145                 150 tca cct att tgg tta cat aaa gat gat gaa cca gta gta ttt tta cac      531
Ser Pro Ile Trp Leu His Lys Asp Asp Glu Pro Val Val Phe Leu His
    155                 160                 165 ctt atg aat tta agt aat aca gct atc ggc gga gat aat tta ata gct      579
Leu Met Asn Leu Ser Asn Thr Ala Ile Gly Gly Asp Asn Leu Ile Ala
170                 175                 180                 185 aat tct cct cgg gaa att aat cag ttt ata agt ttg aag gag cct tta      627
Asn Ser Pro Arg Glu Ile Asn Gln Phe Ile Ser Leu Lys Glu Pro Leu
                190                 195                 200 gaa act tta gta ttt gga caa aag gtc ttc cat gcc gta acg cca ctt      675
Glu Thr Leu Val Phe Gly Gln Lys Val Phe His Ala Val Thr Pro Leu
            205                 210                 215
```

```
gga aca gaa tgt agt acg gag gct ttt cgt gat att tta tta gta aca      723
Gly Thr Glu Cys Ser Thr Glu Ala Phe Arg Asp Ile Leu Leu Val Thr
        220                 225                 230 ttt tct tat aag gag aca aaa taagagctc                                753
Phe Ser Tyr Lys Glu Thr Lys
    235                 240
```

<210> SEQ ID NO 44
<211> LENGTH: 240
<212> TYPE: PRT
<213> ORGANISM: Artificial Sequence
<220> FEATURE:
<223> OTHER INFORMATION: pMW199-IDO(Lys, 23) BamHI-SacI

<400> SEQUENCE: 44

```
Met Lys Met Ser Gly Phe Ser Ile Glu Glu Lys Val His Phe Glu
1               5                   10                  15

Ser Lys Gly Phe Leu Glu Ile Ser Asn Glu Ile Phe Leu Gln Glu Glu
            20                  25                  30

Glu Asn His Ser Leu Leu Thr Gln Ala Gln Leu Asp Tyr Tyr Asn Leu
        35                  40                  45

Glu Asp Ala Tyr Gly Glu Cys Arg Ala Arg Ser Tyr Ser Arg Tyr
50                  55                  60

Ile Lys Tyr Val Asp Ser Pro Asp Tyr Ile Leu Asp Asn Ser Asn Asp
65                  70                  75                  80

Tyr Phe Gln Ser Lys Glu Tyr Asn Tyr Asp Asp Gly Gly Lys Val Arg
                85                  90                  95

Gln Phe Asn Ser Ile Asn Asp Ser Phe Leu Cys Asn Pro Leu Ile Gln
            100                 105                 110

Asn Ile Val Arg Phe Asp Thr Glu Phe Ala Phe Lys Thr Asn Ile Ile
        115                 120                 125

Asp Lys Ser Lys Asp Leu Ile Ile Gly Leu His Gln Val Arg Tyr Lys
130                 135                 140

Ala Thr Lys Glu Arg Pro Ser Phe Ser Ser Pro Ile Trp Leu His Lys
145                 150                 155                 160

Asp Asp Glu Pro Val Val Phe Leu His Leu Met Asn Leu Ser Asn Thr
                165                 170                 175

Ala Ile Gly Gly Asp Asn Leu Ile Ala Asn Ser Pro Arg Glu Ile Asn
            180                 185                 190

Gln Phe Ile Ser Leu Lys Glu Pro Leu Glu Thr Leu Val Phe Gly Gln
        195                 200                 205

Lys Val Phe His Ala Val Thr Pro Leu Gly Thr Glu Cys Ser Thr Glu
210                 215                 220

Ala Phe Arg Asp Ile Leu Leu Val Thr Phe Ser Tyr Lys Glu Thr Lys
225                 230                 235                 240
```

<210> SEQ ID NO 45
<211> LENGTH: 753
<212> TYPE: DNA
<213> ORGANISM: Artificial Sequence
<220> FEATURE:
<223> OTHER INFORMATION: pMW199-IDO(Lys, 32) BamHI-SacI
<220> FEATURE:
<221> NAME/KEY: CDS
<222> LOCATION: (25)..(744)

<400> SEQUENCE: 45

```
ggatccttaa gaaggagata tacc atg aaa atg agt ggc ttt agc ata gaa        51
                          Met Lys Met Ser Gly Phe Ser Ile Glu
                          1               5
```

```
gaa aag gta cat gaa ttt gaa tct aaa ggg ttt ctt gaa atc tca aat      99
Glu Lys Val His Glu Phe Glu Ser Lys Gly Phe Leu Glu Ile Ser Asn
 10              15                  20                  25 gaa atc ttt tta caa gag gaa gag aat cat agt tta tta aca caa gca     147
Glu Ile Phe Leu Gln Glu Glu Glu Asn His Ser Leu Leu Thr Gln Ala
             30                  35                  40 cag tta gat tat tat aat ttg gaa gat gat gcg tac ggt gaa tgc cgt     195
Gln Leu Asp Tyr Tyr Asn Leu Glu Asp Asp Ala Tyr Gly Glu Cys Arg
                 45                  50                  55 gct aga tct tat tca agg tat ata aag tat gtt gat tca cca gat tat     243
Ala Arg Ser Tyr Ser Arg Tyr Ile Lys Tyr Val Asp Ser Pro Asp Tyr
 60                  65                  70 att tta gat aat agt aat gat tac ttc caa tct aaa gaa tat aac tat     291
Ile Leu Asp Asn Ser Asn Asp Tyr Phe Gln Ser Lys Glu Tyr Asn Tyr
     75                  80                  85 gat gat ggc ggg aaa gtt aga cag ttc aat agc ata aat gat agc ttt     339
Asp Asp Gly Gly Lys Val Arg Gln Phe Asn Ser Ile Asn Asp Ser Phe
 90                  95                 100                 105 ttg tgt aat cct tta att caa aat atc gtg cat ttc gat act gag ttt     387
Leu Cys Asn Pro Leu Ile Gln Asn Ile Val His Phe Asp Thr Glu Phe
                110                 115                 120 gca ttt aaa aca aat ata ata gat aaa agt aaa gat tta att ata ggc     435
Ala Phe Lys Thr Asn Ile Ile Asp Lys Ser Lys Asp Leu Ile Ile Gly
            125                 130                 135 tta cat caa gta aga tat aaa gct act aaa gaa aga cca tct ttt agt     483
Leu His Gln Val Arg Tyr Lys Ala Thr Lys Glu Arg Pro Ser Phe Ser
        140                 145                 150 tca cct att tgg tta cat aaa gat gat gaa cca gta gtg ttt tta cac     531
Ser Pro Ile Trp Leu His Lys Asp Asp Glu Pro Val Val Phe Leu His
    155                 160                 165 ctt atg aat tta agt aat aca gct atc ggc gga gat aat tta ata gct     579
Leu Met Asn Leu Ser Asn Thr Ala Ile Gly Gly Asp Asn Leu Ile Ala
170                 175                 180                 185 aat tct cct cgg gaa att aat cag ttt ata agt ttg aag gag ccg tta     627
Asn Ser Pro Arg Glu Ile Asn Gln Phe Ile Ser Leu Lys Glu Pro Leu
                190                 195                 200 gaa act tta gta ttt gga caa aag gtc ttc cat gcc gta acg cca ctt     675
Glu Thr Leu Val Phe Gly Gln Lys Val Phe His Ala Val Thr Pro Leu
            205                 210                 215 gga aca gaa tgt agt acg gag gct ttt cgt gat att tta tta gta aca     723
Gly Thr Glu Cys Ser Thr Glu Ala Phe Arg Asp Ile Leu Leu Val Thr
        220                 225                 230 ttt tct tat aag gag aca aaa taagagctc                                753
Phe Ser Tyr Lys Glu Thr Lys
    235                 240

<210> SEQ ID NO 46
<211> LENGTH: 240
<212> TYPE: PRT
<213> ORGANISM: Artificial Sequence
<220> FEATURE:
<223> OTHER INFORMATION: pMW199-IDO(Lys, 32) BamHI-SacI

<400> SEQUENCE: 46

Met Lys Met Ser Gly Phe Ser Ile Glu Glu Lys Val His Glu Phe Glu
 1               5                  10                  15

Ser Lys Gly Phe Leu Glu Ile Ser Asn Glu Ile Phe Leu Gln Glu Glu
             20                  25                  30

Glu Asn His Ser Leu Leu Thr Gln Ala Gln Leu Asp Tyr Tyr Asn Leu
         35                  40                  45

Glu Asp Asp Ala Tyr Gly Glu Cys Arg Ala Arg Ser Tyr Ser Arg Tyr
```

```
                 50                  55                  60
Ile Lys Tyr Val Asp Ser Pro Asp Tyr Ile Leu Asp Asn Ser Asn Asp
 65                  70                  75                  80

Tyr Phe Gln Ser Lys Glu Tyr Asn Tyr Asp Asp Gly Gly Lys Val Arg
                 85                  90                  95

Gln Phe Asn Ser Ile Asn Asp Ser Phe Leu Cys Asn Pro Leu Ile Gln
            100                 105                 110

Asn Ile Val His Phe Asp Thr Glu Phe Ala Phe Lys Thr Asn Ile Ile
            115                 120                 125

Asp Lys Ser Lys Asp Leu Ile Ile Gly Leu His Gln Val Arg Tyr Lys
130                 135                 140

Ala Thr Lys Glu Arg Pro Ser Phe Ser Ser Pro Ile Trp Leu His Lys
145                 150                 155                 160

Asp Asp Glu Pro Val Val Phe Leu His Leu Met Asn Leu Ser Asn Thr
                165                 170                 175

Ala Ile Gly Gly Asp Asn Leu Ile Ala Asn Ser Pro Arg Glu Ile Asn
            180                 185                 190

Gln Phe Ile Ser Leu Lys Glu Pro Leu Glu Thr Leu Val Phe Gly Gln
            195                 200                 205

Lys Val Phe His Ala Val Thr Pro Leu Gly Thr Glu Cys Ser Thr Glu
210                 215                 220

Ala Phe Arg Asp Ile Leu Leu Val Thr Phe Ser Tyr Lys Glu Thr Lys
225                 230                 235                 240

<210> SEQ ID NO 47
<211> LENGTH: 720
<212> TYPE: DNA
<213> ORGANISM: Bacillus thuringiensis
<220> FEATURE:
<221> NAME/KEY: CDS
<222> LOCATION: (

```
              130                 135                 140
act aaa gaa aga cca tct ttt agt tca cct att tgg tta cat aaa gat      480
Thr Lys Glu Arg Pro Ser Phe Ser Ser Pro Ile Trp Leu His Lys Asp
145                 150                 155                 160 gat gaa cca gta gtg ttt tta cac ctt atg aat tta agt aat aca gct      528
Asp Glu Pro Val Val Phe Leu His Leu Met Asn Leu Ser Asn Thr Ala
                165                 170                 175 att ggc gga gat aat tta ata gct aat tct cca agg gaa att aat cag      576
Ile Gly Gly Asp Asn Leu Ile Ala Asn Ser Pro Arg Glu Ile Asn Gln
            180                 185                 190 ttt ata agt ttg aag gag cct tta gaa act tta gta ttt gga caa aag      624
Phe Ile Ser Leu Lys Glu Pro Leu Glu Thr Leu Val Phe Gly Gln Lys
        195                 200                 205 gtt ttc cat gcc gta acg cca ctt gga aca gaa tgt agt act gaa gct      672
Val Phe His Ala Val Thr Pro Leu Gly Thr Glu Cys Ser Thr Glu Ala
    210                 215                 220 ttt cgt gat att tta tta gta aca ttt tct tat aag gag aca aaa tga      720
Phe Arg Asp Ile Leu Leu Val Thr Phe Ser Tyr Lys Glu Thr Lys
225                 230                 235

<210> SEQ ID NO 48
<211> LENGTH: 239
<212> TYPE: PRT
<213> ORGANISM: Bacillus thuringiensis

<400> SEQUENCE: 48

Lys Met Ser Gly Phe Ser Ile Glu Glu Lys Val His Glu Phe Glu Ser
1               5                   10                  15

Lys Gly Phe Leu Glu Ile Ser Asn Glu Ile Phe Leu Gln Glu Glu Glu
            20                  25                  30

Asn His Arg Leu Leu Thr Gln Ala Gln Leu Asp Tyr Tyr Asn Leu Glu
        35                  40                  45

Asp Asp Ala Tyr Gly Glu Cys Arg Ala Arg Ser Tyr Ser Arg Tyr Ile
    50                  55                  60

Lys Tyr Val Asp Ser Pro Asp Tyr Ile Leu Asp Asn Ser Asn Asp Tyr
65                  70                  75                  80

Phe Gln Ser Lys Glu Tyr Asn Tyr Asp Asp Gly Gly Lys Val Arg Gln
                85                  90                  95

Phe His Ser Ile Asn Asp Ser Phe Leu Tyr Asn Pro Leu Ile Gln Asn
            100                 105                 110

Ile Val Arg Phe Asp Thr Glu Phe Ala Phe Lys Thr Asn Ile Ile Asp
        115                 120                 125

Thr Ser Lys Asp Leu Ile Ile Gly Leu His Gln Val Arg Tyr Lys Ala
    130                 135                 140

Thr Lys Glu Arg Pro Ser Phe Ser Ser Pro Ile Trp Leu His Lys Asp
145                 150                 155                 160

Asp Glu Pro Val Val Phe Leu His Leu Met Asn Leu Ser Asn Thr Ala
                165                 170                 175

Ile Gly Gly Asp Asn Leu Ile Ala Asn Ser Pro Arg Glu Ile Asn Gln
            180                 185                 190

Phe Ile Ser Leu Lys Glu Pro Leu Glu Thr Leu Val Phe Gly Gln Lys
        195                 200                 205

Val Phe His Ala Val Thr Pro Leu Gly Thr Glu Cys Ser Thr Glu Ala
    210                 215                 220

Phe Arg Asp Ile Leu Leu Val Thr Phe Ser Tyr Lys Glu Thr Lys
225                 230                 235
```

<210> SEQ ID NO 49
<211> LENGTH: 720
<212> TYPE: DNA
<213> ORGANISM: Bacillus thuringiensis

<400> SEQUENCE: 49

```

-continued

```
Phe Arg Asp Ile Leu Leu Val Thr Phe Ser Tyr Lys Glu Thr Lys
225                 230                 235

<210> SEQ ID NO 51
<211> LENGTH: 239
<212> TYPE: PRT
<213> ORGANISM: Bacillus weihenstephanensis

<400> SEQUENCE: 51

Lys Thr Ser Ser Phe Asp Val Glu Gln Lys Val His Glu Phe Glu Ser
1               5                   10                  15

Asn Gly Tyr Ile Gln Ile Phe Asn Asp Ile Phe Leu Gln Asp Gln Glu
            20                  25                  30

Asp Gln Ala Leu Leu Thr Lys Ala Gln Leu Asp Tyr Tyr Ser Leu Gln
        35                  40                  45

Asn Asp Ala Tyr Gly Glu Cys Arg Ala Arg Ala Tyr Ser Arg Tyr Ile
    50                  55                  60

Lys Tyr Ala Gly Ser Ser Asp Tyr Val Leu Asp Thr Asp Asn Gly Tyr
65                  70                  75                  80

Phe Gln Ser Glu Glu Tyr Asn Tyr Asp Asp Gly Gly Lys Ile Arg Asn
                85                  90                  95

Phe Asn Ser Ile Thr Asp Glu Phe Leu His Asn Ser Leu Ile Glu Lys
            100                 105                 110

Ile Val Arg Phe Asp Ser Glu Phe Ala Ser Asn Thr Asn Ile Leu Asp
        115                 120                 125

Thr Ser Lys Asp Leu Val Ile Gly Leu His Gln Val Arg Tyr Lys Ala
    130                 135                 140

Thr Arg Glu Asn Pro Ser Phe Ser Ser Pro Ile Trp Leu His Lys Asp
145                 150                 155                 160

Asp Glu Pro Ile Val Phe Leu His Leu Met Asn Leu Ser Asn Thr Ala
                165                 170                 175

Leu Gly Gly Asp Asn Leu Ile Ala Asn Ser Pro Arg Glu Ile Asn Lys
            180                 185                 190

Leu Ile Ser Leu Lys Asp Pro Leu Glu Thr Leu Val Phe Gly Gln Lys
        195                 200                 205

Val Phe His Ala Val Thr Pro Leu Gly Thr Glu Cys Asn Thr Glu Ala
    210                 215                 220

Leu Arg Asp Ile Leu Leu Val Thr Phe Ser Tyr Lys Glu Pro Lys
225                 230                 235
```